United States Patent
Frohberg et al.

(10) Patent No.: US 10,428,341 B2
(45) Date of Patent: *Oct. 1, 2019

(54) TRANSGENIC POTATO PLANTS WITH INCREASED HYALURONAN PRODUCTION

(75) Inventors: Claus Frohberg, Kleinmachnow (DE); Bernd Essigmann, Berlin (DE)

(73) Assignee: BASF SE, Ludwigshafen am Rhein (DE)

(*) Notice: Subject to any disclaimer, the term of this patent is extended or adjusted under 35 U.S.C. 154(b) by 637 days.

This patent is subject to a terminal disclaimer.

(21) Appl. No.: 12/089,270

(22) PCT Filed: Oct. 5, 2006

(86) PCT No.: PCT/EP2006/009773
§ 371 (c)(1),
(2), (4) Date: Apr. 4, 2008

(87) PCT Pub. No.: WO2007/039314
PCT Pub. Date: Apr. 12, 2007

(65) Prior Publication Data
US 2009/0151016 A1 Jun. 11, 2009

Related U.S. Application Data

(60) Provisional application No. 60/725,388, filed on Oct. 11, 2005.

(30) Foreign Application Priority Data

Oct. 5, 2005 (EP) .................................. 05090279

(51) Int. Cl.
*C12N 15/82* (2006.01)
*C12N 9/10* (2006.01)

(52) U.S. Cl.
CPC ....... *C12N 15/8243* (2013.01); *C12N 9/1051* (2013.01); *C12N 9/1096* (2013.01)

(58) Field of Classification Search
None
See application file for complete search history.

(56) References Cited

U.S. PATENT DOCUMENTS

| | | | | |
|---|---|---|---|---|
| 5,294,593 | A * | 3/1994 | Khan | 504/100 |
| 8,106,256 | B2 * | 1/2012 | Frohberg et al. | 800/288 |
| 8,558,060 | B2 * | 10/2013 | Frohberg et al. | 800/295 |
| 2003/0092118 | A1 * | 5/2003 | DeAngelis et al. | 435/69.1 |
| 2003/0175902 | A1 * | 9/2003 | Sloma | C12N 9/1051 435/84 |
| 2003/0177534 | A1 * | 9/2003 | Nichols et al. | 800/284 |
| 2005/0202540 | A1 | 9/2005 | Weigel et al. | |
| 2006/0115545 | A1 * | 6/2006 | Frohberg et al. | 424/750 |
| 2006/0168690 | A1 * | 7/2006 | Shibatani et al. | 800/284 |
| 2008/0250533 | A1 * | 10/2008 | Frohberg | 800/284 |
| 2009/0199311 | A1 * | 8/2009 | Frohberg et al. | 800/278 |

FOREIGN PATENT DOCUMENTS

| | | | |
|---|---|---|---|
| EP | 1 640 457 | 3/2006 | |
| WO | WO 2004/003175 | * 1/2004 | |
| WO | WO 2005/012529 | * 2/2005 | ............ C12N 15/56 |
| WO | WO 2006/032538 | 3/2006 | |
| WO | WO 2005/012529 | 5/2006 | |
| WO | WO 2007/039314 | 4/2007 | |
| WO | WO 2007/039315 | 4/2007 | |
| WO | WO 2007/039316 | 4/2007 | |
| WO | WO 2007/039317 | 4/2007 | |

OTHER PUBLICATIONS

Landestein et al. Chlorella Virus PBCV-1 encodes functional glutamine:fructose-6-phosphate amidotransferase and UDP-glucose dehydrogenase enzymes. (1998) Virology; vol. 250; pp. 388-396.*
Horvath et al. The production of recombinant proteins in transgenic barley grains. (2000) PNAS; vol. 97; pp. 1914-1919.*
Graves et al. Hyaluronan synthesis in Virus PBCV-1-Infected chlorella-like green algae. (1999) Virology; vol. 257; pp. 15-23. (Year: 1999).*
Raskin et al. Plants and human health in the twenty-first century. (2002) Trends in Biotechnology; vol. 20; pp. 522-531 (Year: 2002).*
Graves, et al. (Apr. 25, 1999) "Hyaluronan Synthesis in Virus PBCV-1-Infected Chlorella-like Green Algae." Virology 257(1): 15-23.
Deangelis, et al. (Dec. 5, 1997) "Hyaluronan Synthase of Chloreila Virus PBCV-1." Science 278(5344): 1800-1803.
Graack, et al. (2001) "Functional regulation of glutamine: fructose-6-phosphate aminotransferase 1 (GFAT1) of *Drosophila melanogaster* in a UDP-N-acetylglucosamine and cAMP-dependent manner." Biochem. J. 360: 401-412.

* cited by examiner

*Primary Examiner* — Cathy Kingdon Worley
(74) *Attorney, Agent, or Firm* — Arent Fox LLP

(57) ABSTRACT

The present invention relates to a process for increasing the phosphate content of starches of genetically modified plant cells in comparison with starches from corresponding wild-type plant cells by introducing a foreign nucleic acid molecule which codes for a soluble starch synthase II. The present invention furthermore relates to the overexpression of this soluble starch synthase II in the genetically modified plant cells. Furthermore, the present invention relates to rice starch and rice flour with improved quality characteristics, to rice grains comprising this rice starch, and to rice plants on which these rice grains grow.

14 Claims, 1 Drawing Sheet
Specification includes a Sequence Listing.

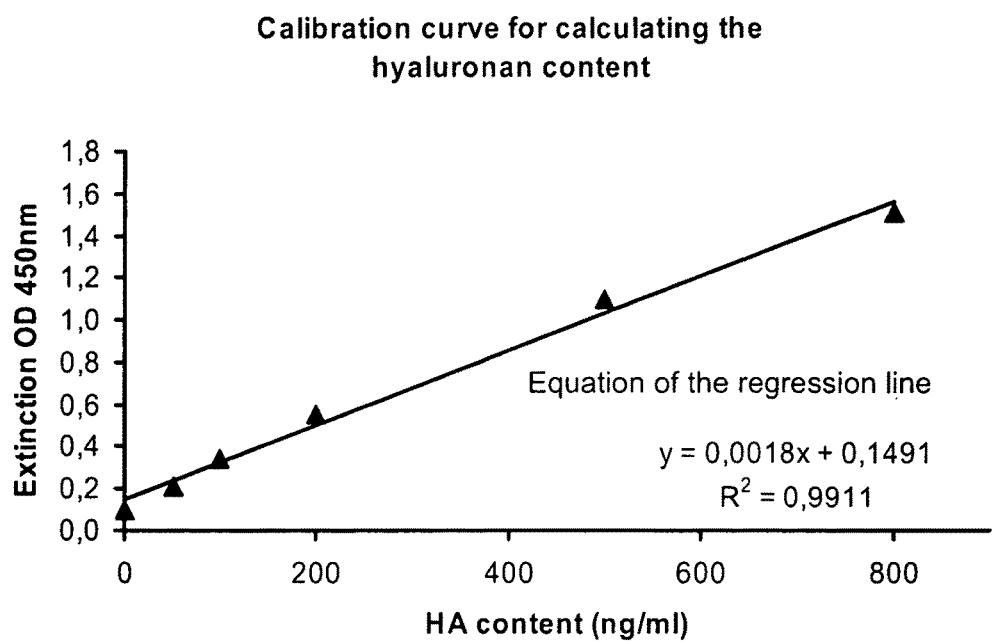

TRANSGENIC POTATO PLANTS WITH INCREASED HYALURONAN PRODUCTION

CROSS-REFERENCE TO RELATED APPLICATIONS

This application is the U.S. National Stage filing of International Application No. PCT/EP2006/009773, filed Oct. 5, 2006, which claims priority to EP 05090279.0, filed Oct. 5, 2005, and U.S. Provisional Patent Application No. 60/725,388, filed Oct. 11, 2005, the disclosures of each of which are hereby incorporated by reference.

BACKGROUND OF THE INVENTION

(i) Field of the Invention

The present invention relates to plant cells and plants which synthesize an increased amount of hyaluronan, and to methods for preparing such plants, and also to methods for preparing hyaluronan with the aid of these plant cells or plants. Here, plant cells or genetically modified plants according to the invention have hyaluronan synthase activity and additionally an increased glutamine:fructose 6-phosphate amidotransferase (GFAT) activity compared to wild-type plant cells or wild-type plants. The present invention furthermore relates to the use of plants having increased hyaluronan synthesis for preparing hyaluronan and food or feedstuff containing hyaluronan.

(ii) Description of the Related Art

Hyaluronan is a naturally occurring unbranched, linear mucopolysaccharide (glucosaminoglucan) which is constructed of alternating molecules of glucuronic acid and N-acetyl-glucosamine. The basic building block of hyaluronan consists of the disaccharide glucuronic acid-beta-1,3-N-acetyl-glucosamine. In hyaluronan, these repeating units are attached to one another via beta-1,4 linkages.

In pharmacy, use is frequently made of the term hyaluronic acid. Since hyaluronan is in most cases present as a polyanion and not as the free acid, hereinbelow, the term hyaluronan is preferably used, but each term is to be understood as embracing both molecular forms.

Hyaluronan has unusual physical chemical properties, such as, for example, properties of polyelectrolytes, viscoelastic properties, a high capacity to bind water, properties of gel formation, which, in addition to further properties of hyaluronan, are described in a review article by Lapcik et al. (1998, Chemical Reviews 98(8), 2663-2684).

Hyaluronan is a component of extracellular connective tissue and bodily fluids of vertebrates. In humans, hyaluronic acid is synthesized by the cell membrane of all body cells, especially mesenchymal cells, and ubiquitously present in the body with a particularly high concentration in the connective tissues, the extracellular matrix, the umbilical cord, the joint fluid, the cartilaginous tissue, the skin and the vitreous body of the eye (Bernhard Gebauer, 1998, Inaugural-Dissertation, Virchow-Klinikum Medizinische Fakultät Charité der Humboldt Universität zu Berlin; Fraser et al., 1997, Journal of Internal Medicine 242, 27-33).

Recently, hyaluronan was also found in animal non-vertebrate organisms (molluscs) (Volpi and Maccari, 2003, Biochimie 85, 619-625).

Furthermore, some pathogenic gram-positive bacteria (Streptococcus group A and C) and gram-negative bacteria (Pasteurella) synthesize hyaluronan as exopoly-saccharides which protect these bacteria against attack by the immune system of their host, since hyaluronan is a non-immunogenic substance.

Viruses which infect single-cell green algae of the genus Chlorella, some of which are present as endosymbionts in Paramecium species, bestow upon the single-cell green algae the ability to synthesize hyaluronan after infection by the virus (Graves et al., 1999, Virology 257, 15-23). However, the ability to synthesize hyaluronan is not a feature which characterizes the algae in question. The ability of the algae to synthesize hyaluronan is mediated by an infection with a virus whose genome has a sequence coding for hyaluronan synthase (DeAngelis, 1997, Science 278, 1800-1803). Furthermore, the virus genome contains sequences coding for a glutamine: fructose 6-phosphate amidotransferase (GFAT). GFAT converts fructose 6-phosphate and glutamine into glucosamine 6-phosphate which is an important metabolite in the metabolic pathway for hyaluronan synthesis. Both genes encode active proteins which, like the hyaluronan synthase of the virus, are transcribed simultaneously in the early phase of the viral infection (DeAngelis et al., 1997, Science 278, 1800-1803, Graves et al., 1999, Virology 257, 15-23). The activity of a protein having glutamine:fructose 6-phosphate amidotransferase (GFAT) activity could be detected neither in extracts from cells not infected by a virus nor in virus-infected cells (Landstein et al., 1998, Virology 250, 388-396). Accordingly, the role of the expression of GFAT in virus-infected Chlorella cells for the hyaluronan synthesis, and whether they are required for hyaluronan synthesis, is not known.

Naturally occurring plants themselves do not have any nucleic acids in their genome which code for proteins catalyzing the synthesis of hyaluronan and, although a large number of plant carbohydrates have been described and characterized, it has hitherto not been possible to detect hyaluronan or molecules related to hyaluronan in non-infected plants (Graves et al., 1999, Virology 257, 15-23).

The catalysis of the hyaluronan synthesis is effected by a single membrane-integrated or membrane-associated enzyme, hyaluronan synthase. The hyaluronan synthases which have hitherto been studied can be classified into two groups: hyaluronan synthases of Class I and hyaluronan synthases of Class II (DeAngelis, 1999, CMLS, Cellular and Molecular Life Sciences 56, 670-682).

The hyaluronan synthases of vertebrates are further distinguished by the identified isoenzymes. The different isoenzymes are referred to in the order of their identification using Arabic numbers (for example, hsHAS1, hsHAS2, hsHAS3).

The mechanism of the transfer of synthesized hyaluronan molecules across the cytoplasma membrane into the medium surrounding the cell has not yet been fully elucidated. Earlier hypotheses assumed that transport across the cell membrane was effected by hyaluronan synthase itself. However, more recent results indicate that the transport of hyaluronan molecules across the cytoplasma membrane takes place by energy-dependent transport via transport proteins responsible for this action. Thus, Streptococcus strains were generated by mutation in which the synthesis of an active transport protein was inhibited. These strains synthesized less hyaluronan than corresponding wild-type bacteria strains (Ouskova et al., 2004, Glycobiology 14(10), 931-938). In human fibroblasts, it was possible to demonstrate, with the aid of agents specifically inhibiting known transport proteins, that it is possible to reduce both the amount of hyaluronan produced and the activity of hyaluronan synthases (Prehm and Schumacher, 2004, Biochemical Pharmacology 68, 1401-1410). In which amount, if at all, transport proteins capable of transporting hyaluronan are present in plants is not known.

The unusual properties of hyaluronan offer a wealth of possibilities for application in various fields, such as, for example, pharmacy, the cosmetics industry, in the production of food and feed, in technical applications (for example as lubricants), etc. The most important applications where hyaluronan is currently being used are in the medicinal and cosmetics field (see, for example, Lapcik et al., 1998, Chemical Reviews 98(8), 2663-2684, Goa and Benfield, 1994, Drugs 47(3), 536-566).

In the medical field, hyaluronan-containing products are currently used for the intraarticular treatment of arthrosis and in ophthalmics used for eye surgery. Hyaluronan is also used for treating joint disorders in racehorses. In addition, hyaluronic acid is a component of some rhinologics which, for example in the form of eye drops and nasalia, serve to moisten dry mucous membranes. Hyaluronan-containing solutions for injection are used as analgesics and antirheumatics. Patches comprising hyaluronan or derivatized hyaluronan are employed in wound healing. As dermatics, hyaluronan-containing gel implants are used for correcting skin deformations in plastic surgery.

For pharmacological applications, preference is given to using hyaluronan having a high molecular weight.

In cosmetic medicine, hyaluronan preparations are among the most suitable skin filler materials. By injecting hyaluronan, for a limited period of time, it is possible to smooth wrinkles or to increase the volume of lips.

In cosmetic products, in particular in skin creams and lotions, hyaluronan is frequently used as moisturizer by virtue of its high water-binding capacity.

Furthermore, hyaluronan-containing preparations are sold as so-called nutraceuticals (food supplements) which can also be used in animals (for example dogs, horses) for the prophylaxis and alleviation of arthrosis.

Hyaluronan used for commercial purposes is currently isolated from animal tissues (roostercombs) or prepared fermentatively using bacterial cultures.

U.S. Pat. No. 4,141,973 describes a process for isolating hyaluronan from roostercombs or alternatively from umbilical cords. In addition to hyaluronan, animal tissues (for example roostercombs, umbilical cords) also contain further mucopolysaccharides related to hyaluronan, such as chondroitin sulfate, dermatan sulfate, keratan sulfate, heparan sulfate and heparin. Furthermore, animal organisms contain proteins (hyaladherins) which bind specifically to hyaluronan and which are required for the most different functions in the organism, such as, for example, the degradation of hyaluronan in the liver, the function of hyaluronan as lead structure for cell migration, the regulation of endocytosis, the anchoring of hyaluronan on the cell surface or the formation of hyaluronan networks (Turley, 1991, Adv Drug Delivery Rev 7, 257 ff.; Laurent and Fraser, 1992, FASEB J. 6, 183 ff.; Stamenkovic and Aruffo, 1993, Methods Enzymol. 245, 195 ff; Knudson and Knudson, 1993, FASEB 7, 1233 ff.).

The *Streptococcus* strains used for the bacterial production of hyaluronan are exclusively pathogenic bacteria. During cultivation, too, these bacteria produce (pyrogenic) exotoxins and hemolysins (streptolysin, (in particular alpha- and beta-hemolysin) (Kilian, M.: *Streptococcus* and *Enterococcus*. In: *Medical Microbiology*. Greenwood, D.; Slack, RCA; Peutherer, J. F. (Eds.). Chapter 16. Churchill Livingstone, Edinburgh, UK: pp. 174-188, 2002, ISBN 0443070776) which are released into the culture medium. This renders purification and isolation of the hyaluronan prepared with the aid of *Streptococcus* strains more difficult. In particular for pharmaceutical application, the presence of exotoxins and hemolysins in the preparation is a problem.

U.S. Pat. No. 4,801,539 describes the preparation of hyaluronan by fermentation of a mutagenized bacterial strain (*Streptococcus zooedemicus*). The mutagenized bacteria strain used no longer synthesizes beta-hemolysin. The yield achieved was 3.6 g of hyaluronan per liter of culture.

EP 0694616 describes a method for cultivating *Streptococcus zooedemicus* or *Streptococcus equi*, where, under the culture conditions employed, no streptolysin, but increased amounts of hyaluronan are synthesized. The yield achieved was 3.5 g of hyaluronan per liter of culture.

During cultivation, *Streptococcus* strains release the enzyme hyaluronidase into the culture medium, as a consequence of which, in this production system, too, the molecular weight is reduced during purification. The use of hyaluronidase-negative *Streptococcus* strains or of methods for the production of hyaluronan where the production of hyaluronidase during cultivation is inhibited are described in U.S. Pat. No. 4,782,046. The yield achieved was up to 2.5 g of hyaluronan per liter of culture, and the maximum mean molecular weight achieved was $3.8 \times 10^6$ Da, at a molecular weight distribution of from $2.4 \times 10^6$ to $4.0 \times 10^6$.

US 20030175902 and WO 03 054163 describe the preparation of hyaluronan with the aid of heterologous expression of a hyaluronan synthase from *Streptococcus equisimilis* in *Bacillus subtilis*. To achieve the production of sufficient amounts of hyaluronan, in addition to heterologous expression of a hyaluronan synthase, simultaneous expression of a UDP-glucose dehydrogenase in the *Bacillus* cells is also required. US 20030175902 and WO 03 054163 do not state the absolute amount of hyaluronan obtained in the production with the aid of *Bacillus subtilis*. The maximum mean molecular weight achieved was about $4.2 \times 10^6$. However, this mean molecular weight was only achieved for the recombinant *Bacillus* strain where a gene coding for the hyaluronan synthase gene from *Streptococcus* equisimilis and the gene coding for the UDP-glucose dehydrogenase from *Bacillus subtilis* were integrated into the *Bacillus subtilis* genome under the control of the amyQ promoter, where at the same time the *Bacillus subtilis*-endogenous cxpY gene (which codes for a cytochrome P450 oxidase) was inactivated.

WO 05 012529 describes the preparation of transgenic tobacco plants which were transformed using nucleic acid molecules encoding for hyaluronan synthases from *Chlorella*-infecting viruses. In WO 05 012529, use was made, on the one hand, of nucleic acid sequences encoding for hyaluronan synthase of the *Chlorella* virus strain CVHI1 and, on the other hand, of the *Chlorella* virus strain CVKA1 for transforming tobacco plants. The synthesis of hyaluronan could only be demonstrated for a plant transformed with a nucleic acid encoding for a hyaluronan synthase isolated from the *Chlorella* virus strain CVKA1. For tobacco plants transformed with a nucleic acid sequence encoding for a hyaluronan synthase isolated from the *Chlorella* virus strain CVHI1, it was not possible to detect hyaluronan synthesis in the corresponding transgenic plants. The amount of hyaluronan synthesized by the only hyaluronan-producing transgenic tobacco plant in WO 05 012529 is stated as being about 4.2 µg of hyaluronan per ml of measured volume which, taking into account the description for carrying out the experiment in question, corresponds approximately to an amount of at most 12 µg of hyaluronan produced per gram of fresh weight of plant material.

Hyaluronan synthase catalyzes the synthesis of hyaluronan from the starting materials UDP-N-acetyl-glucosamine and UDP-glucuronic acid. Both starting materials mentioned are present in plant cells.

For the synthesis of UDP-N-acetylglucosamine in plant cells, WO 98 35047 describes a metabolic path where glucosamine is converted by a number of successive enzymatically catalyzed reaction steps with formation of the metabolites N-acetyl-glucosamine, N-acetyl-glucosamine 6-phosphate, N-acetyl-glucosamine 1-phosphate into UDP-N-acetylglucosamine. An alternative metabolic path comprises a reaction of fructose 6-phosphate and glutamine giving glucosamine 6-phosphate which is subsequently converted by a number of successive enzymatically catalyzed reaction steps with formation of the metabolites glucosamine 1-phosphate and N-acetyl-glucosamine 1-phosphate into UDP-N-acetylglucosamine. The conversion of fructose 6-phosphate and glutamine into glucosamine 6-phosphate is catalyzed by a protein having glutamine:fructose 6-phosphate amidotransferase (GFAT) activity (Mayer et al., 1968, Plant Physiol. 43, 1097-1107).

WO 00 11192 describes the endosperm-specific overexpression of a nucleic acid molecule of corn encoding for a protein having the enzyme activity of a GFAT in transgenic corn plants with the aim to synthesize a cationic starch in plants which has 2-amino-anhydroglucose molecules. The metabolic path described which, according to the description of WO 00 11192 should result in 2-amino-anhydroglucose being incorporated into the starch, comprises inter alia the incorporation of UDP-glucosamine by starch synthases and/or glycogen synthases into the starch. It is stated that increased amounts of UDP-glucosamine could be detected in flour from endosperm of the transgenic corn plants in question overexpressing a nucleic acid molecule encoding for a protein having the (enzymatic) activity of a GFAT translationally fused with a plastid signal peptide. When the protein having the (enzymatic) activity of a GFAT was expressed without signal peptide, it was possible to detect an increased amount of glucosamine 1-phosphate in the corresponding flours from corn endosperm tissue. It was not possible to detect cationic starch in the transgenic plants.

The production of hyaluronan by fermentation of bacteria strains is associated with high costs, since the bacteria have to be fermented in sealed sterile containers under expensive controlled culture conditions (see, for example, U.S. Pat. No. 4,897,349). Furthermore, the amount of hyaluronan which can be produced by fermentation of bacteria strains is limited by the production facilities present in each case. Here, it also has to be taken into account that fermenters, as a consequence of physical laws, cannot be built for excessively large culture volumes. Particular mention may be made here of homogeneous mixing of the substances fed in from the outside (for example essential nutrient sources for bacteria, reagents for regulating the pH, oxygen) with the culture medium required for efficient production, which, in large fermenters, can be ensured only with great technical expenditure, if at all.

The purification of hyaluronan from animal organisms is complicated owing to the presence, in animal tissues, of other mucopolysaccharides and proteins which specifically bind to hyaluronan. In patients, the use of hyaluronan-containing medicinal preparations contaminated by animal proteins can result in unwanted immunological reactions of the body (U.S. Pat. No. 4,141,973), in particular if the patient is allergic to animal proteins (for example chicken egg white). Furthermore, the amounts (yields) of hyaluronan which can be obtained from animal tissues in satisfactory quality and purity are low (croosterscomb: 0.079% w/w, EP 0144019, U.S. Pat. No. 4,782,046), which necessitates the processing of large amounts of animal tissues. A further problem in the isolation of hyaluronan from animal tissues consists in effect that the molecular weight of hyaluronan during purification is reduced since animal tissues also contain a hyaluronan-degrading enzyme (hyaluronidase).

In addition to the hyaluronidases and exotoxins mentioned, *Streptococcus* strains also produce endotoxins which, when present in pharmacological products, pose risks for the health of the patient. In a scientific study, it was shown that even hyaluronan-containing medicinal products on the market contain detectable amounts of bacterial endotoxins (Dick et al., 2003, Eur J. Opthalmol. 13(2), 176-184). A further disadvantage of the hyaluronan produced with the aid of *Streptococcus* strains is the fact that the isolated hyaluronan has a lower molecular weight than hyaluronan isolated from roostercombs (Lapcik et al. 1998, Chemical Reviews 98(8), 2663-2684). US 20030134393 describes the use of a *Streptococcus* strain for producing hyaluronan which synthesizes a particularly pronounced hyaluronan capsule (supercapsulated). The hyaluronan isolated after fermentation had a molecular weight of $9.1 \times 10^6$. However, the yield was only 350 mg per liter.

Some of the disadvantages of producing hyaluronan by bacterial fermentation or by isolation from animal tissues can be avoided by producing hyaluronan using transgenic plants; however, the currently achieved amounts of hyaluronan which can be produced using transgenic plants would require a relatively large area under cultivation to produce relatively large amounts of hyaluronan. Furthermore, the isolation or purification of hyaluronan from plants having a lower hyaluronan content is considerably more complicated and costly than the isolation or purification from plants having a higher hyaluronan content.

Although hyaluronan has unusual properties, it is, owing to its scarcity and the high price, rarely, if at all, used for industrial applications.

SUMMARY OF THE INVENTION

Accordingly, it is an object of the present invention to provide means and methods which permit the provision of hyaluronan in sufficient amounts and quality and which make it possible to provide hyaluronan even for industrial applications and applications in the field of food and feed.

This object is achieved by the embodiments outlined in the claims.

DETAILED DESCRIPTION OF THE INVENTION

Thus, the present invention relates to genetically modified plant cells or genetically modified plants having a nucleic acid molecule, stably integrated into their genome, encoding for a hyaluronan synthase, characterized in that said plant cells or said plants additionally have increased activity of a protein having an (enzymatic) glutamine:fructose 6-phosphate amidotransferase (GFAT) activity compared to corresponding not genetically modified wild-type plant cells or not genetically modified wild-type plants.

Here, the genetic modification of genetically modified plant cells according to the invention or genetically modified plants according to the invention can be any genetic modification resulting in a stable integration of a nucleic acid molecule encoding for a hyaluronan synthase into a plant cell or a plant and increasing the activity of a protein having the (enzymatic) activity of a GFAT in genetically modified plant cells or genetically modified plants, compared to corresponding not genetically modified wild-type plant cells or not genetically modified wild-type plants.

In the context of the present invention, the term "wild-type plant cell" is to be understood as meaning plant cells which served as starting material for the preparation of the genetically modified plant cells according to the invention, i.e. their genetic information, apart from the genetic modifications introduced and resulting in a stable integration of a nucleic acid molecule encoding for a hyaluronan synthase and increasing the activity of a protein having the activity of a GFAT, corresponds to that of a genetically modified plant cell according to the invention.

In the context of the present invention, the term "wild-type plant" is to be understood as meaning plants which served as starting material for the preparation of the genetically modified plants according to the invention, i.e. their genetic information, apart from the genetic modifications introduced and resulting in a stable integration of a nucleic acid molecule encoding for a hyaluronan synthase and increasing the activity of a protein having the activity of a GFAT, corresponds to that of a genetically modified plant according to the invention.

In the context of the present invention, the term "corresponding" means that, when a plurality of objects are compared, the objects in question which are compared to one another have been kept under the same conditions. In the context of the present invention, the term "corresponding" in the context of wild-type plant cells or wild-type plants means that the plant cells or plants compared to one another were cultivated under the same cultivation conditions and that they have the same (culture) age.

In the context of the present invention, the term "hyaluronan synthase" (EC 2.4.1.212) is to be understood as meaning a protein which synthesizes hyaluronan from the substrates UDP-glucuronic acid (UDP-GlcA) and N-acetyl-glucosamine (UDP-GlcNAc). The hyaluronan synthesis is catalyzed according to the reaction schemes below:

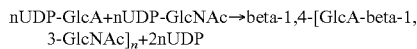

nUDP-GlcA+nUDP-GlcNAc→beta-1,4-[GlcA-beta-1,
3-GlcNAc]$_n$+2nUDP

Nucleic acid molecules and corresponding protein sequences coding for hyaluronan synthases have been described, inter alia, for the following organisms: rabbit (*Oryctolagus cuniculus*) ocHas2 (EMBL AB055978.1, US 20030235893), ocHas3 (EMBL AB055979.1, US 20030235893); baboon (*Papio anubis*) paHas1 (EMBL AY463695.1); frog (*Xenopus laevis*) xlHas1 (EMBL M22249.1, US 20030235893), xlHas2 (DG42) (EMBL AF168465.1), xlHas3 (EMBL AY302252.1); human (*Homo sapiens*) hsHAS1 (EMBL D84424.1, US 20030235893), hsHAS2 (EMBL U54804.1, US 20030235893), hsHAS3 (EMBL AF232772.1, US 20030235893); mouse (*Mus musculus*), mmHas1 (EMBL D82964.1, US 20030235893), mmHAS2 (EMBL U52524.2, US 20030235893), mmHas3 (EMBL U86408.2, US 20030235893); cattle (*Bos taurus*) btHas2 (EMBL AJ004951.1, US 20030235893); chicken (*Gallus gallus*) ggHas2 (EMBL AF106940.1, US 20030235893); rat (*Rattus norvegicus*) mHas 1 (EMBL AB097568.1, Itano et al., 2004, J. Biol. Chem. 279(18) 18679-18678), mHas2 (EMBL AF008201.1); mHas 3 (NCBI NM_172319.1, Itano et al., 2004, J. Biol. Chem. 279(18) 18679-18678), horse (*Equus caballus*) ecHAS2 (EMBL AY056582.1, GI:23428486), pig (*Sus scrofa*) sscHAS2 (NCBI NM_214053.1, GI:47522921), sscHas 3 (EMBL AB159675), zebra fish (*Danio rerio*) brHas1 (EMBL AY437-407), brHas2 (EMBL AF190742.1) brHas3 (EMBL AF190743.1); *Pasteurella multocida* pmHas (EMBL AF036004.2); *Streptococcus pyogenes* spHas (EMBL, L20853.1, L21187.1, U.S. Pat. No. 6,455,304, US 20030235893); *Streptococcus equis* seHas (EMBL AF347022.1, AY173078.1), *Streptococcus uberis* suHasA (EMBL AJ242946.2, US 20030235893), *Streptococcus equisimilis* seqHas (EMBL AF023876.1, US 20030235893); *Sulfolobus solfataricus* ssHAS (US 20030235893), *Sulfolobus tokodaii* stHas (AP000988.1), *Paramecium bursaria Chlorella* Virus 1, cvHAS (EMBL U42580.3, PB42580, US 20030235893).

In the context of the present invention, the term "glutamine:fructose 6-phosphate amidotransferase (GFAT)" (E.C. 2.6.1.16), in the expert literature also referred to as glucosamine synthase, is to be understood as meaning a protein which synthesizes, from the substrates glutamine and fructose 6-phosphate (Fruc-6-P) glucosamine 6-phosphate (GlcN-6-P). This catalysis proceeds according to the following reaction scheme:

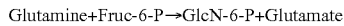

Glutamine+Fruc-6-P→GlcN-6-P+Glutamate

In particular in animal organisms, it was possible to demonstrate two different isoforms of proteins having the (enzymatic) activity of a GFAT (referred to as GFAT-1 and GFAT-2, respectively, in the literature). Hu et al. (2004), J. Biol. Chem. 279(29), 29988-29993 describe differences of the respective proteins from the mouse: in addition to differences in the tissue-specific expression of the proteins in question having the (enzymatic) activity of a glutamine: fructose 6-phosphate amidotransferase 1 (GFAT-1) and a glutamine:fructose 6-phosphate amidotransferase 2 (GFAT-2), it was possible to show that both isoforms are regulated by phosphorylation by a cAMP-dependent protein kinase. The activity of a protein having the (enzymatic) activity of a GFAT-1 is inhibited by phosphorylation of a conserved serine residue (serine 205 in the GFAT-1 from the mouse, GenBank Acc No.: AF334736.1) of the amido acid sequence in question, whereas the activity of a protein having the activity of a GFAT-2 is increased by phosphorylation of a conserved serine residue (serine 202 in the GFAT-2 from the mouse, GenBank Acc No.: NM_013529) of the amino acid sequence in question. Both proteins having the activity of a GFAT-1 and proteins having the activity of a GFAT-2 are inhibited in a concentration-dependent manner by UDP-N-acetylglucosamine; however, for a protein having the activity of a GFAT-2, the inhibition by UDP-N-acetylglucosamine is lower (maximum reduction of activity by UDP-N-acetylglucosamine about 15%) compared to a protein having the activity of a GFAT-1 (maximum reduction of activity by UDP-N-acetylglucosamine about 51% or 80%). There are indications that the inhibition of a protein having the activity of a GFAT-1 in animal organisms is based on the fact that at elevated UDP-N-acetylglucosamine concentrations there is an O-glucose-N-acetylglucosamine glycosylation of the proteins in question. Whether a regulation of the activity of proteins by O-glycosylation also takes place in plant cells is not yet fully understood (Huber und Hardin, 2004, Current Opinion in Plant Biotechnology 7, 318-322).

In the context of the present invention: the term "glutamine:fructose 6-phosphate amidotransferase-1 (GFAT-1)" is to be understood as meaning a protein which has the activity of a GFAT and whose activity is inhibited by phosphorylation by a cAMP-dependent protein kinase.

In the context of the present invention, the term "glutamine:fructose 6-phosphate amidotransferase-2 (GFAT-2)" is to be understood as meaning a protein which has the activity of a GFAT and which is activated by phosphorylation by a cAMP-dependent protein kinase.

In the context of the present invention, the term "glutamine:fructose 6-phosphate amidotransferase (GFAT)" is used as a comprehensive term which includes all proteins having the activity of a GFAT. Accordingly, it also comprises proteins referred to in the literature as "glutamine:fructose 6-phosphate amidotransferase-1 (GFAT-1)" or as "glutamine:fructose 6-phosphate amidotransferase-2 (GFAT-2)", but is not limited to these.

In the context of the present invention, the term "increased activity of a protein having the (enzymatic) activity of a GFAT" means an increased expression of endogenous genes coding for proteins having the activity of a GFAT and/or an increased amount of transcripts coding for proteins having the activity of a GFAT and/or an increased amount of protein having the activity of a GFAT in the cells and/or an increased enzymatic activity of proteins having the activity of a GFAT in the cells.

An increased expression can be determined, for example, by measuring the amount of transcripts coding for a protein having the activity of a GFAT, for example by Northern blot analysis or RT-PCR. Here, an increase preferably means an increase in the amount of transcripts compared to corresponding not genetically modified wild-type plant cells or not genetically modified wild-type plants by at least 50%, in particular by at least 70%, preferably by at least 85% and particularly preferably by at least 100%. An increase of the amount of transcripts coding for a protein having the activity of a GFAT also means that plants or plant cells having no detectable amounts of transcripts coding for a protein having the activity of a GFAT have, after genetic modification according to the invention, detectable amounts of transcripts coding for a protein having the activity of a GFAT.

An increase in the amount of protein having the activity of a GFAT resulting in an increased activity of these proteins in the plant cells in question can be determined, for example, by immunological methods, such as Western blot analysis, ELISA (Enzyme Linked Immuno Sorbent Assay) or RIA (Radio Immune Assay). Methods for preparing antibodies reacting specifically with a particular protein, i.e. binding specifically to said protein, are known to the person skilled in the art (see, for example, Lottspeich and Zorbas (Eds.), 1998, Bioanalytik [Bioanalysis], Spektrum akad. Verlag, Heidelberg, Berlin, ISBN 3-8274-0041-4). Some companies (for example Eurogentec, Belgium) offer the preparation of such antibodies as an order service. Here, an increase in the amount of protein preferably means an increase in the amount of protein having an activity of a GFAT compared to corresponding not genetically modified wild-type plant cells or not genetically modified wild-type plants by at least 50%, in particular by at least 70%, preferably by at least 85% and particularly preferably by at least 100%. An increase in the amount of protein having an activity of a GFAT also means that plants or plant cells having no detectable amount of a protein having the activity of a GFAT have, after genetic modification according to the invention, a detectable amount of a protein having the activity of a GFAT.

The increased activity of a protein having the activity of a GFAT in plant extracts can be determined by methods known to the person skilled in the art as described, for example, in Samac et al. (2004, Applied Biochemistry and Biotechnology 113-116, Humana Press, Editor Ashok Mulehandani, 1167-1182, ISSN 0273-2289). A preferred method for determining the amount of the activity of a protein having the activity of a GFAT is given in General Methods, item 5.

An increased amount of (enzymatic) activity of proteins having the activity of a GFAT preferably means an increase of the activity of such proteins by at least 50%, preferably at least 70%, especially preferably by at least 85% and particularly preferably by at least 100% compared to corresponding not genetically modified wild-type plant cells or not genetically modified wild-type plants. An increase in the amount of enzymatic activity of proteins having the activity of a GFAT also means that plants or plant cells having no detectable amount of a protein having the activity of a GFAT have, after genetic modification according to the invention, a detectable amount of a protein having the activity of a GFAT.

In the context of the present invention, the term "genome" is to be understood as meaning the entire genetic material present in a plant cell. It is known to the person skilled in the art that, in addition to the nucleus, other compartments (for example plastids, mitochondria) also contain genetic material.

In the context of the present invention, the term "stably integrated nucleic acid molecule" is to be understood as meaning the integration of a nucleic acid molecule into the genome of the plant. A stably integrated nucleic acid molecule is characterized in that, during the replication of the corresponding integration site, it is multiplied together with the nucleic acid sequences of the host which border on the integration site, so that the integration site in the replicated DNA strand is surrounded by the same nucleic acid sequences as on the read strand which serves as a matrix for the replication.

A large number of techniques for stably integrating nucleic acid molecules into a plant host cell is available. These techniques include the transformation of plant cells with T-DNA using *Agrobacterium tumefaciens* or *Agrobacterium rhizogenes* as means of transformation, protoplast fusion, injection, electroporation of DNA, introduction of DNA by the biolistic approach and also further options (review in "Transgenic Plants", Leandro ed., Humana Press 2004, ISBN 1-59259-827-7). The use of *agrobacterium*-mediated transformation of plant cells has been subject to in-depth studies and has been described exhaustively in EP 120516; Hoekema, IN: The Binary Plant Vector System Offsetdrukkerij Kanters B. V. Alblasserdam (1985), Chapter V; Fraley et al., Crit. Rev. Plant Sci. 4, 1-46 and in An et al. EMBO J. 4, (1985), 277-287. For the transformation of potatoes see, for example, Rocha-Sosa et al., EMBO J. 8, (1989), 29-33), for the transformation of tomato plants see, for example, U.S. Pat. No. 5,565,347.

The transformation of monocotyledonous plants using vectors based on *Agrobacterium* transformation has been described, too (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system for transforming monocotyledonous plants is the transformation using the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), the protoplast transformation, the electroporation of partially permeabilized cells, the introduction of DNA using glass fibers. In particular the transformation of corn has been described several times in the literature (cf., for example, WO95/06128, EP0513849, EP0465875, EP0292435;

Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726). The transformation of other grasses, such as, for example, switchgrass (*Panicum virgatum*) has also been described (Richards et al., 2001, Plant Cell Reporters 20, 48-54).

The successful transformation of other cereal species has also been described, for example for barley (Wan and Lemaux, s.o.; Ritala et al., s.o.; Krens et al., Nature 296, (1982), 72-74) and for wheat (Nehra et al., Plant J. 5, (1994), 285-297; Becker et al., 1994, Plant Journal 5, 299-307). All of the above methods are suitable in the context of the present invention.

Compared to the prior art, genetically modified plant cells according to the invention or genetically modified plants according to the invention offer the advantage that they produce higher amounts of hyaluronan than plants having only the activity of a hyaluronan synthase. This allows hyaluronan to be produced at little expense since the isolation of hyaluronan from plants having a higher hyaluronan content is less complicated and more cost efficient. Furthermore, compared to the plants described in the prior art, smaller cultivation areas are required to produce hyaluronan using the genetically modified plants according to the invention. This leads to the possibility to provide hyaluronan in sufficient amounts even for industrial application where it is currently not used owing to its scarcity and the high price. Virus-infected plant organisms of the genus *Chlorella* are unsuitable for producing relatively large amounts of hyaluronan. In the production of hyaluronan, virus-infected algae have the disadvantage that the genes required for hyaluronan synthesis are not stably integrated into their genome (Van Etten and Meints, 1999, Annu. Rev. Microbiol. 53, 447-494), so that, for producing hyaluronan, the virus infection has to be repeated. Accordingly, it is not possible to isolate individual *Chlorella* cells which synthesize continuously the desired quality and quantity of hyaluronan. Furthermore, in virus-infected *Chlorella* algae, hyaluronan is only produced for a limited period of time, and as a result of the lysis caused by the virus, the algae are killed only about 8 hours after the infection (Van Etten et al., 2002, Arch Virol 147, 1479-1516). In contrast, the present invention offers the advantage that the genetically modified plant cells according to the invention and the genetically modified plants according to the invention can be propagated in an unlimited manner vegetatively or sexually and that they produce hyaluronan continuously.

The transgenic plants described in WO 05 012529, which have a nucleic acid molecule coding for a hyaluronan synthase, synthesize a relatively small amount of hyaluronan. In contrast, the present invention offers the advantage that genetically modified plant cells according to the invention and genetically modified plants according to the invention synthesize considerably higher amounts of hyaluronan.

Accordingly, the present invention also provides genetically modified plant cells according to the invention or genetically modified plants according to the invention which synthesize hyaluronan. Preferably plant cells according to the invention or plants according to the invention synthesize at least 500 µg hyaluronan per gram fresh weight, with preference at least 1500 µg hyaluronan per gram fresh weight, particularly preferable at least 3500 µg hyaluronan per gram fresh weight, especially preferable at least 4000 µg hyaluronan per gram fresh weight an mostly preferable at least 5500 µg hyaluronan per gram fresh weight.

Preferably plant cells according to the invention or plants according to the invention synthesize at most 25000 µg hyaluronan per gram fresh weight, with preference at most 20000 µg hyaluronan per gram fresh weight, particularly preferable at most 15000 µg hyaluronan per gram fresh weight, especially preferable at most 10000 µg hyaluronan per gram fresh weight an mostly preferable at most 6500 µg hyaluronan per gram fresh weight.

It has been observed that, over the development time, hyaluronan accumulates in plant tissue; accordingly, the amount of hyaluronan with respect to the fresh weight or with respect to the dry weight in the genetically modified plant cells according to the invention or in the genetically modified plants according to the invention is to be determined with particular preference during harvesting or (one or two) days before harvesting of the plant cells in question or the plants in question. Here, use is made in particular of plant material (for example tubers, seeds, leaves) with respect to the amount of hyaluronan which is to be used for further processing.

Genetically modified plant cells according to the invention or genetically modified plants according to the invention which synthesize hyaluronan can be identified by isolating the hyaluronan that is synthesized by them and proving its structure.

Since plant tissue has the advantage that it does not contain hyaluronidases, a simple and rapid isolation method can be used for confirming the presence of hyaluronan in genetically modified plant cells according to the invention or genetically modified plants according to the invention. To this end, water is added to the plant tissue to be examined and the plant tissue is then comminuted mechanically (with the aid of, for example, a bead mill, a beater mill, a Warring blender, a juice extractor, etc.). If required, more water may then be added to the suspension, and cell debris and water-insoluble components are then removed by centrifugation or sieving. The presence of hyaluronan in the supernatant obtained after centrifugation can then be demonstrated using, for example, a protein which binds specifically to hyaluronan. A method for detecting hyaluronan with the aid of a protein that binds specifically to hyaluronan is described, for example, in U.S. Pat. No. 5,019,498. Test kits (for example the hyaluronic acid (HA) test kit from Corgenix, Inc., Colorado, USA, Prod. No. 029-001); see also General Methods item 4). In parallel, it is possible to initially digest an aliquot of the centrifugation supernatant obtained with a hyaluronidase and then to confirm the presence of hyaluronan with the aid of a protein that specifically binds to hyaluronan, as described above. By the action of the hyaluronidase in the parallel batch, the hyaluronan present therein is degraded, so that after complete digestion it is no longer possible to detect significant amounts of hyaluronan.

The presence of hyaluronan in the centrifugation supernatant can furthermore also be confirmed using other analysis methods, such as, for example, IR, NMR or mass spectroscopy.

The overexpression, in corn, of a protein having the (enzymatic) activity of a GFAT fused translationally with a plastid signal peptide resulted in an increased UDP-glucosamine content, and the cytosolic overexpression, in corn, of a protein having the (enzymatic) activity of a GFAT resulted in an increased glucosamine 1-phosphate content in ground endosperm tissue. However, UDP-glucosamine and glucosamine 1-phosphate are not substrates for the synthesis of hyaluronan by hyaluronan synthase. Furthermore, it is known that glucosamine has a cytotoxic effect on plant cells (Roberts et al., 1971, Plant Physiol. 48, 36-42) and that, if relatively high concentrations are present in plant cells, it is converted into glucosamine 6-phosphate. Glucosamine 6-phosphate is likewise toxic for plant cells. (WO 98 35047, U.S. Pat. No. 6,444,878). Furthermore, it is known that proteins having the activity of a GFAT can be regulated in an inhibitory manner by metabolites which are formed in the further metabolic path for the synthesis of UDP-N-acetylglucosamine. Proteins having the activity of a GFAT, isolated form eucaryotes (both with animal and plant organisms) are inhibited, for example, by UDP-N-acetylglucosamine, which is one of the two substrates for hyaluronan synthase (Kornfeld, 1967, J. Biol. Chem. 242 (13), 3135-3141; Graack et al., 2001, Biochem. J. 360, 401-412; Mayer et al., 1968, Plant Physiol. 43, 1097-1107). Bacterial proteins having the activity of a GFAT are inhibited by glucosamine 6-phosphate, a direct reaction product of the GFAT-catalyzed reaction (Deng et al., 2005, Metabolic Engineering 7, 201-214).

There are no indications in the literature what may limit the amount of hyaluronan synthesized in plant cells.

Accordingly, it has surprisingly been found that genetically modified plant cells or genetically modified plants having a nucleic acid molecule coding for a hyaluronan synthase and having additionally increased GFAT activity compared to genetically modified plant cells or genetically modified plants having (only) hyaluronan synthase activity produce significantly high amounts of hyaluronan.

In a preferred embodiment, the present invention relates to genetically modified plant cells according to the invention or genetically modified plants according to the invention, characterized in that they produce an increased amount of hyaluronan compared to genetically modified plant cells or compared to genetically modified plants which (only) have the activity of a hyaluronan synthase or compared to genetically modified plant cells or compared to genetically modified plants having the activity of a hyaluronan synthase and no increased activity of a protein having the activity of a GFAT.

In the context of the present invention, the term "plant cell or plant (only) having the activity of a hyaluronan synthase" is to be understood as meaning a genetically modified plant cell or a genetically modified plant where the genetic modification consists in that it comprises a nucleic acid molecule coding for a hyaluronan synthase, compared to corresponding not genetically modified wild-type plant cells or not genetically modified wild-type plants.

In particular, "plant cells or plants (only) having the activity of a hyaluronan synthase" are characterized in that they synthesize hyaluronan and that they have no additional genetic modifications other than the introduction of a nucleic acid molecule coding for a hyaluronan synthase into not genetically modified wild-type plant cells or not genetically modified wild-type plants. Preferably, such plants do not have an increased activity of a protein having the activity of a GFAT.

The amount of hyaluronan produced by plant cells or plants can be determined with the aid of the methods which have already been described above, for example using a commercial test kit (for example the hyaluronic acid (HA) test kit from Corgenix, Inc., Colorado, USA, Prod. No. 029-001). A method which is preferred in the context of the present invention for determining the hyaluronan content in plant cells or plants is described under General Methods, item 4.

In a further embodiment of the present invention, the genetically modified plant cells according to the invention or the genetically modified plants according to the invention are plant cells of a green terrestrial plant or green terrestrial plants, respectively, which synthesize hyaluronan.

In the context of the present invention, the term "green terrestrial plant (Embryophyta)" is to be understood as defined in Strasburger, "Lehrbuch der Botanik" [Textbook of Botany], 34th ed., Spektrum Akad. Verl., 1999, (ISBN 3-8274-0779-6).

A preferred embodiment of the present invention relates to genetically modified plant cells according to the invention of multicellular plants or genetically modified plants according to the invention which are multicellular organisms. Accordingly, this embodiment relates to plant cells or plants which do not originate from single-cell plants (protists) or which are not protists.

The genetically modified plant cells according to the invention or the genetically modified plants according to the invention may, in principle, be plant cells and plants, respectively, of any plant species, i.e. both monocotyledonous and dicotyledonous plants. They are preferably crop plants, i.e. plants cultivated by man for the purpose of feeding man and animal or for producing biomass and/or for preparing substances for technical, industrial purposes (for example corn, rice, wheat, alfalfa, rye, oats, barley, manioc, potato, tomato, switchgrass (*Panicum virgatum*), sago, mung beans, pas, sorghum, carrots, aubergine, radish, oilseed rape, soybeans, peanuts, cucumbers, pumpkins, melons, leek, garlic, cabbage, spinach, sweet potato, asparagus, courgettes, lettuce, artichokes, sweetcorn, parsnip, scorzonera, jerusalem artichoke, banana, sugarbeet, sugarcane, beetroot, broccoli, cabbage, onion, yellow beet, dandelion, strawberry, apple, apricot, plum, peach, grapevines, cauliflower, celery, bell peppers, swede, rhubarb). Particularly preferred are rice, tomato or potato plants.

In a preferred embodiment, the present invention relates to genetically modified plant cells according to the invention or genetically modified plants according to the invention where the nucleic acid molecule coding for hyaluronan synthase is characterized in that it codes for a viral hyaluronan synthase. The nucleic acid molecule coding for the hyaluronan synthase preferably codes for a hyaluronan synthase of a virus which infects algae.

With respect to an algae-infecting virus, the nucleic acid molecule which codes for a hyaluronan synthase preferably codes for a hyaluronan synthase of a *Chlorella*-infecting virus, particularly preferably a hyaluronan synthase of a *Paramecium bursaria Chlorella* Virus 1 and especially preferably a hyaluronan synthase of a *Paramecium bursaria Chlorella* virus of an H1 strain.

In a further preferred embodiment, the present invention relates to genetically modified plant cells according to the invention or genetically modified plants according to the invention where the nucleic acid molecule which codes for the hyaluronan synthase is characterized in that the codons of the nucleic acid molecule coding for a hyaluronan synthase are modified compared to the codons of the nucleic acid molecule coding for the hyaluronan synthase of the organism that the hyaluronan synthase originates from. With particular preference, the codons of the hyaluronan synthase have been modified such that they are adapted to the frequency of the use of the codons of the plant cell or the plant into whose genome they are integrated or to be integrated.

Owing to the degeneration of the genetic code, amino acids can be encoded by one or more codons. In different organisms, the codons coding for an amino acid are used at different frequencies. Adapting the codon of a coding nucleic acid sequence to the frequency of their use in the plant cell or in the plant into whose genome the sequence to be expressed is to be integrated may contribute to an increased amount of translated protein and/or to the stability of the mRNA in question in the particular plant cells or plants. The frequency of use of codons in the plant cells or plants in question can be determined by the person skilled in the art by examining as many coding nucleic acid sequences of the organism in question as possible for the frequency with which certain codons are used for coding a certain amino acid. The frequency of the use of codons of certain organisms is known to the person skilled in the art and can be determined in a simple and rapid manner using computer programs. Suitable computer programs are publicly accessible and provided for free inter alia on the internet (for example Graphic Codon Usage Analyser; Codon Usage Database; and Computational Molecular Biology and Evolutionary Bioinformatics websites). Adapting the codons of a coding nucleic acid sequence to the frequency of their use in the plant cell or in the plant into whose genome the sequence to be expressed is to be integrated can be carried out by in vitro mutagenesis or, preferably, by de novo synthesis of the gene sequence. Methods for the de novo synthesis of nucleic acid sequences are known to the person skilled in the art. A de novo synthesis can be carried out, for example, by initially synthesizing individual nucleic acid oligonucleotides, hybridizing these with oligonucleotides complementary thereto, so that they form a DNA double strand, and then ligating the individual double-stranded oligonucleotides such that the desired nucleic acid sequence is obtained. The de novo synthesis of nucleic acid sequences including the adaptation of the frequency with which the codons are used to a certain target organism can also be sourced out to companies offering this service (for example Entelechon GmbH, Regensburg, Germany).

The nucleic acid molecule coding for the hyaluronan synthase is preferably characterized in that it codes for a hyaluronan synthase whose amino acid sequence is at least 70%, preferably at least 80%, with preference at least 90%, especially preferably at least 95% and most preferably at least 98% identical to the amino acid sequence shown under SEQ ID NO 2. In a particularly preferred embodiment, the nucleic acid molecule coding for the hyaluronan synthase is characterized in that it codes for a hyaluronan synthase having the amino acid sequence shown under SEQ ID No 2.

In a further embodiment, the nucleic acid molecule coding for a hyaluronan synthase is at least 70%, preferably at least 80%, with preference at least 90%, especially preferably at least 95% and most preferably at least 98% identical to the nucleic acid sequence shown under SEQ ID NO 1 or SEQ ID NO 3. In a particularly preferred embodiment, the nucleic acid molecule coding for the hyaluronan synthase is characterized in that it has the nucleic acid sequence shown under SEQ ID No 3.

On Aug. 25, 2004, the plasmid IC 341-222, comprising a synthetic nucleic acid molecule coding for a *Paramecium bursaria Chlorella* virus hyaluronan synthase was deposited at the Deutsche Sammiung von Mikroorganismen und Zellkulturen GmbH, Mascheroder Weg 1b, 38124 Brunswick, Germany, under the number DSM16664, in accordance with the Budapest treaty. The amino acid sequence shown in SEQ ID NO 2 can be derived from the coding region of the nucleic acid sequence integrated into the plasmid IC 341-222 and codes for a *Paramecium bursaria Chlorella* virus hyaluronan synthase.

Accordingly, the present invention also relates to genetically modified plant cells according to the invention or genetically modified plants according to the invention where the nucleic acid molecule which codes for the hyaluronan synthase is characterized in that it codes for a protein whose amino acid sequence can be derived from the coding region of the nucleic acid sequence inserted into plasmid DSM16664 or that it codes for a protein whose amino acid sequence is at least 70%, preferably at least 80%, with preference at least 90%, especially preferably at least 95% and most preferably at least 98% identical to the amino acid sequence which can be derived from the coding region of the nucleic acid sequence inserted into plasmid DSM16664.

The present invention also relates to genetically modified plant cells according to the invention or genetically modified plants according to the invention where the nucleic acid molecule coding for hyaluronan synthase is characterized in that it is the hyaluronan-synthase-encoding nucleic acid sequence integrated into plasmid DSM16664 or that it is at least 70%, preferably at least 80%, with preference at least 90%, especially preferably at least 95% and most preferably at least 98% identical to the nucleic acid sequence integrated into plasmid DSM16664.

The present invention furthermore relates to genetically modified plant cells according to the invention or genetically modified plants according to the invention which are characterized in that they have a foreign nucleic acid molecule stably integrated into their genome, said foreign nucleic acid molecule increasing the activity of a protein having the activity of a GFAT compared to corresponding not genetically modified wild-type plant cells or corresponding not genetically modified wild-type plants.

In the context of the present invention, the term "foreign nucleic acid molecule" is to be understood as meaning a molecule which either does not naturally occur in the corresponding wild-type plant cells or which does not naturally occur in the concrete spatial arrangement in wild-type plant cells or which is localized at a site in the genome of the wild-type plant cell where it does not naturally occur. Preferably, the foreign nucleic acid molecule is a recombinant molecule comprising various elements whose combination or specific spatial arrangement does not naturally occur in plant cells.

In the context of the present invention, the term "recombinant nucleic acid molecule" is to be understood as meaning a nucleic acid molecule which has various nucleic acid molecules which are not naturally present in a combination like that present in a recombinant nucleic acid molecule. Thus, recombinant nucleic acid molecules may, in addition to nucleic acid molecules coding for a hyaluronan synthase and/or a protein having the activity of a GFAT, additionally have nucleic acid sequences which are not naturally present in combination with the nucleic acid molecules mentioned. The additional nucleic acid sequences mentioned which are present on a recombinant nucleic acid molecule in combination with a nucleic acid molecule encoding for a hyaluronan synthase or a protein having the activity of a GFAT may be any sequences. For example, they may be genomic plant nucleic acid sequences. The additional nucleic acid sequences are preferably regulatory sequences (promoters, termination signals, enhancers), particularly preferably regulatory sequences which are active in plant tissue, especially preferably tissue-specific regulatory sequences which are active in plant tissue. Methods for generating recombinant nucleic acid molecules are known to the person skilled in the art and comprise genetic engineering methods, such as, for example, linking of nucleic acid molecules by ligation, genetic recombination or the de novo synthesis of nucleic acid molecules (see, for example, Sambrok et al., Molecular Cloning, A Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929).

Genetically modified plant cells and genetically modified plants having a foreign nucleic acid molecule stably integrated into their genome or a plurality of foreign nucleic acid molecules stably integrated into their genome which code for hyaluronan synthase and which increase the activity of a protein having the activity of a GFAT compared to corresponding not genetically modified wild-type plant cells or not genetically modified wild-type plants can be distinguished from said wild-type plant cells and said wild-type plants, respectively, inter alia by the fact that they comprise a foreign nucleic acid molecule which does not naturally occur in wild-type plant cells and wild-type plants, respectively, or in that such a molecule is integrated at a site in the genome of the genetically modified plant cell according to the invention or in the genome of the genetically modified plant according to the invention where it does not occur in wild-type plant cells and wild-type plants, respectively, i.e. in a different genomic environment. Furthermore, such genetically modified plant cells according to the invention and genetically modified plants according to the invention can be distinguished from not genetically modified wild-type plant cells and not genetically modified wild-type plants, respectively, in that they comprise at least one copy of the foreign nucleic acid molecule stably integrated into their genome, if appropriate in addition to copies of such a molecule naturally present in the wild-type plant cells or wild-type plants. If the foreign nucleic acid molecule(s) introduced into the genetically modified plant cells according to the invention or the genetically modified plant according to the invention are additional copies of molecules already naturally present in the wild-type plant cells or the wild-type plants, the genetically modified plant cells according to the invention and the genetically modified plants according to the invention can be distinguished from wild-type plant cells and wild-type plants, respectively, in particular by the fact that this additional copy/these additional copies is/are localized at sites in the genome where it/they is/are not present in wild-type plant cells and wild-type plants, respectively.

The stable integration of a nucleic acid molecule into the genome of a plant cell or a plant can be demonstrated by genetic methods and/or methods of molecular biology. A stable integration of a nucleic acid molecule into the genome of a plant cell or the genome of a plant is characterized in that in the progeny which has inherited said nucleic acid molecule, the stably integrated nucleic acid molecule is present in the same genomic environment as in the parent generation. The presence of a stable integration of a nucleic acid sequence in the genome of a plant cell or in the genome of a plant can be demonstrated using methods known to the person skilled in the art, inter alia with the aid of Southern blot analysis of the RFLP analysis (Restriction Fragment Length Polymorphism) (Nam et al., 1989, The Plant Cell 1, 699-705; Leister and Dean, 1993, The Plant Journal 4 (4), 745-750), with methods based on PCR, such as, for example, the analysis of differences in length in the amplified fragments (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160) or using amplified fragments cleaved using restriction endonucleases (Cleaved Amplified Polymorphic Sequences, CAPS) (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753).

In principle, the foreign nucleic acid molecule may be any nucleic acid molecule which increases, in the plant cell or plant, the activity of a protein having the activity of a GFAT.

In the context of the present invention, genetically modified plant cells according to the invention and genetically modified plants according to the invention can also be prepared by using insertion mutagenesis (review: Thorneycroft et al., 2001, Journal of experimental Botany 52 (361), 1593-1601). In the context of the present invention, insertion mutagenesis is to be understood as meaning in particular the insertion of transposons or transfer DNA (T-DNA) into a gene or into the vicinity of a gene coding for a protein having the activity of a GFAT, thus increasing the activity of a protein having the activity of a GFAT in the cell in question.

The transposons may either be transposons which occur naturally in the cell (endogenous transposons) or those which are not naturally present in said cell but were introduced into the cell by genetic engineering, such as, for example, transformation of the cell (heterologous transposons). The modification of the expression of genes by transposons is known to the person skilled in the art. A review of the use of endogenous and heterologous transposons as tools in plant biotechnology is given in Ramachandran and Sundaresan (2001, Plant Physiology and Biochemistry 39, 234-252).

T-DNA insertion mutagenesis is based on the fact that certain sections (T-DNA) of Ti plasmids from *Agrobacterium* can be integrated into the genome of plant cells. The site of integration into the plant chromosome is not predetermined, integration can be in any location. If the T-DNA is integrated into a section or into the vicinity of a section of the chromosome representing a gene function, this may result in an increased gene expression and thus also a change in the activity of the protein encoded by the gene in question.

The sequences inserted into the genome (in particular transposons or T-DNA) are characterized in that they comprise sequences resulting in the activation of regulatory sequences of a gene coding for a protein having the activity of a GFAT ("activation tagging"). Preferably, the sequences inserted into the genome (in particular transposons or T-DNA) are characterized in that they are integrated into the vicinity of endogenous nucleic acid molecules in the genome of the plant cell or the plant coding for a protein having the activity of a GFAT.

Genetically modified plant cells according to the invention and genetically modified plants according to the invention can be generated, for example, using the method of activation tagging (see, for example, Walden et al., Plant J. (1991), 281-288; Walden et al., Plant Mol. Biol. 26 (1994), 1521-1528). This method is based on the activation of endogenous promoters by enhancer sequences, such as, for example, the enhancer of the 35S RNA promoter of the cauliflower mosaic virus or the octopine synthase enhancer.

In the context of the present invention, the term "T-DNA activation tagging" is to be understood as meaning a T-DNA fragment which comprises enhancer sequences and, by integration into the genome of a plant cell, increases the activity of a protein having the activity of a GFAT.

In the context of the present invention, the term "transposon activation tagging" is to be understood as meaning a transposon which comprises enhancer sequences and, by integration into the genome of a plant cell, increases the activity of a protein having the activity of a GFAT.

A preferred embodiment of the present invention relates to genetically modified plant cells according to the invention or genetically modified plants according to the invention which are characterized in that at least one foreign nucleic acid molecule codes for a protein having the (enzymatic) activity of a GFAT.

A particularly preferred embodiment of the present invention relates to genetically modified plant cells according to the invention or genetically modified plants according to the invention which are characterized in that a foreign nucleic acid molecule codes for a protein having the (enzymatic) activity of a GFAT.

According to the invention, the foreign nucleic acid molecule coding for a protein having the (enzymatic) activity of a GFAT may originate from any organism; preferably, said nucleic acid molecule originates from bacteria, fungi, animals, plants or viruses, particularly preferably from mammals, plants or bacteria and especially preferably from the mouse or *Escherichia coli*.

With respect to viruses, the foreign nucleic acid molecule coding for a protein having the (enzymatic) activity of a GFAT preferably originates from a virus which infects algae, with preference from a virus which infects algae of the genus *Chlorella*, particularly preferably from a *Paramecium bursaria Chlorella* virus and especially preferably from a *Paramecium bursaria Chlorella* virus of an H1 strain.

Instead of the naturally occurring nucleic acid molecule coding for a protein having the (enzymatic) activity of a GFAT, it is also possible for a nucleic acid molecule generated by mutagenesis to be introduced into the genetically modified plant cells according to the invention or the genetically modified plants according to the invention, where said mutagenized foreign nucleic acid molecule is characterized in that it codes for a protein having the (enzymatic) activity of a GFAT with reduced inhibition by metabolites (for example of the glucosamine metabolism). The preparation of such mutagenized nucleic acid molecules is described in an exemplary manner for a protein having the (enzymatic) activity of a GFAT from *Escherichia coli* in Deng et al. (2005, Metabolic Engineering 7, 201-214; WO 04 003175). Mutants for a protein having the activity of a GFAT from the mouse are described, for example, in Hu et al. (2004, J. Biol. Chem. 279 (29), 29988-29993).

Nucleic acid molecules coding for a protein having the activity of a GFAT are known to the person skilled in the art and described in the literature. Thus, nucleic acid molecules coding for a protein having the activity of a GFAT are described from viruses, for example for the *Chlorella* virus k2 (EMBL acc No AB107976.1), from bacteria, for example for *Escherichia coli* (Dutka-Malen, 1988, Biochemie 70 (2), 287-290; EMBL acc No: L10328.1), from fungi, for example for *Saccharomyces cerevisiae* (EMBL acc No AF334737.1. Watzele et al., 1989, J. Biol. Chem. 264, 8753-8758), *Aspergillus niger* (EMBL acc No AY594332.1), *Candida albicans* (EMBL acc No X94753.1), from insects, for example for *Aedes aegyti* (Kato et al., 2002, Insect. Biol. 11 (3), 207,216; EMBL acc No AF399922.1), *Drosophila melanogaster* (GFAT-1: EMBL acc No Y18627.1, GFAT-2: NCBI acc No NM_143360.2), from algae for *Volvariella volvacea* (EMBL acc No AY661466.1), from vertebrates for example for *Homo sapiens* (GFAT-1: EMBL acc No AF334737.1; GFAT-2: NCBI acc No BC000012.2. Oki et al., 1999, Genomics 57 (2), 227-34), *Mus musculus* (GFAT-1: EMBL acc No AF334736.1; GFAT-2: EMBL acc No AB016780.1), or from plants for example for *Arabidopsis thaliana* (EMBL acc No AP001297.1; cds NCBI acc No BAB03027.1).

In a preferred embodiment, the present invention relates to genetically modified plant cells according to the invention and genetically modified plants according to the invention where the foreign nucleic acid molecule coding for a protein having the activity of a GFAT is selected from the group consisting of a) nucleic acid molecules coding for a protein having the amino acid sequence given under SEQ ID NO 5 or a protein having the amino acid sequence given under SEQ ID NO 7 or a protein having the amino acid sequence given under SEQ ID NO 9;

b) nucleic acid molecules coding for a protein whose sequence is at least 60%, preferably at least 80%, with preference at least 90%, especially preferably at least 95% and most preferably at least 98% identical to the amino acid sequence given under SEQ ID NO 5, under SEQ ID NO 7 or under SEQ ID NO 9;

c) nucleic acid molecules comprising the nucleotide sequence shown under SEQ ID NO 4 or a sequence complementary thereto, the nucleotide sequence shown under SEQ ID NO 6 or a sequence complementary thereto, the nucleotide sequence shown under SEQ ID NO 8 or a sequence complementary thereto or the nucleotide sequence shown under SEQ ID NO 10 or a sequence complementary thereto;

d) nucleic acid molecules which are at least 70%, preferably at least 80%, with preference at least 90%, especially preferably at least 95% and most preferably at least 98% identical to the nucleic acid sequences described under a) or c);

e) nucleic acid molecules which hybridize under stringent conditions with at least one strand of the nucleic acid sequences described under a) or c);

f) nucleic acid molecules whose nucleotide sequence differs from the sequence of the nucleic acid molecules mentioned under a) or c) owing to the degeneration of the genetic code; and g) nucleic acid molecules which are fragments, allelic variants and/or derivatives of the nucleic acid molecules mentioned under a), b), c), d), e) or f).

In the context of the present invention, the term "hybridization" means a hybridization under conventional hybridization conditions, preferably under stringent conditions, as described, for example, in Sambrock et al., Molecular Cloning, A Laboratory Manual, 2 ed. (1989) Cold Spring Harbor Laboratory Press, Cold Spring Harbor, N.Y.). With particular preference, "hybridization" means a hybridization under the following conditions:

Hybridization Buffer:
2×SSC; 10×Denhardt solution (Fikoll 400+PEG+BSA; ratio 1:1:1); 0.1% SDS; 5 mM EDTA; 50 mM Na2HPO4; 250 µg/ml of herring sperm DNA; 50 µg/ml of tRNA; or 25 M sodium phosphate buffer pH 7.2; 1 mM EDTA; 7% SDS Hybridization Temperature:
T=65 to 68° C.
Wash buffer: 0.1×SSC; 0.1% SDS
Wash temperature: T=65 to 68° C.

Nucleic acid molecules which hybridize with nucleic acid molecules coding for a protein having the activity of a GFAT may originate from any organism; accordingly, they may originate from bacteria, fungi, animals, plants or viruses.

Nucleic acid molecules hybridizing with nucleic acid molecules coding for protein having the activity of a GFAT particularly preferably originate from mammals, plants or bacteria and especially preferably from the mouse or *Escherichia coli*.

Nucleic acid molecules hybridizing with nucleic acid molecules coding for protein having the activity of a GFAT-1 or a GFAT-2 preferably originate from a eucaryotic organism, particularly preferably they originate from an animal organism, especially preferably from the mouse.

Nucleic acid molecules which hybridize with the molecules mentioned may be isolated, for example, from genomic or from cDNA libraries. Such nucleic acid molecules can be identified and isolated using the nucleic acid molecules mentioned or parts of these molecules or the reverse complements of these molecules, for example by hybridization according to standard methods (see, for example, Sambrook et al., 1989, Molecular Cloning, A Laboratory Manual, 2 ed. Cold Spring Harbor Laboratory Press, Cold Spring Harbor, N.Y.) or by amplification using PCR.

As hybridization sample for isolating a nucleic acid sequence coding for a protein having the activity of a GFAT or the activity of a GFAT-1 or the activity of a GFAT-2, it is possible to use, for example, nucleic acid molecules having exactly or essentially the nucleotide sequence given under SEQ ID NO 4 or under SEQ ID NO 6 or under SEQ ID NO 8 or under SEQ ID NO 10, or parts of these sequences.

The fragments used as hybridization samples may also be synthetic fragments or oligonucleotides prepared using the customary synthesis techniques, whose sequence is essentially identical to the nucleic acid molecule described in the context of the present invention. Once genes which hybridize with the nucleic acid sequences described in the context of the present invention are identified and isolated, the sequence should be determined and the properties of the proteins coded for by this sequence should be analyzed to determine whether they are proteins having the activity of a GFAT. Methods of how to determine whether a protein has the activity of a protein having the activity of a GFAT (for example Mayer et al., 1968, Plant Physiol. 43, 1097-1107; Deng et al., 2005, Metabolic Engineering 7, 201-214), a GFAT-1 or a GFAT-2 (for example Hu et al., 2004, J. Biol. Chem. 279 (29), 29988-29993) are known to the person skilled in the art and described, inter alia, in the literature mentioned.

The molecules hybridizing with the nucleic acid molecules described in the context of the present invention comprise in particular fragments, derivatives and allelic variants of the nucleic acid molecules mentioned. In the context of the present invention, the term "derivative" means that the sequences of these molecules differ in one or more positions from the sequences of the nucleic acid molecules described above and are highly identical to these sequences. The differences to the nucleic acid molecules described above may, for example, be due to deletion (in particular 5'- and/or 3'-deletions, leading to N- and/or C-terminal deletions of the corresponding protein), addition, substitution, insertion or recombination.

In the context of the present invention, the term "identity" means a sequence identity over the entire length of the coding region of a nucleic acid molecule or the entire length of an amino acid sequence coding for a protein of at least 60%, in particular in identity of at least 70%, preferably of at least 80%, particularly preferably of at least 90% and especially preferably of at least 95% and most preferably at least 98%. In the context of the present invention, the term "identity" is to be understood as meaning the number of identical amino acids/nucleotides (identity) with other proteins/nucleic acids, expressed in percent. Preferably, the identity with respect to a protein having the activity of a GFAT is determined by comparison with the amino acid sequence of SEQ ID NO 5 or SEQ ID NO 7 or SEQ ID NO 9 and the identity with respect to a nucleic acid molecule coding for a protein having the activity of a GFAT is determined by comparison with the nucleic acid sequence of SEQ ID NO 4 or SEQ ID NO 6 or SEQ ID NO 8 or SEQ ID NO 10 with other proteins/nucleic acids with the aid of computer programs. If sequences to be compared with one another are of different lengths, the identity is to be determined by determining the identity in percent of the number of amino acids which the shorter sequence shares with the longer sequence. Preferably, the identity is determined using the known and publicly available computer program ClustalW (Thompson et al., Nucleic Acids Research 22 (1994), 4673-4680). ClustalW is made publicly available by Julie Thompson and Toby Gibson, European Molecular Biology Laboratory, Meyerhofstrasse 1, D 69117 Heidelberg, Germany. ClustalW can also be down-loaded from various internet pages, inter alia from IGBMC (Institut de Genetique et de Biologie Moleculaire et Cellulaire, B.P.163, 67404 Illkirch Cedex, France and from EBI and all mirrored internet pages of the EBI (European Bioinformatics Institute, Wellcome Trust Genome Campus, Hinxton, Cambridge CB10 1SD, UK).

Preferably, use is made of the ClustalW computer program of version 1.8 to determine the identity between proteins described in the context of the present invention and other proteins. Here, the parameters have to be set as follows: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS (OFF), NOPGAP, NOHGAP.

Preferably, use is made of the ClustalW computer program of version 1.8 to determine the identity for example between the nucleotide sequence of the nucleic acid molecules described in the context of the present invention and the nucleotide sequence of other nucleic acid molecules. Here, the parameters have to be set as follows: KTUPLE=2, TOPDIAGS=4, PAIRGAP=5, DNAMATRIX:IUB, GAPOPEN=10, GAPEXT=5, MAXDIV=40, TRANSITIONS: unweighted.

Identity furthermore means that there is a functional and/or structural equivalence between the nucleic acid molecules in question or the proteins encoded by them. The nucleic acid molecules which are homologous to the molecules described above and represent derivatives of these molecules are generally variations of these molecules which represent modifications having the same biological function. They may be either naturally occurring variations, for example sequences from other species, or mutations, where these mutations may have occurred in a natural manner or were introduced by targeted mutagenesis. Furthermore, the variations may be synthetically produced sequences. The allelic variants may be either naturally occurring variants or synthetically produced variants or variants generated by recombinant DNA techniques. A special form of derivatives are, for example, nucleic acid molecules which differ from the nucleic acid molecules described in the context of the present invention owing to the degeneration of the genetic code.

The various derivatives of the nucleic acid molecules coding for a protein having the activity of a GFAT have certain common characteristics.

These may, for example, be biological activity, substrate specificity, molecular weight, immunological reactivity, conformation, etc., and also physical properties, such as, for example, the mobility properties in gel electrophoresis, chromatographic behavior, sedimentation coefficients, solubility, spectroscopic properties, stability, pH optimum, temperature optimum, etc. Preferred properties of proteins having the activity of a GFAT are known to the person skilled in the art, have already been mentioned above and are to apply here in an analogous manner.

In a further preferred embodiment, the present invention relates to genetically modified plant cells according to the invention or genetically modified plants according to the invention where nucleic acid molecules coding for a protein having the (enzymatic) activity of a GFAT are characterized in that the codons of said nucleic acid molecules are different from the codons of the nucleic acid molecules which code for said protein having the (enzymatic) activity of a GFAT of the parent organism. Particularly preferably, the codons of the nucleic acid molecules coding for a protein having the (enzymatic) activity of a GFAT are changed thus that they are adapted to the frequency of use of the codons of the plant cell or the plant into whose genome they are integrated or to be integrated.

The present invention furthermore provides genetically modified plant cells according to the invention or genetically modified plants according to the invention characterized in that the foreign nucleic acid molecules stably integrated into the genome of the plant cell or the plant encoding for a hyaluronan synthase and/or coding for a protein having the (enzymatic) activity of a GFAT are linked to regulatory elements initiating the transcription in plant cells (promoters). These may be homologous or heterologous promoters. The promoters can be constitutive, tissue-specific, development-specific or regulated by external factors (for example after application of chemical substances, by action of abiotic factors, such as heat and/or cord, draught, disease, etc.). Here, nucleic acid molecules coding for a hyaluronan synthase or a protein having the (enzymatic) activity of a GFAT, which nucleic acid molecules are integrated into the genome of a genetically modified plant cell according to the invention or a genetically modified plant according to the invention, may in each case be linked to the same promoter, or the individual sequences may be linked to different promoters.

A preferred embodiment of the present invention relates to genetically modified plant cells according to the invention or genetically modified plants according to the invention where at least one foreign nucleic acid molecule, particularly preferably at least two foreign nucleic acid molecules, especially preferably three foreign nucleic acid molecules selected from the group consisting of nucleic acid molecules coding for a hyaluronan synthase or a protein having the (enzymatic) activity of a GFAT is (are) linked to a tissue-specific promoter. Preferred tissue-specific promoters are promoters which initiate transcription specifically in plant tuber, fruit or seed cells or leaves.

To express nucleic acid molecules coding for a hyaluronan synthase or a protein having the (enzymatic) activity of a GFAT, these are preferably linked to regulatory DNA sequences ensuring the transcription in plant cells. These include in particular promoters. In general, any promoter active in plant cells is suitable for the expression.

Here, the promoter may be chosen such that expression is constitutively or only in a certain tissue, at a certain point of the development of the plant or at a point of time determined by external factors. Both in respect to the plant and in respect of the nucleic acid molecule to be expressed, the promoter may be homologous or heterologous.

Suitable promoters are, for example, the promoter of 35S RNS of the cauliflower mosaic virus or the ubiquitin promoter from corn or the Cestrum YLCV (Yellow Leaf Curling Virus; WO 01 73087; Stavolone et al., 2003, Plant Mol. Biol. 53, 703-713) for a constitutive expression, the patatingen promoter B33 (Rocha-Sosa et al., EMBO J. 8 (1989), 23-29) for a tuber-specific expression in potatoes or a fruit-specific promoter for tomato, such as, for example, the polygalacturonase promoter from tomato (Montgomery et al., 1993, Plant Cell 5, 1049-1062) or the E8 promoter from tomato (Metha et al., 2002, Nature Biotechnol. 20(6), 613-618) or the ACC oxidase promoter from peach (Moon and Callahan, 2004, J. Experimental Botany 55 (402), 1519-1528) or a promoter which ensures expression only in photosynthetically active tissues, for example the ST-LS1 promoter (Stockhaus et al., Proc. Natl. Acad. Sci. USA 84 (1987), 7943-7947; Stockhaus et al., EMBO J. 8 (1989), 2445-2451) or for an endosperm-specific expression the HMWG promoter from wheat, the USP promoter, the phaseolin promoter, promoters of zein genes from corn (Pedersen et al., Cell 29 (1982), 1015-1026; Quatroccio et al., Plant Mol. Biol. 15 (1990), 81-93), the glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218), the shrunken-1 promoter (Werr et al., EMBO J. 4 (1985), 1373-1380), a globulin promoter (Nakase et al., 1996, Gene 170(2), 223-226) or a prolamin promoter (Qu und Takaiwa, 2004, Plant Biotechnology Journal 2(2), 113-125). However, it is also possible to use promoters which are only active at a point in time determined by external factors (see, for example, WO 9307279). Of particular interest here may be promoters of heat-shock proteins which permit a simple induction. It is furthermore possible to use seed-specific promoters, such as, for example, the USP promoter from *Vicia faba* which ensures a seed-specific expression in *Vicia faba* and other plants (Fiedler et al., Plant Mol. Biol. 22 (1993), 669-679; Bätumlein et al., Mol. Gen. Genet. 225 (1991), 459-467).

The use of promoters present in the genome of algae-infecting viruses are also suitable for expressing nucleic acid sequences in plants (Mitra et al., 1994, Biochem. Biophys Res Commun 204(1), 187-194; Mitra and Higgins, 1994, Plant Mol Biol 26(1), 85-93, Van Etten et al., 2002, Arch Virol 147, 1479-1516).

In the context of the present invention, the term "tissue specific" is to be understood as meaning the substantial limitation of a manifestation (for example initiation of transcription) to a certain tissue.

In the context of the present invention, the terms "tuber, fruit or seed cell" are to be understood as meaning all cells present in a tuber, a fruit or in a seed.

In the context of the present invention, the term "homologous promoter" is to be understood as meaning a promoter which is naturally present in plant cells or plants used for the preparation of genetically modified plant cells according to the invention or genetically modified plants according to the invention (homologous with respect to the plant cell or the plant) or as meaning a promoter which regulates the regulation of the expression of a gene in the organism from which the sequence was isolated (homologous with respect to the nucleic acid molecule to be expressed).

In the context of the present invention, the term "heterologous promoter" is to be understood as meaning a promoter which is not naturally present in plant cells or plants used for the preparation of genetically modified plant cells according to the invention or genetically modified plants according to the invention (heterologous with respect to the plant cell or plant) or as meaning a promoter which is, in the organism from which a nucleic acid sequence to be expressed was isolated, not naturally present for regulating the expression of said nucleic acid sequence (heterologous with respect to the nucleic acid molecule to be expressed).

Also present may be a termination sequence (polyadenylation signal) which serves to add a poly-A tail to the transcript. The poly-A tail is thought to act in stabilizing the transcripts. Such elements are described in the literature (cf. Gielen et al., EMBO J. 8 (1989), 23-29) and can be exchanged as desired.

It is also possible for intron sequences to be present between the promoter and the coding region. Such intron sequences may lead to stability of expression and in increased expression in plants (Callis et al., 1987, Genes Devel. 1, 1183-1200; Luehrsen, and Walbot, 1991, Mol. Gen. Genet. 225, 81-93; Rethmeier et al., 1997; Plant Journal 12(4), 895-899; Rose and Beliakoff, 2000, Plant Physiol. 122 (2), 535-542; Vasil et al., 1989, Plant Physiol. 91, 1575-1579; X U et al., 2003, Science in China Series C Vol. 46 No. 6, 561-569). Suitable intron sequences are, for example, the first intron of the sh1 gene from corn, the first intron of the poly-ubiquitin gene 1 from corn, the first intron of the EPSPS gene from rice or one of the first two introns of the PAT1 gene from *Arabidopsis*.

The present invention also relates to plants comprising genetically modified plant cells according to the invention. Such plants may be produced by regeneration from genetically modified plant cells according to the invention.

The present invention also relates to processible or consumable parts of genetically modified plants according to the invention comprising genetically modified plant cells according to the invention.

In the context of the present invention, the term "processible parts" is to be understood as meaning plant parts which are used for preparing foodstuff or feedstuff, which are used as a raw material source for industrial processes, as a raw material source for the preparation of pharmaceutical products or as a raw material source for the preparation of cosmetic products.

In the context of the present invention, the term "consumable parts" is to be understood as meaning plant parts which serve as food for man or are used as animal feed.

The present invention also relates to a propagation material of genetically modified plants according to the invention comprising a genetically modified plant cell according to the invention.

Here, the term "propagation material" comprises those components of the plant which are suitable for generating progeny via the vegetative or generative route. Suitable for vegetative propagation are, for example, cuttings, callus cultures, rhizomes or tubers. Other propagation material includes, for example, fruits, seeds, seedling, protoplasts, cell cultures, etc. The propagation material preferably takes the form of tubers, fruits or seeds.

In a further embodiment, the present invention relates to harvestable plant parts of genetically modified plants according to the invention, such as fruits, storage and other roots, flowers, buds, shoots, leaves or stalks, preferably seeds, fruits or tubers, these harvestable parts comprising genetically modified plant cells according to the invention.

Preferably, the present invention relates to propagation material according to the invention or harvestable parts of plants according to the invention comprising hyaluronan. Particularly preferred is propagation material according to the invention or harvestable parts of plants according to the invention which synthesize hyaluronan.

In the context of the present invention, the term "potato plant" or potato" is to be understood as meaning plant species of the genus *Solanum*, particularly tuber-producing species of the genus *Solanum* and in particular *Solanum tuberosum*.

In the context of the present invention, the term "tomato plant" or "tomato" is to be understood as meaning plant species of the genus *Lycopersicon*, in particular *Lycopersicon esculentum*.

The further advantage of the present invention is that harvestable parts, propagation material, processible parts or consumable parts of genetically modified plants according to the invention comprise more hyaluronan than hyaluronan-synthesizing transgenic plants described in the literature. Accordingly, genetically modified plants according to the invention are not only particularly suitable for use as raw material from which hyaluronan may be isolated but can also be used directly as foodstuff/feedstuff or for preparing foodstuff/feedstuff having a prophylactic or therapeutic character (for example for osteoarthritis prophylaxis, U.S. Pat. No. 6,607,745). Since genetically modified plants according to the invention have a higher hyaluronan content than the plants described in the literature, the preparation of such foodstuff/feedstuff requires lower amounts of harvestable parts, propagation material, processible parts or consumable parts of genetically modified plants according to the invention. If consumable parts of genetically modified plants according to the invention are consumed, for example, directly as a so-called "nutraceutical", it is possible to achieve a positive effect even by ingesting relatively small amounts of substance. This may be of particular significance inter alia in the production of animal feed, since animal feed having too high a content of plant components is unsuitable as feedstuff for various animal species.

By virtue of the high capacity of hyaluronan to bind water, harvestable parts, propagation material, processible parts or consumable parts of genetically modified plants according to the invention furthermore have the advantage that less thickeners are required when solidified foodstuff/feedstuff is produced. Thus, for example, the production of jelly requires less sugar, which is associated with an additional positive effect on health. In the production of foodstuff/feedstuff requiring the dehydration of the crude plant material, the advantage of using harvestable parts, propagation material, processible parts or consumable parts of genetically modified plants according to the invention consists in the fact that less water has to be removed from the plant material in question, resulting in lower production costs and, owing to more gentle preparation methods (for example lower and/or shorter input of heat), an elevated nutritional value of the foodstuff/feedstuff in question. Thus, for example, in the production of tomato ketchup less energy has to be introduced in order to achieve the desired consistency.

The present invention furthermore provides a process for preparing a plant which synthesizes hyaluronan, which comprises
a) genetically modifying a plant cell, where the genetic modification comprises steps i to ii below
  i) introduction of a foreign nucleic acid molecule encoding for a hyaluronan synthase into the plant cell
  ii) introduction of a genetic modification into the plant cell, the genetic modification resulting in an increase of the activity of a protein having the (enzymatic) activity of a GFAT compared to corresponding not genetically modified wild-type plant cells
where steps i to ii can be carried out in any order, individually, or any combinations of steps i to ii can be carried out simultaneously b) regenerating a plant from plant cells from step a);
c) generating, if appropriate, further plants using the plants according to step b), where, if appropriate, plant cells are isolated from plants according to step b) and the process steps a) to c) are repeated until a plant is generated which has a foreign nucleic acid molecule coding for a hyaluronan synthase and has an increased activity of a protein having the (enzymatic) activity of a GFAT compared to corresponding not genetically modified wild-type plant cells.

The present invention preferably relates to processes for preparing a plant which synthesizes hyaluronan which comprises
a) genetically modifying a plant cell, where the genetic modification comprises steps i to ii below in any order, or any combinations of steps i to ii may be carried out individually or simultaneously,
  i) introduction of a foreign nucleic acid molecule encoding for a hyaluronan synthase into the plant cell
  ii) introduction of a genetic modification into the plant cell, the genetic modification resulting in an increase of the activity of a protein having the (enzymatic) activity of a GFAT compared to corresponding not genetically modified wild-type plant cells
b) regenerating a plant from plant cells comprising the genetic modification according to steps
  i) a) i
  ii) a) ii
  iii) a) i and a) ii,
c) introducing into plant cells of plants according to step
  i) b) i a genetic modification according to step a) ii,
  ii) b) ii a genetic modification according to step a) i, and regenerating a plant
d) generating, if appropriate, further plants with the aid of the plants obtained according to any of steps b) iii or c) i or c) ii.

The genetic modifications introduced according to step a) into the plant cell may in principle be any type of modification resulting in an increased activity of a protein having the (enzymatic) activity of a GFAT.

The regeneration of the plants according to step b) and, if appropriate, step c) of the processes according to the invention can be carried out using methods known to the person skilled in the art (described, for example, in "Plant Cell Culture Protocols", 1999, edited by R. D. Hall, Humana Press, ISBN 0-89603-549-2).

The generation of further plants (depending on the process according to step c) or step d)) of the processes according to the invention can be carried out, for example, by vegetative propagation (for example via cuttings, tubers or via callus culture and regeneration of intact plants) or via generative propagation. In this context, generative propagation generally takes place under controlled conditions, i.e. selected plants with specific characteristics are hybridized with one another and multiplied. The generation preferably takes place in such a manner that the further plants (depending on the process generated according to step c) or step d)) comprise the modifications introduced in the preceding steps.

In processes according to the invention for preparing plants which synthesize hyaluronan, the genetic modifications for generating the genetically modified plant cells according to the invention can be carried out simultaneously or in successive steps. Here, it is immaterial whether the same method as for the genetic modification introducing a foreign nucleic acid molecule coding for a hyaluronan synthase into the plant cell is used for successive genetic modifications resulting in an increased activity of a protein having the (enzymatic) activity of a GFAT.

In a further embodiment of processes according to the invention for preparing a plant which synthesizes hyaluronan, the genetic modification consists in the introduction of at least one foreign nucleic acid molecule into the genome of the plant cell, where the presence or the expression of the foreign nucleic acid molecule(s) results in an increased activity of a protein having the (enzymatic) activity of a GFAT in the plant cell.

As already described above for the foreign nucleic acid molecules introduced for genetic modification into the plant cell or plant, what is introduced in step a) of the processes according to the invention for preparing a plant which synthesizes hyaluronan may be an individual nucleic acid molecule or a plurality of nucleic acid molecules. Thus, the foreign nucleic acid molecules coding for a hyaluronan synthase and/or coding for a protein having the (enzymatic) activity of a GFAT may be present together on a single nucleic acid molecule, or they may be present on separate nucleic acid molecules. If the nucleic acid molecules coding for a hyaluronan synthase and coding for a protein having the activity of a GFAT are present on a plurality of nucleic acid molecules, these nucleic acid molecules may be introduced simultaneously or in successive steps into a plant cell.

Furthermore, to introduce a foreign nucleic acid molecule in the practice of processes according to the invention for preparing a plant which synthesizes hyaluronan, it is possible to use, instead of a wild-type plant cell or wild-type plant, mutant cells or mutants which are distinguished in that they already have an increased activity of a protein having the (enzymatic) activity of a GFAT. If the mutant cell or the mutant already has an increased activity of a protein having the (enzymatic) activity of a GFAT compared to the corresponding wild-type plant cells or wild-type plants, it is sufficient for carrying out a process according to the invention for producing a plant which synthesizes hyaluronan to introduce into said mutant cell or mutant a foreign nucleic acid molecule coding for a hyaluronan synthase.

All said further above concerning the use of mutants for the preparation of genetically modified plant cells according to the invention or genetically modified plants according to the invention applies here in an analogous manner.

In preferred embodiments, the present invention relates to processes according to the invention for producing a plant which synthesizes hyaluronan, wherein the nucleic acid molecule coding for a hyaluronan synthase in step a) is selected from the group consisting of:
a) nucleic acid molecules characterized in that they code for a viral hyaluronan synthase,
b) nucleic acid molecules characterized in that they code for a hyaluronan synthase of a *Chlorella*-infecting virus,
c) nucleic acid molecules characterized in that they code for a hyaluronan synthase of a *Paramecium bursaria Chlorella* Virus 1,
d) nucleic acid molecules characterized in that they code for a hyaluronan synthase of a *Paramecium bursaria Chlorella* Virus 1 of strain H1,
e) nucleic acid molecules characterized in that the codons of the nucleic acid molecule coding for a hyaluronan synthase are modified compared to the codons of the nucleic acid molecule which codes for the hyaluronan synthase in the parent organism of the hyaluronan synthase,
f) nucleic acid molecules characterized in that the codons of the hyaluronan synthase have been modified thus that they are adapted to the frequency of the use of the codons of the plant cell or of the plant into whose genome they are to be integrated or are integrated,
g) nucleic acid molecules characterized in that they code for a hyaluronan synthase having the amino acid sequence shown under SEQ ID NO 2 or that they code for a hyaluronan synthase whose amino acid sequence is at least 70%, preferably at least 80%, particularly preferably at least 90%, especially preferably at least 95% and most preferably at least 98% identical to the amino acid sequence shown under SEQ ID NO 2,
h) nucleic acid molecules characterized in that they code for a protein whose amino acid sequence can be derived from the coding region of the nucleic acid sequence inserted into plasmid DSM16664 or that it codes for a protein whose amino acid sequence is at least 70%, preferably at least 80%, particularly preferably at least 90%, especially preferably at least 95% and most preferably at least 98% identical to the amino acid sequence which can be derived from the coding region of the nucleic acid sequence inserted into plasmid DSM16664,
i) nucleic acid molecules comprising a nucleic acid sequence shown under SEQ ID NO 1 or SEQ ID NO 3 or being at least 70%, preferably at least 80%, with preference at least 90%, especially preferably at least 95% and most preferably at least 98% identical to the nucleic acid sequence shown under SEQ ID NO 1 or SEQ ID NO 3,
j) nucleic acid molecules comprising the nucleic acid sequence inserted into plasmid DSM16664 or being at least 70%, preferably at least 80%, with preference at least 90%, especially preferably at least 95% and most preferably at least 98% identical to the nucleic acid sequence inserted into plasmid DSM16664,
k) nucleic acid molecules coding for a hyaluronan synthase, where the nucleic acid sequences coding for the hyaluronan synthase are linked to regulatory elements (promoter) which initiate the transcription in plant cells or
l) nucleic acid molecules according to k) where the promoters are tissue-specific promoters, particularly preferably promoters which initiate the initiation of transcription specifically in plant tuber, fruit or seed cells.

In preferred embodiments, the present invention relates to processes according to the invention for producing a plant which synthesizes hyaluronan, where the nucleic acid molecule coding for a protein having the activity of a GFAT is selected from the group consisting of:
a) nucleic acid molecules characterized in that they code for a protein having the activity of a GFAT originating from bacteria, animals or plants, preferably from *Escherichia coli* or the mouse,
b) nucleic acid molecules characterized in that they code for a protein having the activity of a GFAT of a *Chlorella*-infecting virus,
c) nucleic acid molecules characterized in that they code for a protein having the activity of a GFAT of a *Paramecium bursaria Chlorella* virus,
d) nucleic acid molecules characterized in that the codons of the nucleic acid molecule coding for a protein having the activity of a GFAT are modified compared to the codons of a nucleic acid molecule coding for the corresponding protein having the activity of a GFAT of the parent organism,
e) nucleic acid molecules characterized in that the codons of the protein having the activity of a GFAT are modified thus that they are adapted to the frequency of the use of the codons of the plant cell or of the plant into whose genome they are to be integrated or are integrated,
f) nucleic acid molecules coding for a protein having the amino acid sequence shown under SEQ ID NO 5 or for a protein having the amino acid sequence shown under SEQ ID NO 7 or for a protein having the amino acid sequence shown under SEQ ID NO 9;
g) nucleic acid molecules coding for a protein whose sequence is at least 70%, preferably at least 80%, with preference at least 90%, especially preferably at least 95% and most preferably at least 98% identical to the amino acid sequence shown under SEQ ID NO 5 or under SEQ ID NO 7 or under SEQ ID NO 9;
h) nucleic acid molecules comprising the nucleic acid sequence shown under SEQ ID NO 4 or a sequence complementary thereto or the nucleic acid sequence shown under SEQ ID NO 6 or a sequence complementary thereto or the nucleic acid sequence shown under SEQ ID NO 8 or a sequence complementary thereto or the nucleic acid sequence shown under SEQ ID NO 10 or a sequence complementary thereto;
i) nucleic acid molecules which are at least at least 70%, preferably at least 80%, with preference at least 90%, especially preferably at least 95% and most preferably at least 98% identical to the nucleic acid sequences described under h);
j) nucleic acid molecules which hybridize under stringent conditions with at least one strand of the nucleic acid sequences described under f) or h);
k) nucleic acid molecules whose nucleotide sequence differs from the sequence of the nucleic acid molecules mentioned under f) or h) owing to the degeneration of the genetic code; and
l) nucleic acid molecules which are fragments, allelic variants and/or derivatives of the nucleic acid molecules mentioned under a), b), c), d), e), f) or h),
m) nucleic acid molecules coding for a protein having the activity of a GFAT, where the nucleic acid sequences coding for a protein having the activity of a GFAT are linked to regulatory elements (promoter) which initiate the transcription in plant cells or
n) nucleic acid molecules according to m), where the promoters are tissue-specific promoters, particularly preferably promoters which initiate the transcription specifically in plant tuber, leaf, fruit or seed cells.

In a further preferred embodiment, processes according to the invention for producing a plant which synthesizes hyaluronan are used for producing genetically modified plants according to the invention.

The present invention also provides plants obtainable by a process according to the invention for producing a plant which synthesizes hyaluronan.

The present invention furthermore relates to a process for producing hyaluronan which comprises the step of extracting hyaluronan from genetically modified plant cells according to the invention, from genetically modified plants according to the invention, from propagation material according to the invention, from harvestable plant parts according to the invention or from plants or parts of these plants obtainable by a process according to the invention for producing plants which synthesize hyaluronan.

Preferably, such a process also comprises the step of harvesting the cultivated genetically modified plant cells according to the invention, the genetically modified plants according to the invention, the propagation material according to the invention, the harvestable plant parts according to the invention, the processible plant parts according to the invention prior to extracting the hyaluronan, and particularly preferably furthermore the step of cultivating genetically modified plant cells according to the invention or genetically modified plants according to the invention prior to harvesting.

In contrast to bacterial or animal tissues, plant tissues have no hyaluronidases and do not contain any hyaladherins. Accordingly, as already described above, extraction of hyaluronan from plant tissues is possible using relatively simple methods. If required, the aqueous extracts, described above, of plant cells or tissues containing hyaluronan can be purified further using methods known to the person skilled in the art, such as, for example, repeated precipitation with ethanol. A preferred method for purifying hyaluronan is described under General Methods item 2.

The processes already described for extracting hyaluronan from genetically modified plant cells according to the invention or genetically modified plants according to the invention are also suitable for isolating hyaluronan from propagation material according to the invention, from harvestable plant parts according to the invention or from plants or parts of these plants obtainable by a process according to the invention for preparing plants which synthesize hyaluronan.

The present invention also provides the use of genetically modified plant cells according to the invention, genetically modified plants according to the invention, propagation material according to the invention, harvestable plant parts according to the invention, processible plant parts according to the invention or plants obtainable by a process according to the invention for preparing hyaluronan.

The present invention furthermore relates to compositions comprising genetically modified plant cells according to the invention. Here, it is immaterial whether the plant cells are intact or no longer intact because they have been destroyed, for example, by processing. The compositions are preferably foodstuff or feedstuff, pharmaceutical or cosmetic products.

The present invention preferably provides compositions comprising components of genetically modified plant cells according to the invention, of genetically modified plants according to the invention, of propagation material according to the invention, of harvestable plant parts according to the invention or of plants obtainable by a process according to the invention and comprising recombinant nucleic acid molecules, where the recombinant nucleic acid molecules are characterized in that they comprise nucleic acid molecules coding for a hyaluronan synthase and proteins having the (enzymatic) activity of a GFAT.

A stable integration of foreign nucleic acid molecules into the genome of a plant cell or plant results in the foreign nucleic acid molecules being flanked after integration into the genome of a plant cell or plant by genomic plant nucleic acid sequences. Accordingly, in a preferred embodiment, compositions according to the invention are characterized in that the recombinant nucleic acid molecules present in the composition according to the invention are flanked by genomic plant nucleic acid sequences.

Here, the genomic plant nucleic acid sequences may be any sequences naturally present in the genome of the plant cell or plant used for preparing the composition.

The recombinant nucleic acid molecules present in the compositions according to the invention may be individual or various recombinant nucleic acid molecules which nucleic acid molecules coding for a hyaluronan synthase and proteins having the (enzymatic) activity of a GFAT are present on a nucleic acid molecule, or those where the nucleic acid molecules may be present on separate recombinant nucleic acid molecules. Nucleic acid molecules coding for a hyaluronan synthase or coding for a protein having the (enzymatic) activity of a GFAT may be present together on a single recombinant nucleic acid molecule, or two of the nucleic acid molecules mentioned may be present together on a single recombinant nucleic acid molecule and the third nucleic acid molecule may be present on another recombinant nucleic acid molecule in any possible combination, or all nucleic acid molecules mentioned may in each case be present on individual separate recombinant nucleic acid molecules. Depending on how the nucleic acid molecules coding for a hyaluronan synthase or coding for a protein having the (enzymatic) activity of a GFAT are present in a composition according to the invention, they may be flanked by identical or different genomic plant nucleic acid sequences.

That compositions according to the invention comprise recombinant nucleic acid molecules may be demonstrated using methods known to the person skilled in the art, such as, for example, methods based on hybridization or, preferably, using methods based on PCR (polymerase chain reaction).

Preferably, compositions according to the invention comprise at least 0.005%, with preference at least 0.01%, particularly preferably at least 0.05% and especially preferably at least 0.1% of hyaluronan.

Preferably, compositions according to the invention comprise at most 5%, with preference at most 2%, particularly preferably at most 1% and especially preferably at least 0.5% of hyaluronan.

As already mentioned above, it is possible to use genetically modified plant cells according to the invention, genetically modified plants according to the invention, propagation material according to the invention, harvestable plant parts according to the invention, processible plant parts according to the invention, consumable plant parts according to the invention or plants obtainable by a process according to the invention to prepare foodstuff or feedstuff. However, use as raw materials for industrial applications is also possible, without hyaluronan having to be isolated. Thus, for example, genetically modified plants according to the invention or parts of genetically modified plants according to the invention can be applied to areas under agricultural cultivation to achieve increased water binding of the soil. Furthermore, genetically modified plants according to the invention or genetically modified plant cells according to the invention can be used for preparing drying agents (for example for use when shipping moisture-sensitive items) or as absorbers of liquids (for example in nappies or for absorbing spilt aqueous liquids). For such applications, it is possible to use entire genetically modified plants according to the invention, parts of genetically modified plants according to the invention or comminuted (for example ground) genetically modified plants according to the invention or plant parts according to the invention, as required. Suitable for applications in which ground plants or plant parts are used are in particular plant parts containing hyaluronan, but only a low proportion of water. These are preferably grains of cereal plants (corn, rice, wheat, rye, oats, barley, sago or sorghum). Since genetically modified plant cells according to the invention and genetically modified plants according to the invention have a higher hyaluronan content than transgenic plants described in the literature, compared to these less material has to be used for industrial applications when use is made of genetically modified plant cells according to the invention or genetically modified plants according to the invention.

The present invention also provides processes for preparing a composition according to the invention, where genetically modified plant cells according to the invention, genetically modified plants according to the invention, propagation material according to the invention, harvestable plant parts according to the invention, processible plant parts according to the invention, consumable plant parts according to the invention or plants obtainable by a process according to the invention for producing a plant which synthesizes hyaluronan are used. The processes for preparing a composition according to the invention are preferably processes for preparing foodstuff or feedstuff, processes for preparing a pharmaceutical product or processes for preparing a cosmetic product.

Processes for preparing foodstuff or feedstuff are known to the person skilled in the art. Processes for using genetically modified plants according to the invention or plant parts according to the invention in industrial areas are also known to the person skilled in the art and include inter alia comminuting or grinding of genetically modified plants according to the invention or plant parts according to the invention; however, they are not exclusively limited thereto. Some of the advantages resulting from using subject-matters according to the invention for preparing foodstuff/feedstuff or for use in industrial areas have already been described above.

A process according to the invention for preparing a composition is particularly preferably a process for preparing a composition which comprises hyaluronan.

Compositions obtainable by a process for preparing a composition according to the invention are likewise provided by the present invention.

The present invention also relates to the use of genetically modified plant cells according to the invention, genetically modified plants according to the invention, propagation material according to the invention, harvestable plant parts according to the invention, processible plant parts according to the invention, consumable plant parts according to the invention or plants obtainable by a process according to the invention for producing a plant which synthesizes hyaluronan for preparing a composition according to the invention. Preference is given to the use of genetically modified plant cells according to the invention, genetically modified plants according to the invention, propagation material according to the invention, harvestable plant parts according to the invention, processible plant parts according to the invention, consumable plant parts according to the invention or of plants obtainable by a process according to the invention for producing a plant which synthesizes hyaluronan for preparing foodstuff or feedstuff, for preparing a pharmaceutic or for preparing a cosmetic product.

Description of the Sequences

SEQ ID NO 1: Nucleic acid sequence coding for a hyaluronan synthase of *Paramecium bursaria Chlorella* Virus 1.

SEQ ID NO 2: Amino acid sequence of a hyaluronan synthase of the *Paramecium bursaria Chlorella* Virus 1. The amino acid sequence shown can be derived from SEQ ID NO 1.

SEQ ID NO 3: Synthetic nucleic acid sequence coding for a hyaluronan synthase of *Paramecium bursaria Chlorella* Virus 1. The synthesis of the codons of the sequence shown was carried out such that it is adapted to the use of codons in plant cells. The nucleic acid sequence shown codes for a protein having the amino acid sequence shown under SEQ ID NO 2.

SEQ ID NO 4: Nucleic acid sequence coding for a protein having the activity of a GFAT-1 from the mouse.

SEQ ID NO 5: Amino acid sequence of a protein having the activity of a GFAT-1 from the mouse. The amino acid sequence shown can be derived from SEQ ID NO 4.

SEQ ID NO 6: Nucleic acid sequence coding for a protein having the activity of a GFAT-2 from the mouse.

SEQ ID NO 7: Amino acid sequence of a protein having the activity of a GFAT-2 from the mouse. The amino acid sequence shown can be derived from SEQ ID NO 6.

SEQ ID NO 8: Nucleic acid sequence coding for a protein having the activity of a GFAT from *Escherichia coli*.

SEQ ID NO 9: Amino acid sequence of a protein having the activity of a GFAT from *Escherichia coli*. The amino acid sequence shown can be derived from SEQ ID NO 8.

SEQ ID NO 10: Synthetic nucleic acid sequence coding for a protein having the activity of a GFAT from *Escherichia coli*. The synthesis of the codons of the sequence shown was carried out such that it was adapted to the use of codons in plant cells. The nucleic acid sequence shown codes for a protein having the amino acid sequence shown under SEQ ID NO 9.

SEQ ID NO 11: Synthetic Oligonucleotide used in Example 1.

SEQ ID NO 12: Synthetic Oligonucleotide used in Example 1.

SEQ ID NO 13: Synthetic Oligonucleotide used as PCR primer in Example 10.

SEQ ID NO 14: Synthetic Oligonucleotide used as PCR primer in Example 10.

All literature cited, including but not limited to accession numbers for nucleic acid and amino acid sequences are incorporated into the description by way of reference.

DESCRIPTION OF THE FIGURES

FIG. 1: Shows a calibration curve and the corresponding equation of the regression line used for calculating the hyaluronan content in plant tissue. The calibration curve was established with the aid of the commercial test kit (Hyaluronic Acid (HA) test kit from Corgenix Inc., Colorado, USA, Prod. No. 029-001) and the standard solutions supplied therewith.

GENERAL METHODS

Methods which can be used in connection with the present invention are described below. These methods are specific embodiments; however, the present invention is not limited to these methods. It is known to the person skilled in the art that the invention can be carried out in the same manner by modifying the methods described and/or by replacing individual methods or parts of methods by alternative methods or alternative parts of methods.

1. Transformation of Potato Plants

Potato plants were transformed with the aid of *Agrobacterium*, as described in Rocha-Sosa et al. (EMBO J. 8, (1989), 23-29).

2. Isolation of Hyaluronan from Plant Tissue

To detect the presence of hyaluronan and to determine the hyaluronan content in plant tissue, plant material was worked up as follows: 200 µl of water (demineralized, conductivity ≥18 MΩ) were added to about 0.3 g of material, and the mixture was comminuted in a laboratory oscillating ball mill (MM200, from Retsch, Germany, 30 sec at 30 Hz). A further 800 µl of water (demineralized, conductivity ≥18 MΩ) was then added, and the mixture was mixed well (using, for example, a Vortex mixer). Cell debris and insoluble components were separated from the supernatant by centrifuging at 16 000×g for 5 minutes.

3. Purification of Hyaluronan

About 100 grams of tubers were peeled, cut into pieces of a size of about 1 cm$^3$ and, after addition of 100 ml of water (demineralized, conductivity ≥18 MΩ) comminuted in a Warring blender at maximum speed for about 30 seconds. The cell debris was then removed using a tea sieve. The cell debris that had been removed was resuspended in 300 ml of water (demineralized, conductivity ≥18 MΩ) and again removed using a tea sieve. The two suspensions obtained (100 ml+300 ml) were combined and centrifuged at 13 000×g for 15 minutes. NaCl was added to the centrifugation supernatant obtained until a final concentration of 1% had been reached. After the NaCl had gone into solution, precipitation was carried out by addition of twice the volume of ethanol followed by thorough mixing and incubation at −20° C. overnight. The mixture was then centrifuged at 13 000×g for 15 minutes. The sedimented precipitate obtained after this centrifugation was dissolved in 100 ml of buffer (50 mM Tris HCl, pH 8, 1 mM CaCl$_2$) and proteinase K was then added to a final concentration of 100 µg/ml and the solution was incubated at 42° C. for 2 hours. This was followed by 10 minutes of incubation at 95° C. Once more, NaCl was added to this solution until a final concentration of 1% had been reached. After the NaCl had gone into solution, another precipitation was carried out by addition of twice the volume of ethanol, thorough mixing and incubation at −20° C. for about 96 hours. This was followed by 15 minutes of centrifugation at 13 000×g. The sedimented precipitate obtained after this centrifugation was dissolved in 30 ml of water (demineralized, conductivity ≥18 MΩ), and once more, NaCl was added to a final concentration of 1%. By adding twice the volume of ethanol, thorough mixing and incubation at −20° C. overnight, another precipitation was carried out. The precipitate obtained after subsequent centrifugation at 13000×g for 15 minutes was dissolved in 20 ml of water (demineralized, conductivity ≥18 MΩ).

Further purification was carried out by centrifugal filtration. To this end, in each case 5 ml of the dissolved precipitate were applied to a membrane filter (Centricon Amicon, pore width 10 000 NMWL, Prod. No. UCF8 010 96), and the sample was centrifuged at 2200×g until only about 3 ml of the solution above the filter remained. Two more times, in each case 3 ml of water (demineralized, conductivity ≥18 MΩ) were then added to the solution above the membrane and in each case re-centrifuged under identical conditions until, at the end, only about 3 ml of the solution above the filter remained. The solutions still present above the membrane after centrifugal filtration were taken off, and the membrane was rinsed repeatedly (three to five times) with about 1.5 ml of water (demineralized, conductivity ≥18 MΩ). All solutions which were still present above the membrane and the solutions obtained from rinsing were combined, NaCl was added to a final concentration of 1%, after the NaCl had gone into solution, twice the volume of ethanol was added, the sample was mixed and a precipitate was obtained by storage at −20° C. overnight. The precipitate obtained after subsequent centrifugation at 13 000×g for 15 minutes was dissolved in 4 ml of water (demineralized, conductivity ≥18 MΩ) and then freeze-dried (24 hours under a pressure of 0.37 mbar, freeze drying apparatus Christ Alpha 1-4 from Christ, Osterode, Germany).

4. Detection of Hyaluronan and Determination of the Hyaluronan Content

Hyaluronan was detected using a commercial test (hyaluronic acid (HA) test kit from Corgenix, Inc., Colorado, USA, Prod. No. 029-001) according to the instructions of the manufacturer which are herewith incorporated into the description by way of reference. The test principle is based on the availability of a protein which binds specifically to hyaluronan (HABP) and is carried out similarly to an ELISA, where a color reaction indicates the hyaluronan content in the sample examined. Accordingly, for the quantitative determination of hyaluronan, the samples to be measured should be employed in a concentration such that it is within the stated limits (for example: dilution of the sample in question or use of less water for extracting hyaluronan from plant tissue, depending on whether a limit was exceeded or not reached).

In parallel batches, aliquots of the samples to be determined were initially subjected to hyaluronidase digestion and then measured using the commercial test (hyaluronic acid (HA) test kit from Corgenix, Inc., Colorado, USA, Prod. No. 029-001). Hyaluronidase digestion was carried out using 400 µl of potato tuber extract in hyaluronidase buffer (0.1 M potassium phosphate buffer, pH 5.3; 150 mM NaCl) by adding 5 µg (~3 units) of hyaluronidase (hyaluronidase type III from Sigma, Prod. No. H 2251) and incubating at 37° C. for 30 min.

In each case in a dilution of 1:10, all samples were then used for determining the hyaluronan content.

5. Determination of the Activity of a GFAT

The activity of a protein having the activity of GFAT is determined as described in Rachel et al. (1996, J. Bacteriol. 178 (8), 2320-2327).

To distinguish whether a protein has the activity of a GFAT-1 or GFAT-2, the method described in Hu et al. (2004, J. Biol. Chem. 279 (29), 29988-29993) is used.

6. Transformation of Rice Plants

Rice plants were transformed by the method described by Hiei et al. (1994, Plant Journal 6(2), 271-282).

7. Transformation of Tomato Plants

Tomato plants were transformed with the aid of *Agrobacterium* according to the method described in U.S. Pat. No. 5,565,347.

EXAMPLES

1. Preparation of the Plant Expression Vector IR 47-71

The plasmid pBinAR is a derivative of the binary vector plasmid pBin19 (Bevan, 1984, Nucl Acids Res 12: 8711-8721) which was constructed as follows:

A fragment of a length of 529 bp which comprised the nucleotides 6909-7437 of the 35S promoter of the cauliflower mosaic virus was isolated as EcoR I/Kpn I fragment from the plasmid pDH51 (Pietrzak et al, 1986 Nucleic Acids Res. 14, 5858) and ligated between the EcoR I and Kpn I restriction sites of the polylinker of pUC18. In this manner, the plasmid pUC18-35S was formed. Using the restriction endonucleases Hind III and Pvu II, a fragment of a length of 192 bp which included the polyadenylation signal (3' terminus) of the Octopin Synthase gene (gene 3) of the T-DNA of the Ti plasmid pTiACH5 (Gielen et al, 1984, EMBO Journal 3, 835-846) (nucleotides 11 749-11 939) was isolated from the plasmid pAGV40 (Herrera-Estrella et al, 1983 Nature, 303, 209-213). Following addition of Sph I linkers to the Pvu II restriction site, the fragment was ligated between the Sph I and Hind III restriction sites of pUC18-35S. This gave the plasmid pA7. Here, the entire polylinker comprising the 35S promoter and ocs terminator was removed using EcoR I and Hind III and ligated into the appropriately cleaved vector pBin19. This gave the plant expression vector pBinAR (Höfgen and Willmitzer, 1990, Plant Science 66, 221-230).

The promoter of the patatin gene B33 from *Solanum tuberosum* (Rocha-Sosa et al., 1989, EMBO J. 8, 23-29) was, as Dra I fragment (nucleotides −1512-+14), ligated into the Sst I-cleaved vector pUC19 whose ends had been blunted using T4-DNA polymerase. This gave the plasmid pUC19-B33. From this plasmid, the B33 promoter was removed using EcoR I and Sma I and ligated into the appropriately restricted vector pBinAR. This gave the plant expression vector pBinB33.

To facilitate further cloning steps, the MCS (Multiple Cloning Site) was extended. To this end, two complementary oligonucleotides were synthesized, heated at 95° C. for 5 minutes, slowly cooled to room temperature to allow good fixation (annealing) and cloned into the Sal I and Kpn I restriction sites of pBinB33. The oligonucleotides used for this purpose had the following sequence:

```
                                              (SEQ ID NO: 11)
5'-TCg ACA ggC CTg gAT CCT TAA TTA AAC TAg TCT CgA ggA gCT Cgg TAC-3'
                                              (SEQ ID NO: 12)
5'-CgA gCT CCT CgA gAC TAg TTT AAT TAA ggA TCC Agg

CCT g-3'
```

The plasmid obtained was named IR 47-71.

2. Preparation of the Plant Expression Vector pBinARHyg

The fragment comprising the 35S promoter, the ocs terminator and the entire Multiple Cloning Site was removed from pA7 using the restriction endonucleases EcoR I and Hind III and cloned into the vector pBIBHyg (Becker, 1990, Nucleic Acids Res. 18, 203) which had been cut using the same restriction endonucleases. The plasmid obtained was named pBinARHyg.

3. Preparation of the Plant Expression Vector pBinB33-Hyg

The EcoRI-HindIII fragment comprising the B33 promoter, part of the polylinker and the ocs terminator was excised from the plasmid pBinB33 and ligated into the appropriately restricted vector pBIBHyg (Becker, 1990, Nucleic Acids Res. 18, 203). The plant expression vector obtained was named pBinARHyg.

4. Synthesis of Nucleic Acid molecules a) Synthesis of Nucleic Acid Molecules Coding for a Hyaluronan Synthase of *Paramecium bursaria Chlorella* Virus 1

The nucleic acid sequence coding for a hyaluronan synthase (HAS) of *Paramecium bursaria Chlorella* Virus 1 was synthesized by Medigenomix GmbH (Munich, Germany) and cloned into the vector pCR2.1 from Invitrogen (Prod. No. K2000-01). The plasmid obtained was named IC 323-215. The synthetic nucleic acid sequence coding for the HAS protein from *Paramecium bursaria Chlorella* Virus 1, is shown under SEQ ID NO 3. The corresponding nucleic acid sequence originally isolated from the *Paramecium bursaria Chlorella* Virus 1 is shown under SEQ ID NO 1.

b) Synthesis of Nucleic Acid Molecules Coding for a Protein Having the Activity of a GFAT from *Escherichia coli*

The nucleic acid sequence coding for a protein having the activity of a GFAT from *Escherichia coli* was synthesized by Entelechon GmbH and cloned into the vector pCR4Topo from Invitrogen (Prod. No. K4510-20). The plasmid obtained was named IC 373-256. The synthetic nucleic acid sequence coding for a protein having the activity of a GFAT from *Escherichia coli*, is shown under SEQ ID NO 10. The corresponding nucleic acid sequence originally isolated from *Escherichia coli* is shown under SEQ ID NO 8.

5. Origin of Further Nucleic Acid Molecules a) Nucleic Acid Molecules Coding for a Protein Having the Activity of a GFAT-1 from the Mouse The nucleic acid sequence coding for a protein having the activity of a GFAT-1 was purchased from BioCat GmbH, Heidelberg (Art. No. MMM1013-65346, cDNA clone MGC:58262, IMAGE:6742987). This is a clone produced by I.M.A.G.E. Konsortium and distributed by BioCat GmbH. Here, the cDNA coding for a protein having the activity of a GFAT-1 was cloned into the vector pCMV Sport 6 from Invitrogen. The plasmid obtained was named IC 365-256. The nucleic acid sequence, inserted into IC 365-256, coding for a protein having the activity of a GFAT-1 from *Mus musculus* has, compared to the nucleic acid sequence of SEQ ID NO 4, a base exchange from T to C in position 1090 and a base exchange from G to A in position 2027. These base exchanges do not result in amino acid exchanges of the amino acid sequences coded for by the two different nucleic acid molecules.

The coding nucleic acid sequence for the protein having the activity of a GFAT-1 from the mouse is shown in SEQ ID NO 4.

To facilitate subsequent cloning steps, the sequence coding for a protein having the activity of a GFAT-1 was isolated using the restriction endonucleases Xho I and Eco RV from IC 365-256 and cloned into the plasmid pME9 (pBlueSkript vector from Stratagene) having a modified multiple cloning site which additionally has a Pac I restriction site at both ends, which plasmid had been cut with the same restriction endonucleases. The plasmid obtained was named IC 367-256.

b) Nucleic Acid Molecules Coding for a Protein Having the Activity of a GFAT-2 from the Mouse Nucleic acid molecules coding for a protein having the activity of a GFAT-2 from the mouse were purchased from Invitrogen (Clone ID 4167189, cDNA clone MGC:18324, IMAGE:4167189). This is a clone which is produced by I.M.A.G.E. Konsortium and distributed by Invitrogen. Here, the cDNA coding for a protein having the activity of a GFAT-2 is cloned into the vector pCMV Sport 6 from Invitrogen. The plasmid was named IC 369-256. The nucleic acid sequence coding for the protein having the activity of a GFAT-2 from *Mus musculus* is of SEQ ID NO 6.

6. Preparation of the Plant Expression Vector IC 341-222 which Comprises a Coding Nucleic Acid Sequence for a Hyaluronan Synthase of *Paramecium bursaria Chlorella* virus 1

Using restriction digestion with BamH I and Xho I, nucleic acid molecules comprising the coding sequence of hyaluronan synthase were isolated from the plasmid IC 323-215 and cloned into the BamH I and Xho I restriction sites of the plasmid IR 47-71. The plant expression vector obtained was named IC 341-222.

7. Preparation of the Plant Expression Vector IC 399-299 Comprising a Coding Nucleic Acid Sequence for a Protein Having the Activity of a GFAT-2 from the Mouse Using restriction digestion with Xho I and Asp 718, nucleic acid molecules comprising the coding sequence for a protein having the activity of a GFAT-2 from the mouse were isolated from the plasmid 369-256 and cloned into the plant expression vector pBinB33-Hyg which had been cut with the same restriction endonucleases. The plant expression vector obtained was named IC 399-299.

8. Preparation of the Plant Expression Vector IC 399-300 Comprising a Coding Nucleic Acid Sequence for a Protein Having the Activity of a GFAT from *E. coli*

Nucleic acid molecules comprising the coding sequence of the protein having the activity of a GFAT from *E. coli* were isolated from the plasmid 373-256 by restriction digestion with Sac I and Sbf I and cloned into the plant expression vector pBinB33-Hyg which had been cut with the same restriction endonucleases. The plant expression vector obtained was named IC 399-300.

9. Preparation of the Plant Expression Vector pBA16, which Contains a Coding Nucleic Acid Sequence for a Hyaluronan Synthase of *Paramecium Bursaria Chlorella* Virus 1

Using the restriction endonuclease Asp 7181, a fragment comprising the coding nucleic acid sequence for a hyaluronan synthase of *Paramecium bursaria Chlorella* virus 1 was isolated from the plasmid IC 323-215, the ends of the fragment were blunted using Klenow polymerase and the resulting fragment was then once more cleaved using the restriction endonuclease Pac I. The fragment obtained in this manner was ligated into the plasmid IR103-123 (described in WO 2006 032538), which had been cleaved using the restriction endonucleases Pac I and Ecl136 II. The plant expression vector obtained was referred to as pBA16.

10. Preparation of the Plant Expression Vector IC 386-299

The DNA of the prolamin promoter from rice (EMBL Accession NO D63901, Sha et al., 1996, Biosci. Biotech. Biochem. 60, 335-337, Wu et al., 1998. Plant Cell Physiol. 39(8), 885-889) was amplified by using genomic DNA isolated from leaves of *Oryza sativa* (cultivar M202).

Conditions Used for PCR Amplification:

For amplification, the DNA polymerase Expand High Fidelity (PCR Systems, Roche Prod. Nr.: 1732641) was used The conditions and buffers supplied by the manufacturer of the afore mentioned kit were used.

| DNA: | 50 ng of genomic rice DNA |
|---|---|
| dNTPs: | 0.83 µM dNTP Mix |

```
0.25 µM Primer prol-F1
                                              (SEQ ID NO: 13)
5'-AAAAACTAGTTCTACATCGGCTTAGGTGTAGCAACACG 0.25 µM Primer prol-R1
                                              (SEQ ID NO: 14)
5'-AAAAGATATCTGTTGTTGGATTCTACTACTATGCTTCAA
```

| Reaction conditions: | | |
|---|---|---|
| Step 1 | 94° C. | 15 sec |
| Step 2 | 60° C. | 15 sec |
| Step 3 | 72° C. | 45 sec |

Steps 1 to 3 were repeated 35 times before the reaction was cooled to 4° C.

The fragment obtained by PCR amplification was cloned by the use of the TA cloning kit (Invitrogen Prod. Nr.: KNM2040-01) into the plasmid pCR 2.1. The resulting plasmid was named MI 4-154.

A nucleic acid fragment comprising the coding sequence of the protein having the activity of a GFAT-2 from the mouse was isolated from plasmid IC 369-256 by using the resetriction endonucleases Not I und Kpn I and cloned into the Not I und Kpn I sites of the vector pMCS5 (purchased from MoBiTec). The plasmid obtained was named IC 385-299. The nucleic acid fragment comprising the coding sequence of the protein having the activity of a GFAT-2 from the mouse was isolated from plasmid IC 385-299 by using the resetriction endonucleases Xho I und Hpa I and cloned into the Xho I and Ecl 136 II restriction sites of plasmid MI 9-154. The obtained plant expression vector was named IC 386-299.

Basis for the preparation of vector MI 9-154 was the plasmid ML 18-56 (WO 05 030941). A multiple cloning site (MCS) comprising sticky ends for cloning into the restriction sites Hind III and Pst I and comprising the additional restriction sites Pst I, Sac I, Bln I, Xho I, Hpa I, Spe I and Hind III was prepared by annealing of two complementary synthetic oligonucleotides. The annealed oligonucleotide was cloned into the restriction sites Hind III and Pst I of plasmid ML 18-56. The vector obtained was named MI 8-154. The nucleic acid fragment comprising the prolamin promoter was isolated from plasmid MI 4-154 by using the restriction endonucleases Eco RV und Spe I and cloned into the vector MI 8-154. The obtained plasmid was named MI 9-154.

11. Transformation of Plants with Plant Expression Vectors Comprising Nucleic Acid Molecules Coding for a Hyaluronan Synthase Potato plants (cv Désirée) were transformed using the plant expression vector IC 341-222, which comprises a coding nucleic acid sequence for a hyaluronan synthase from *Paramecium bursaria Chlorella* virus 1 under the control of the promoter of the patatin gene B33 from *Solanum tuberosum* (Rocha-Sosa et al., 1989, EMBO J. 8, 23-29) using the method given under General Methods item 1. The transgenic potato plants obtained, which were transformed with the plasmid IC 341-222, were named 365 ES.

12. Analysis of the Transgenic Plants Transformed with Plant Expression Vectors Comprising Nucleic Acid Molecules Coding for a Hyaluronan Synthase a) Construction of a Calibration Curve A calibration curve was constructed using the standard solutions supplied with the commercial test kit (hyaluronic acid (HA) test kit from Corgenix, Inc., Colorado, USA, Prod. No. 029-001), according to the methods described by the manufacturer. To determine the extinction at 1600 ng/ml of hyaluronan, double the amount, based on the amount of supplied standard indicated by the manufacturer, comprising 800 ng/ml of hyaluronan was used. In each case, three independent measurement series were carried out, and the corresponding mean was determined. This gave the following calibration curve:

TABLE 1

Values for constructing a calibration curve for the quantitative determination of the hyaluronan content in plant tissue.

| Hyaluronan concentration | Independent individual measurements | | | Mean | n.d. |
|---|---|---|---|---|---|
| | $E_{450\,nm}$ | $E_{450\,nm}$ | $E_{450\,nm}$ | | |
| 0 ng/ml | 0.100 | 0.096 | 0.096 | 0.097 | 0.002 |
| 50 ng/ml | 0.224 | 0.183 | 0.222 | 0.210 | 0.023 |
| 100 ng/ml | 0.396 | 0.263 | 0.377 | 0.345 | 0.072 |
| 200 ng/ml | 0.554 | 0.443 | 0.653 | 0.550 | 0.105 |
| 500 ng/ml | 1.231 | 0.850 | 1.221 | 1.101 | 0.217 |

TABLE 1-continued

Values for constructing a calibration curve for the quantitative determination of the hyaluronan content in plant tissue.

| Hyaluronan concentration | Independent individual measurements | | | Mean | n.d. |
|---|---|---|---|---|---|
| | $E_{450\ nm}$ | $E_{450\ nm}$ | $E_{450\ nm}$ | | |
| 800 ng/ml | 1.465 | 1.265 | 1.795 | 1.508 | 0.268 |
| 1600 ng/ml | 2.089 | 2.487 | 3.170 | 2.582 | 0.547 |

With the aid of software (Microsoft Office Excel 2002, SP2), the measured values obtained were entered into a diagram and the equation of the function of the trend line was determined (see FIG. 1). $E_{450\ nm}$ refers to the extinction at a wavelength of 450 nm, s.d. is the standard deviation of the calculated mean of the individual values.

b) Analysis of Potato Tubers of Lines 365 ES

In a greenhouse, individual plants of the line 365 ES were cultivated in soil in 6 cm pots. In each case about 0.3 g of material of potato tubers of the individual plants was processed according to the method described under General Methods item 2. Using the method described under General Methods item 4, the amount of hyaluronan present in the respective plant extracts was determined, with the aid of the calibration curve shown in Example 12a) and FIG. 1. Here, the supernatant obtained after centrifugation was used in a dilution of 1:10 for determining the hyaluronan content. For selected plants, the following results were obtained:

TABLE 2

Amount of hyaluronan (in μg of hyaluronan per g of fresh weight) produced by independent transgenic plants of the line 365 ES.

| Name of the plant | Weight of the plant material employed [g] | Extinction E450 | Amount of hyaluronan [ng/ml] | Hyaluronan based on the fresh weight of the plant material [μg/g] |
|---|---|---|---|---|
| 365 ES 13 | 0.297 | 2.746 | 14 | 47 |
| 365 ES 74 | 0.306 | 4.000 | 20816 | 68 |
| Wild-type | 0.305 | 0.111 | n.d. | n.d. |

Column 1 refers to the plant from which tuber material was harvested (here, "wild-type" refers to untransformed plants which, however, have the genotype used as starting material for the transformation). Column 2 indicates the amount of tuber material of the plant in question used for determining the hyaluronan content. Column 3 contains the measured extinction of a 1:10 dilution of the respective plant extract. Column 4 was calculated with the aid of the regression line equation (see FIG. 1) taking into account the dilution factor, as follows: ((value column 3 − 0.149)/0.00185) × 10. Column 5 indicates the amount of hyaluronan based on the fresh weight used and was calculated as follows: (value column 4/value column 2)/1000. "n.d." means not detectable.

13. Transformation of Hyaluronan-Synthesizing Plants with Plant Expression Vectors Comprising Coding Nucleic Acid Sequences for a Protein Having the Activity of a GFAT from *Escherichia coli* a) Transformation of Plants

Potato plants of the lines 365 ES 13 and 365 ES 74 were in each case transformed with the plant expression vector IC 399-300 using the method given under General Methods item 1. The transgenic potato plants obtained after transformation of line 365 ES 74 with the plasmid IC 399-300, were named 433 ES.

b) Analysis of Potato Tubers of Line 433 ES

In a greenhouse, individual plants of the line 433 ES were cultivated in soil in 6 cm pots. In each case about 0.3 g of material of potato tubers and/or leaves of the individual plants was processed according to the method described under General Methods item 2. Using the method described under General Methods item 4, the amount of hyaluronan present in the respective plant extracts was determined, with the aid of the calibration curve shown in Example 12a) and FIG. 1. Here, the supernatant obtained after centrifugation was used in a dilution of 1:10 for determining the hyaluronan content. For selected plants, the following results were obtained:

TABELLE 3

Amount of hyaluronan ("HA" in μg of hyaluronan per g of fresh weight) produced by independent transgenic plants of the line 433 ES.

| Name of the plant | Amount of HA in leaves [μg/g FG] | Amount of HA in tubers [μg/g FG] |
|---|---|---|
| 433ES 1 | 111.84 | 126.70 |
| 433ES 3 | 303.34 | 203.16 |
| 433ES 4 | 3142.41 | |
| 433ES 5 | 312.98 | 825.96 |
| 433ES 7 | 1492.94 | |
| 433ES 8 | 914.03 | |
| 433ES 9 | 1858.68 | |
| 433ES 10 | 357.90 | |
| 433ES 11 | 5962.82 | |
| 433ES 12 | | 662.99 |
| 433ES 13 | 626.52 | 624.33 |
| 433ES 14 | 665.23 | |
| 433ES 15 | 601.36 | |
| 433ES 16 | 3416.94 | |
| 433ES 18 | 781.02 | |
| 433ES 19 | 3294.09 | |
| 433ES 20 | 1348.85 | 975.18 |
| 433ES 21 | 937.92 | |

TABELLE 3-continued

Amount of hyaluronan ("HA" in μg of hyaluronan per g of fresh weight) produced by independent transgenic plants of the line 433 ES.

| Name of the plant | Amount of HA in leaves [μg/g FG] | Amount of HA in tubers [μg/g FG] |
|---|---|---|
| 433ES 22 | 1086.45 | |
| 433ES 23 | 1327.28 | |
| 433ES 24 | 340.80 | 76.00 |
| 433ES 25 | 1529.95 | |
| 433ES 26 | 375.53 | |
| 433ES 27 | | 425.65 |
| 433ES 28 | 1850.99 | 294.98 |
| 433ES 30 | 2512.40 | |
| 433ES 31 | 3337.54 | |
| 433ES 32 | 1583.60 | |
| 433ES 34 | 3552.44 | |
| 433ES 35 | 5419.43 | |
| 433ES 36 | 902.01 | |
| 433ES 37 | 829.35 | |
| 433ES 38 | 1536.55 | |
| wt-1 | 0.40 | n.d. |
| wt-2 | 0.34 | n.d. |

TABELLE 3-continued

Amount of hyaluronan („HA" in µg of hyaluronan per g of fresh weight) produced by independent transgenic plants of the line 433 ES.

| Name of the plant | Amount of HA in leaves [µg/g FG] | Amount of HA in tubers [µg/g FG] |
|---|---|---|
| wt-3 | n.d. | |
| 365 ES 74-1 | 265.1 | |
| 365 ES 74-2 | | 91.84 |
| 365 ES 74-3 | 193.5 | |
| 365 ES 74-4 | | 175.48 |
| 365 ES 74-5 | 73.9 | |
| 365 ES 74-6 | | 168.68 |
| 365 ES 74-7 | 67.58 | |
| 365 ES 74-8 | | 121.89 |
| 365 ES 74-9 | 62.23 | |
| 365 ES 74-10 | | 275.24 |
| 365 ES 74-11 | 134.56 | |

Column 1 refers to the plant from which tuber or leaf material was harvested (here, "wild-type" refers to untransformed plants and ES 365 74 refers to plants which have been used as starting material for transformation with plasmid C 399-300). Columns 2 and 3 refer to the amount of hyaluronan detected in leaves or tubers, respectively.

14. Transformation of Rice Plants a) With Plant Expression Vectors Comprising Nucleic Acid Molecules Coding for a Hyaluronan Synthase from *Paramecium Bursaria Chlorella* Virus 1

Rice plants (cultivar M202) were transformed with the plant expression vector pBA16, which contains a coding nucleic acid sequence for a hyaluronan synthase protein from *Paramecium bursaria Chlorella* virus 1 under the control of the promoter of the globulin gene from *Oryza sativa* (Wu et al., 1998, Plant Cell Physiol. 39(8), 885-889), using the method given under General Methods item 6. The transgenic rice plants obtained which had been transformed with the plasmid pBA16 were referred to as Os-pBA16.

b) With Plant Expression Vectors Comprising Coding Nucleic Acid Sequences for a Protein Having the Activity of a GFAT-2 from Mouse Rice plants (cultivar M202) were transformed with the plant expression vector IC 386-299, which contains a coding nucleic acid sequence for a protein having the activity of a GFAT-2 from the mouse under the control of the promoter of the 13-kDa prolamin polypeptides from *Oryza sativa*, using the method given under General Methods item 6. The transgenic rice plants obtained which had been transformed with the plasmid pBA16 were referred to as GAOS0788.

15. Analysis of Rice Plants of the Line Os-pBA16 a) Immature Rice Seeds

Immature rice seeds (5 to 10 days after pollination) produced by individual plants of the line OS-pBA16, cultivated in soil in the greenhouse were collected, frozen in liquid nitrogen and stored at −80° C. Three frozen grains of each individual plant were selected randomly, the endosperm was squeezed out, pooled, weighted, and frozen in liquid nitrogen again. The sample was broken up with a Ball mill (Modell MM200, Firma Retsch, Germany), 100 µl Water was added, the homogenate was mixed, centrifuged (13000×g, 5 min) and the hyaluronan concentration of each sample was determined according to the method described under General Methods, item 4.

Out of 37 seed pools, each comprising 3 immature seeds from independent plants of line OS-pBA16 more than 70% proved to synthesize a significant amount of hyaluronan (at least 0.1 µg hyaluronan per g fresh weight) in seeds. The amount of hyaluronan in seed pools prepared from independent rice plants varied between 0.1 and 15.7 µg hyaluronan per g fresh weight. Results for seed pools each prepared from independent plants are shown in the following table:

TABLE 4

Detection of hyaluronan in seed pools, each prepared from independent plants of the transgenic line OS-pBA16.

| Plant material | Hyaluronan based on the fresh weight of the plant material [µg/g] |
|---|---|
| OS-pBA16 0612-00102 | 7.30 |
| OS-pBA16 0612-00102 | 0.54 |
| OS-pBA16 0612-00201 | 12.16 |
| OS-pBA16 0612-00401 | 1.12 |
| OS-pBA16 0612-00402 | 7.28 |
| OS-pBA16 0612-00502 | 0.08 |
| OS-pBA16 0612-00601 | 0.37 |
| OS-pBA16 0612-00701 | 0.66 |
| OS-pBA16 0612-00702 | 0.03 |
| OS-pBA16 0612-00801 | 2.48 |
| OS-pBA16 0612-00802 | 3.84 |
| OS-pBA16 0612-00902 | 0.02 |
| OS-pBA16 0612-01001 | 0.02 |
| OS-pBA16 0612-01201 | 1.71 |
| OS-pBA16 0612-01202 | 0.11 |
| OS-pBA16 0612-01301 | 5.84 |
| OS-pBA16 0612-01401 | 0.25 |
| OS-pBA16 0612-01402 | 0.11 |
| OS-pBA16 0612-01501 | 0.16 |
| OS-pBA16 0612-01601 | 1.12 |
| Wild type-1 | 0.01 |
| Wild type-2 | 0.02 |
| Wild type-3 | 0.02 |
| OS-pBA16 0613-00101 | 4.43 |
| OS-pBA16 0613-00102 | 1.95 |
| OS-pBA16 0613-00301 | 0.25 |
| OS-pBA16 0613-00401 | 15.72 |
| OS-pBA16 0613-00402 | 0.38 |
| OS-pBA16 0613-00502 | 0.87 |
| OS-pBA16 0613-00601 | 0.02 |
| OS-pBA16 0613-00602 | 0.01 |
| OS-pBA16 0613-00701 | 0.23 |
| OS-pBA16 0613-00702 | 0.80 |
| OS-pBA16 0613-00801 | 1.72 |
| OS-pBA16 0613-00802 | 0.15 |
| OS-pBA16 0613-00902 | 0.02 |
| OS-pBA16 0613-01001 | 0.02 |
| OS-pBA16 0613-01002 | 0.01 |
| OS-pBA16 0613-01102 | 0.24 |
| OS-pBA16 0613-01202 | 9.48 |
| OS-pBA16 0613-01301 | 13.44 |
| OS-pBA16 0613-01302 | 9.79 |
| OS-pBA16 0613-01501 | 0.63 |
| OS-pBA16 0613-01502 | 6.78 | b) Rice Flour 20-25 mature seeds were harvested from each transformed plant. Husks were removed by a dehusker (Laboratory Paddy sheller, Grainman, Miami, Fla., USA) and brown rice grain was milled with a laboratory mill (Cyclotec, Sample mill, Foss, Denmark). To about 40 mg of the obtained rice flour from the pooled seeds of each independent plant, 1 ml water was added, the sample was mixed, centrifuged (13000×g, 5 min) and the hyaluronan concentration of the supernatant of each sample was determined according to the method described under General Methods, item 4. Results for selected flour samples prepared from independent plants are shown in the following table:

TABLE 5

Detection of hyaluronan in rice flour samples, prepared from seeds of each independent plant of the transgenic line OS-pBA16.

| Plant material | Hyaluronan based on the weight of the plant material [µg/g] |
|---|---|
| OS-pBA16 0612-00101 | 2.03 |
| OS-pBA16 0612-00102 | 1.19 |
| OS-pBA16 0612-00201 | 1.94 |
| OS-pBA16 0612-00402 | 4.24 |
| OS-pBA16 0612-00502 | 1.19 |
| OS-pBA16 0612-00601 | 1.64 |
| OS-pBA16 0612-00602 | 2.51 |
| OS-pBA16 0612-00701 | 0.87 |
| OS-pBA16 0612-00702 | 1.04 |
| OS-pBA16 0612-00801 | 3.61 |
| OS-pBA16 0612-00802 | 3.88 |
| OS-pBA16 0612-00902 | 1.02 |
| OS-pBA16 0612-01001 | 0.58 |
| OS-pBA16 0612-01201 | 4.86 |
| OS-pBA16 0612-01202 | 2.96 |
| OS-pBA16 0612-01301 | 11.30 |
| OS-pBA16 0612-01401 | 1.64 |
| OS-pBA16 0612-01402 | 1.50 |
| OS-pBA16 0612-01501 | 4.54 |
| OS-pBA16 0612-01601 | 1.90 |
| OS-pBA16 0613-00101 | 3.46 |
| OS-pBA16 0613-00102 | 3.94 |
| OS-pBA16 0613-00301 | 3.32 |
| OS-pBA16 0613-00401 | 5.21 |
| OS-pBA16 0613-00402 | 3.45 |
| OS-pBA16 0613-00502 | 5.20 |
| OS-pBA16 0613-00601 | 0.83 |
| OS-pBA16 0613-00602 | 0.77 |
| OS-pBA16 0613-00701 | 2.63 |
| OS-pBA16 0613-00702 | 3.77 |
| OS-pBA16 0613-00801 | 1.55 |
| OS-pBA16 0613-00802 | 2.81 |
| OS-pBA16 0613-00902 | 2.65 |
| OS-pBA16 0613-01001 | 1.06 |
| OS-pBA16 0613-01002 | 0.59 |
| OS-pBA16 0613-01102 | 1.19 |
| OS-pBA16 0613-01202 | 10.18 |
| OS-pBA16 0613-01301 | 5.02 |
| OS-pBA16 0613-01302 | 3.84 |
| OS-pBA16 0613-01501 | 4.00 |
| OS-pBA16 0613-01502 | 5.63 |
| OS-pBA16 0613-000101 | 0.63 |
| OS-pBA16 0613-000103 | 0.58 |
| OS-pBA16 0613-000104 | 0.87 |

Detection was carried out using the method described under General Methods item 4.

b) Analysis of Rice Plants of the Line GAOS0788

Independent rice plants of the line GAOS0788 obtained after transformation with the plasmid IC 386-299 wre cultivated in soil in the greenhouse. From each plant 20-25 mature seeds (grains) were harvested, husks were removed by a dehusker (Laboratory Paddy sheller, Grainman, Miami, Fla., USA) and ca. 7 brown rice grains from each line were milled with a laboratory ball mill (MM200, Company Retsch, Germany, 30 sec. bei 30 HZ), leading to rice flour. Afterwards the content of N-acetylated glucosamin derivatives in each sample was determined according to the method as described by Elson and Morgan (1933, J. Biochem. 27, 1824). Several samples analysed did show an increase in the content of N-acetylated glucosamin derivatives ranging from ca. 2 µmol up to ca. 20 µmol N-acetylated glucosamin derivatives per gram fresh weight of the sample. Single grains of selected plants (GAOS0788-00501), analysed as described above, did show a content of N-acetylated glucosamin derivatives up to ca. 43 µmol per gram fresh weight of the sample.

Selected plants of the lines OS-pBA16 and GAOS0788 will be crossed with each other to obtain plants comprising nucleic acid molecules coding for a protein of a hyaluronan synthase and coding for a protein having the activity of a GFAT-2.

The invention claimed is:

1. A genetically modified potato plant cell comprising a nucleic acid molecule coding for a hyaluronan synthase stably integrated into its genome and a foreign nucleic acid molecule coding for a protein having the enzymatic activity of a glutamine:fructose 6-phosphate amidotransferase (GFAT), wherein said plant cell has an increased activity of a protein having the activity of a GFAT compared to corresponding non genetically modified wild-type plant cells, and wherein said cell synthesizes an increased amount of hyaluronan compared to a plant cell having the activity of a hyaluronan synthase and no increased activity of a GFAT.

2. A potato plant comprising the genetically modified potato plant cell of claim 1.

3. Propagation material comprising the genetically modified potato plant cell of claim 1.

4. Harvestable plant parts comprising the genetically modified potato plant cell of claim 1.

5. A process for preparing hyaluronan comprising extracting hyaluronan from the genetically modified potato plant cell of claim 1.

6. A composition comprising the genetically modified potato plant cell of claim 1.

7. A method for preparing a composition comprising hyaluronan comprising expressing hyaluronan in the genetically modified potato cell of claim 1.

8. The genetically modified plant cell of claim 1, wherein said foreign nucleic acid molecule coding for a protein having the activity of a GFAT comprises:
   a) a nucleic acid molecule coding for a protein comprising the amino acid sequence of SEQ ID NO: 5, SEQ ID NO: 7, or SEQ ID NO: 9;
   b) a nucleic acid molecule coding for a protein comprising a sequence at least 90%, 95%, or 98% identical to the amino acid sequence of SEQ ID NO: 5, SEQ ID NO: 7, or SEQ ID NO: 9;

c) a nucleic acid molecule comprising the nucleotide sequence of SEQ ID NO 4, SEQ ID NO: 6, SEQ ID NO: 8, SEQ ID NO: 10, or the sequence complementary thereto;

d) a nucleic acid molecule at least 90%, 95%, or 98% identical to the nucleic acid sequences described under a) or c); or e) a nucleic acid molecule which hybridizes under stringent conditions at least one strand of the nucleic acid sequences described under a) or c), wherein said stringent conditions comprises 25 M sodium phosphate buffer pH 7.2, 1 mM EDTA, 7% SDS, and 65-68° C.

9. A process for preparing hyaluronan comprising extracting hyaluronan from the potato plant of claim 2.

10. A process for preparing hyaluronan comprising extracting hyaluronan from the propagation material of claim 3.

11. A process for preparing hyaluronan comprising extracting hyaluronan from the harvestable plant parts of claim 4.

12. A potato plant comprising the genetically modified potato plant cell of claim 8.

13. Propagation material comprising the genetically modified potato plant cell of claim 8.

14. Harvestable plant parts comprising the genetically modified potato plant cell of claim 8.

* * * * *

SEQUENCE LISTING

<160> NUMBER OF SEQ ID NOS: 14

<210> SEQ ID NO 1
<211> LENGTH: 1707
<212> TYPE: DNA
<213> ORGANISM: Paramecium bursaria Chlorella Virus 1
<220> FEATURE:
<221> NAME/KEY: CDS
<222> LOCATION: (1)..(1707)
<300> PUBLICATION INFORMATION:
<308> DATABASE ACCESSION NUMBER: PB42580
<309> DATABASE ENTRY DATE: 1995-12-24
<313> RELEVANT RESIDUES IN SEQ ID NO: (50903)..(52609)

<400> SEQUENCE: 1

```
atg ggt aaa aat ata atc ata atg gtt tcg tgg tac acc atc ata act       48
Met Gly Lys Asn Ile Ile Ile Met Val Ser Trp Tyr Thr Ile Ile Thr
1               5                   10                  15 tca aat cta atc gcg gtt gga gga gcc tct cta atc ttg gct ccg gca       96
Ser Asn Leu Ile Ala Val Gly Gly Ala Ser Leu Ile Leu Ala Pro Ala
                20                  25                  30 att act ggg tat gtt cta cat tgg aat att gct ctc tcg aca atc tgg      144
Ile Thr Gly Tyr Val Leu His Trp Asn Ile Ala Leu Ser Thr Ile Trp
            35                  40                  45
```

```
gga gta tca gct tat ggt att ttc gtt ttt ggg ttt ttc ctt gca caa    192
Gly Val Ser Ala Tyr Gly Ile Phe Val Phe Gly Phe Phe Leu Ala Gln
 50              55                  60 gtt tta ttt tca gaa ctg aac agg aaa cgt ctt cgc aag tgg att tct    240
Val Leu Phe Ser Glu Leu Asn Arg Lys Arg Leu Arg Lys Trp Ile Ser
 65              70                  75                  80 ctc aga cct aag ggt tgg aat gat gtt cgt ttg gct gtg atc att gct    288
Leu Arg Pro Lys Gly Trp Asn Asp Val Arg Leu Ala Val Ile Ile Ala
                 85                  90                  95 gga tat cgc gag gat cct tat atg ttc cag aag tgc ctc gag tct gta    336
Gly Tyr Arg Glu Asp Pro Tyr Met Phe Gln Lys Cys Leu Glu Ser Val
            100                 105                 110 cgt gac tct gat tat ggc aac gtt gcc cgt ctg att tgt gtg att gac    384
Arg Asp Ser Asp Tyr Gly Asn Val Ala Arg Leu Ile Cys Val Ile Asp
        115                 120                 125 ggt gat gag gac gat gat atg agg atg gct gcc gtt tac aag gcg atc    432
Gly Asp Glu Asp Asp Asp Met Arg Met Ala Ala Val Tyr Lys Ala Ile
130                 135                 140 tac aat gat aat atc aag aag ccc gag ttt gtt ctg tgt gag tca gac    480
Tyr Asn Asp Asn Ile Lys Lys Pro Glu Phe Val Leu Cys Glu Ser Asp
145                 150                 155                 160 gac aag gaa ggt gaa cgc atc gac tct gat ttc tct cgc gac att tgt    528
Asp Lys Glu Gly Glu Arg Ile Asp Ser Asp Phe Ser Arg Asp Ile Cys
                165                 170                 175 gtc ctc cag cct cat cgt gga aaa cgg gag tgt ctt tat act ggg ttt    576
Val Leu Gln Pro His Arg Gly Lys Arg Glu Cys Leu Tyr Thr Gly Phe
            180                 185                 190 caa ctt gca aag atg gac ccc agt gtc aat gct gtc gtt ctg att gac    624
Gln Leu Ala Lys Met Asp Pro Ser Val Asn Ala Val Val Leu Ile Asp
        195                 200                 205 agc gat acc gtt ctc gag aag gat gct att ctg gaa gtt gta tac cca    672
Ser Asp Thr Val Leu Glu Lys Asp Ala Ile Leu Glu Val Val Tyr Pro
210                 215                 220 ctt gca tgc gat ccc gag atc caa gcc gtt gca ggt gag tgt aag att    720
Leu Ala Cys Asp Pro Glu Ile Gln Ala Val Ala Gly Glu Cys Lys Ile
225                 230                 235                 240 tgg aac aca gac act ctt ttg agt ctt ctc gtc gct tgg cgg tac tat    768
Trp Asn Thr Asp Thr Leu Leu Ser Leu Leu Val Ala Trp Arg Tyr Tyr
                245                 250                 255 tct gcg ttt tgt gtg gag agg agt gcc cag tct ttt ttc agg act gtt    816
Ser Ala Phe Cys Val Glu Arg Ser Ala Gln Ser Phe Phe Arg Thr Val
            260                 265                 270 cag tgc gtt ggg ggg cca ctg ggt gcc tac aag att gat atc att aag    864
Gln Cys Val Gly Gly Pro Leu Gly Ala Tyr Lys Ile Asp Ile Ile Lys
        275                 280                 285 gag att aag gac ccc tgg att tcc cag cgc ttt ctt ggt cag aag tgt    912
Glu Ile Lys Asp Pro Trp Ile Ser Gln Arg Phe Leu Gly Gln Lys Cys
290                 295                 300 act tac ggt gac gac cgc cgg cta acc aac gag atc ttg atg cgt ggt    960
Thr Tyr Gly Asp Asp Arg Arg Leu Thr Asn Glu Ile Leu Met Arg Gly
305                 310                 315                 320 aaa aag gtt gtg ttc act cca ttt gct gtt ggt tgg tct gac agt ccg   1008
Lys Lys Val Val Phe Thr Pro Phe Ala Val Gly Trp Ser Asp Ser Pro
                325                 330                 335 acc aat gtg ttt cgg tac atc gtt cag cag acc cgc tgg agt aag tcg   1056
Thr Asn Val Phe Arg Tyr Ile Val Gln Gln Thr Arg Trp Ser Lys Ser
            340                 345                 350 tgg tgc cgc gaa att tgg tac acc ctc ttc gcc gcg tgg aag cac ggt   1104
Trp Cys Arg Glu Ile Trp Tyr Thr Leu Phe Ala Ala Trp Lys His Gly
```

```
                 355                 360                 365
ttg tct gga att tgg ctg gcc ttt gaa tgt ttg tat caa att aca tac      1152
Leu Ser Gly Ile Trp Leu Ala Phe Glu Cys Leu Tyr Gln Ile Thr Tyr
    370                 375                 380 ttc ttc ctc gtg att tac ctc ttt tct cgc cta gcc gtt gag gcc gac      1200
Phe Phe Leu Val Ile Tyr Leu Phe Ser Arg Leu Ala Val Glu Ala Asp
385                 390                 395                 400 cct cgc gcc cag aca gcc acg gtg att gtg agc acc acg gtt gca ttg      1248
Pro Arg Ala Gln Thr Ala Thr Val Ile Val Ser Thr Thr Val Ala Leu
                405                 410                 415 att aag tgt ggg tat ttt tca ttc cga gcc aag gat att cgg gcg ttt      1296
Ile Lys Cys Gly Tyr Phe Ser Phe Arg Ala Lys Asp Ile Arg Ala Phe
            420                 425                 430 tac ttt gtg ctt tat aca ttt gtt tac ttt ttc tgt atg att ccg gcc      1344
Tyr Phe Val Leu Tyr Thr Phe Val Tyr Phe Phe Cys Met Ile Pro Ala
        435                 440                 445 agg att act gca atg atg acg ctt tgg gac att ggc tgg ggt act cgc      1392
Arg Ile Thr Ala Met Met Thr Leu Trp Asp Ile Gly Trp Gly Thr Arg
    450                 455                 460 ggt gga aac gag aag cct tcc gtt ggc acc cgg gtc gct ctg tgg gca      1440
Gly Gly Asn Glu Lys Pro Ser Val Gly Thr Arg Val Ala Leu Trp Ala
465                 470                 475                 480 aag caa tat ctc att gca tat atg tgg tgg gcc gcg gtt gtt ggc gct      1488
Lys Gln Tyr Leu Ile Ala Tyr Met Trp Trp Ala Ala Val Val Gly Ala
                485                 490                 495 gga gtt tac agc atc gtc cat aac tgg atg ttc gat tgg aat tct ctt      1536
Gly Val Tyr Ser Ile Val His Asn Trp Met Phe Asp Trp Asn Ser Leu
            500                 505                 510 tct tat cgt ttt gct ttg gtt ggt att tgt tct tac att gtt ttt att      1584
Ser Tyr Arg Phe Ala Leu Val Gly Ile Cys Ser Tyr Ile Val Phe Ile
        515                 520                 525 gtt att gtg ctg gtg gtt tat ttc acc ggc aaa att acg act tgg aat      1632
Val Ile Val Leu Val Val Tyr Phe Thr Gly Lys Ile Thr Thr Trp Asn
    530                 535                 540 ttc acg aag ctt cag aag gag cta atc gag gat cgc gtt ctg tac gat      1680
Phe Thr Lys Leu Gln Lys Glu Leu Ile Glu Asp Arg Val Leu Tyr Asp
545                 550                 555                 560 gca act acc aat gct cag tct gtg tga                                  1707
Ala Thr Thr Asn Ala Gln Ser Val
                565

<210> SEQ ID NO 2
<211> LENGTH: 568
<212> TYPE: PRT
<213> ORGANISM: Paramecium bursaria Chlorella Virus 1

<400> SEQUENCE: 2

Met Gly Lys Asn Ile Ile Met Val Ser Trp Tyr Thr Ile Thr
1               5                   10                  15

Ser Asn Leu Ile Ala Val Gly Gly Ala Ser Leu Ile Leu Ala Pro Ala
                20                  25                  30

Ile Thr Gly Tyr Val Leu His Trp Asn Ile Ala Leu Ser Thr Ile Trp
            35                  40                  45

Gly Val Ser Ala Tyr Gly Ile Phe Val Phe Gly Phe Phe Leu Ala Gln
        50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95
```

-continued

```
Gly Tyr Arg Glu Asp Pro Tyr Met Phe Gln Lys Cys Leu Glu Ser Val
                100                 105                 110

Arg Asp Ser Asp Tyr Gly Asn Val Ala Arg Leu Ile Cys Val Ile Asp
            115                 120                 125

Gly Asp Glu Asp Asp Met Arg Met Ala Ala Val Tyr Lys Ala Ile
130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
    210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Ile Asp Ile Ile Lys
        275                 280                 285

Glu Ile Lys Asp Pro Trp Ile Ser Gln Arg Phe Leu Gly Gln Lys Cys
    290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
        355                 360                 365

Leu Ser Gly Ile Trp Leu Ala Phe Glu Cys Leu Tyr Gln Ile Thr Tyr
    370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Thr Val Ala Leu
                405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Cys Met Ile Pro Ala
        435                 440                 445

Arg Ile Thr Ala Met Met Thr Leu Trp Asp Ile Gly Trp Gly Thr Arg
    450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Ala Val Val Gly Ala
                485                 490                 495

Gly Val Tyr Ser Ile Val His Asn Trp Met Phe Asp Trp Asn Ser Leu
            500                 505                 510
```

```
Ser Tyr Arg Phe Ala Leu Val Gly Ile Cys Ser Tyr Ile Val Phe Ile
            515                 520                 525

Val Ile Val Leu Val Val Tyr Phe Thr Gly Lys Ile Thr Thr Trp Asn
    530                 535                 540

Phe Thr Lys Leu Gln Lys Glu Leu Ile Glu Asp Arg Val Leu Tyr Asp
545                 550                 555                 560

Ala Thr Thr Asn Ala Gln Ser Val
                565
```

<210> SEQ ID NO 3
<211> LENGTH: 1707
<212> TYPE: DNA
<213> ORGANISM: Artificial Sequence
<220> FEATURE:
<223> OTHER INFORMATION: Synthetic sequence encoding a Paramecium bursaria Chlorella Virus Hyaluronansynthase protein

<400> SEQUENCE: 3

| | | | | | |
|---|---|---|---|---|---|
| atgggtaaga | acattatcat | tatggtgtcc | tggtacacaa | ttattacaag | taatctcatc | 60 |
| gcagttggtg | gtgcatctct | tattctcgct | ccagctatca | ctggatatgt | tcttcactgg | 120 |
| aacatcgccc | tctcaactat | tggggagtt | tccgcatatg | gtattttgt | tttcgggttc | 180 |
| ttttggctc | aggttctgtt | ctcagagctc | aatcgtaaga | gactcaggaa | gtggattagc | 240 |
| cttagaccaa | aggggtggaa | tgacgttcgt | ctcgctgtca | ttatcgctgg | ctaccgtgaa | 300 |
| gatccttaca | tgtttcaaaa | gtgcttggaa | tcagttaggg | atagtgatta | tggcaacgtc | 360 |
| gctagactga | tctgtgtgat | tgatggagat | gaggacgacg | atatgaggat | ggcagctgtt | 420 |
| tataaggcta | tctataatga | taacattaag | aagcctgaat | tgttctttg | cgagtctgat | 480 |
| gacaaggaag | gagaacggat | tgattcagat | ttctcacgtg | atatctgcgt | tctccaacct | 540 |
| catcgtggga | agcgtgaatg | tctttataca | ggtttccaac | tcgccaaaat | ggacccatca | 600 |
| gtgaacgctg | tggttcttat | cgatagtgat | actgtgctgg | agaaagatgc | tatcttggag | 660 |
| gttgtttacc | ctcttgcctg | tgatcctgaa | attcaagctg | tggctggaga | gtgcaagatc | 720 |
| tggaacacag | atactcttct | ttctctgctt | gtcgcatgga | gatattactc | cgcattctgt | 780 |
| gtggagagga | gcgctcaatc | cttttttccgt | accgttcaat | gcgttggtgg | tccttttgga | 840 |
| gcttacaaaa | ttgatatcat | caaggagatt | aaggacccat | ggattagtca | aggtttctt | 900 |
| ggtcagaagt | gcacttatgg | cgatgatcgt | agattgacta | cgaaatcct | tatgagggc | 960 |
| aagaaagtcg | ttttactcc | atttgctgtc | ggatggtctg | attcacctac | aaatgttttc | 1020 |
| cgttatattg | tgcaacaaac | acgttggagt | aagagctggt | gtagggagat | ctggtacact | 1080 |
| tgttcgctg | cttggaagca | cgggcttagc | ggaatttggc | ttgcttttga | atgcctttac | 1140 |
| cagattacat | actttttctt | ggtgatctat | ttgttttcac | gtcttgccgt | cgaggctgac | 1200 |
| cctagagcac | agactgcaac | tgtgattgtt | tctactacag | tcgcacttat | taagtgtggc | 1260 |
| tatttcagtt | ttagagcaaa | agatattaga | gccttctatt | ttgttttgta | cacatttgtt | 1320 |
| tatttctttt | gcatgattcc | agctcgtatt | accgctatga | tgaccttgtg | ggacatcgga | 1380 |
| tggggaacta | gaggtggtaa | cgaaaagcct | tctgtgggaa | caagggtggc | cctttgggca | 1440 |
| aaacaatatc | tcatcgccta | catgtggtgg | gccgctgtcg | ttggtgccgg | agtgtactca | 1500 |
| atcgttcata | actggatgtt | tgactggaac | tctttgagct | atcgtttcgc | tcttgtgggt | 1560 |
| atttgttctt | acattgtttt | catcgtgatt | gtgctcgttg | tgtatttcac | tggtaaaatc | 1620 |
| acaacctgga | atttcactaa | acttcaaaag | gaattgattg | aagacagggt | tctgtatgat | 1680 |

-continued

```
gctactacca acgcccagtc agtttaa                                          1707
```

<210> SEQ ID NO 4
<211> LENGTH: 2298
<212> TYPE: DNA
<213> ORGANISM: Mus musculus
<220> FEATURE:
<221> NAME/KEY: CDS
<222> LOCATION: (150)..(2192)
<220> FEATURE:
<221> NAME/KEY: allele
<222> LOCATION: (1190)..(1190)
<223> OTHER INFORMATION: sequnce inserted in plasmid IC 365-256 contains
      a base exchnage from T to C at position 1190
<220> FEATURE:
<221> NAME/KEY: allele
<222> LOCATION: (2027)..(2027)
<223> OTHER INFORMATION: sequnce inserted in plasmid IC 365-256 contains
      a base exchnage from G to A at position 2027
<300> PUBLICATION INFORMATION:
<308> DATABASE ACCESSION NUMBER: BC050762.1
<309> DATABASE ENTRY DATE: 2005-03-08
<313> RELEVANT RESIDUES IN SEQ ID NO: (150)..(2195)

<400> SEQUENCE: 4

```
gagagcgaag cgagcgctga gtcggactgt cgggtctgag ctgtcgcatc ccagagtcct         60
ctcattgcca ccaccccggc ccgagctcac cctcgcttct gaagctctcc gcgcgcccga        120
cagctcagcc ctcgcccgtg accaacatc atg tgc ggt ata ttt gct tat tta         173
                                Met Cys Gly Ile Phe Ala Tyr Leu
                                 1               5 aat tac cat gtt cct cga aca aga cga gaa atc ttg gag aca cta atc         221
Asn Tyr His Val Pro Arg Thr Arg Arg Glu Ile Leu Glu Thr Leu Ile
    10                  15                  20 aaa ggc ctt cag aga ctg gaa tac aga gga tat gat tct gct ggt gtg         269
Lys Gly Leu Gln Arg Leu Glu Tyr Arg Gly Tyr Asp Ser Ala Gly Val
25                  30                  35                  40 gga ctt gac gga ggc aat gac aaa gac tgg gaa gcc aac gcc tgc aaa         317
Gly Leu Asp Gly Gly Asn Asp Lys Asp Trp Glu Ala Asn Ala Cys Lys
                45                  50                  55 atc cag ctc att aag aag aaa gga aaa gtt aag gca ctg gat gaa gaa         365
Ile Gln Leu Ile Lys Lys Lys Gly Lys Val Lys Ala Leu Asp Glu Glu
            60                  65                  70 gtt cac aaa caa caa gat atg gac ttg gat ata gaa ttt gat gtg cat         413
Val His Lys Gln Gln Asp Met Asp Leu Asp Ile Glu Phe Asp Val His
        75                  80                  85 ctt gga ata gct cat acc cgt tgg gcg aca cat gga gaa ccc aat cct         461
Leu Gly Ile Ala His Thr Arg Trp Ala Thr His Gly Glu Pro Asn Pro
    90                  95                 100 gtc aat agt cac ccc cag cgc tct gat aaa aat aat gaa ttc att gtt         509
Val Asn Ser His Pro Gln Arg Ser Asp Lys Asn Asn Glu Phe Ile Val
105                 110                 115                 120 att cat aat gga atc atc acc aac tac aaa gac ttg aaa aag ttt ctg         557
Ile His Asn Gly Ile Ile Thr Asn Tyr Lys Asp Leu Lys Lys Phe Leu
                125                 130                 135 gaa agc aaa ggc tat gac ttt gaa tct gaa aca gac aca gaa acc att         605
Glu Ser Lys Gly Tyr Asp Phe Glu Ser Glu Thr Asp Thr Glu Thr Ile
            140                 145                 150 gcc aag ctc gtc aag tac atg tat gac aac tgg gag agc cag gac gtc         653
Ala Lys Leu Val Lys Tyr Met Tyr Asp Asn Trp Glu Ser Gln Asp Val
        155                 160                 165 agt ttt acc acc ttg gtg gag aga gtt atc caa caa ttg gaa ggc gcc         701
Ser Phe Thr Thr Leu Val Glu Arg Val Ile Gln Gln Leu Glu Gly Ala
    170                 175                 180
```

-continued

| | | |
|---|---|---|
| ttt gct ctt gtg ttt aaa agt gtc cat ttt ccc ggg caa gca gtt ggc<br>Phe Ala Leu Val Phe Lys Ser Val His Phe Pro Gly Gln Ala Val Gly<br>185                            190                      195                         200 | | 749 |
| aca agg cga ggt agc cct ctc ttg att ggt gtg cgg agt gaa cat aag<br>Thr Arg Arg Gly Ser Pro Leu Leu Ile Gly Val Arg Ser Glu His Lys<br>                    205                      210                      215 | | 797 |
| ctt tct aca gat cac att ccg att ctg tac aga aca ggc aaa gac aag<br>Leu Ser Thr Asp His Ile Pro Ile Leu Tyr Arg Thr Gly Lys Asp Lys<br>                        220                      225                      230 | | 845 |
| aaa gga agc tgc ggt ctt tcc cgt gtg gac agc acg aca tgc ctg ttc<br>Lys Gly Ser Cys Gly Leu Ser Arg Val Asp Ser Thr Thr Cys Leu Phe<br>         235                      240                      245 | | 893 |
| cct gtt gag gaa aag gca gtt gaa tat tac ttt gct tct gat gca agt<br>Pro Val Glu Glu Lys Ala Val Glu Tyr Tyr Phe Ala Ser Asp Ala Ser<br>        250                      255                      260 | | 941 |
| gcc gtg ata gag cac acc aat cgt gtc atc ttt ctg gaa gat gat gat<br>Ala Val Ile Glu His Thr Asn Arg Val Ile Phe Leu Glu Asp Asp Asp<br>265                            270                      275                         280 | | 989 |
| gtt gca gca gtg gtg gat ggc cgt ctc tct atc cac cga att aaa cga<br>Val Ala Ala Val Val Asp Gly Arg Leu Ser Ile His Arg Ile Lys Arg<br>                        285                      290                      295 | | 1037 |
| act gca gga gac cat cct ggc cga gct gtg caa act ctc cag atg gag<br>Thr Ala Gly Asp His Pro Gly Arg Ala Val Gln Thr Leu Gln Met Glu<br>        300                      305                      310 | | 1085 |
| ctc cag cag atc atg aag ggc aac ttt agt tca ttt atg cag aag gaa<br>Leu Gln Gln Ile Met Lys Gly Asn Phe Ser Ser Phe Met Gln Lys Glu<br>                315                      320                      325 | | 1133 |
| att ttt gag cag cca gaa tct gtt gtg aac aca atg aga gga aga gtc<br>Ile Phe Glu Gln Pro Glu Ser Val Val Asn Thr Met Arg Gly Arg Val<br>330                            335                      340 | | 1181 |
| aat ttt gat gac tac act gtg aat ttg gga ggt ttg aaa gat cac att<br>Asn Phe Asp Asp Tyr Thr Val Asn Leu Gly Gly Leu Lys Asp His Ile<br>345                            350                      355                        360 | | 1229 |
| aag gag atc cag cgg tgt cgg cgg ttg att ctt att gct tgt ggc aca<br>Lys Glu Ile Gln Arg Cys Arg Arg Leu Ile Leu Ile Ala Cys Gly Thr<br>                        365                      370                      375 | | 1277 |
| agt tac cac gct ggt gtg gca acc cgt cag gtc ctg gag gag ctg acc<br>Ser Tyr His Ala Gly Val Ala Thr Arg Gln Val Leu Glu Glu Leu Thr<br>        380                      385                      390 | | 1325 |
| gag ctg ccc gtg atg gtg gag ctt gcc agt gac ttc ttg gat aga aac<br>Glu Leu Pro Val Met Val Glu Leu Ala Ser Asp Phe Leu Asp Arg Asn<br>                395                      400                      405 | | 1373 |
| act cca gtc ttt cga gat gat gtt tgc ttt ttc att agt caa tca ggc<br>Thr Pro Val Phe Arg Asp Asp Val Cys Phe Phe Ile Ser Gln Ser Gly<br>410                            415                      420 | | 1421 |
| gag aca gct gac acc ctg atg gga ctt cgt tac tgt aag gag aga gga<br>Glu Thr Ala Asp Thr Leu Met Gly Leu Arg Tyr Cys Lys Glu Arg Gly<br>425                            430                      435                      440 | | 1469 |
| gcc tta act gtg ggg atc aca aat aca gtc ggc agt tct ata tca agg<br>Ala Leu Thr Val Gly Ile Thr Asn Thr Val Gly Ser Ser Ile Ser Arg<br>                        445                      450                      455 | | 1517 |
| gag aca gat tgc ggg gtt cat att aat gct ggt cct gag att ggc gtg<br>Glu Thr Asp Cys Gly Val His Ile Asn Ala Gly Pro Glu Ile Gly Val<br>        460                      465                      470 | | 1565 |
| gcc agt aca aag gca tac acc agc cag ttt gtg tcc ctc gtg atg ttt<br>Ala Ser Thr Lys Ala Tyr Thr Ser Gln Phe Val Ser Leu Val Met Phe<br>475                            480                      485 | | 1613 |
| gct ctc atg atg tgt gat gac agg atc tcc atg caa gag aga cgc aaa<br>Ala Leu Met Met Cys Asp Asp Arg Ile Ser Met Gln Glu Arg Arg Lys<br>490                            495                      500 | | 1661 |

```
gag atc atg ctc gga ctg aag cga ctg ccg gac ttg att aag gaa gtg      1709
Glu Ile Met Leu Gly Leu Lys Arg Leu Pro Asp Leu Ile Lys Glu Val
505                 510                 515                 520 ctg agc atg gat gat gaa atc cag aag ctg gcg acg gag ctt tac cac      1757
Leu Ser Met Asp Asp Glu Ile Gln Lys Leu Ala Thr Glu Leu Tyr His
                525                 530                 535 cag aag tcg gtc ctg ata atg ggg cgg ggc tac cat tat gct aca tgc      1805
Gln Lys Ser Val Leu Ile Met Gly Arg Gly Tyr His Tyr Ala Thr Cys
            540                 545                 550 ctt gaa ggg gct ctg aaa atc aag gag att act tat atg cat tcg gaa      1853
Leu Glu Gly Ala Leu Lys Ile Lys Glu Ile Thr Tyr Met His Ser Glu
        555                 560                 565 ggc atc ctt gct ggt gag ctc aag cac ggc cct ctg gcc ttg gtg gac      1901
Gly Ile Leu Ala Gly Glu Leu Lys His Gly Pro Leu Ala Leu Val Asp
    570                 575                 580 aag ttg atg cct gtc atc atg atc atc atg cga gac cac act tat gcc      1949
Lys Leu Met Pro Val Ile Met Ile Ile Met Arg Asp His Thr Tyr Ala
585                 590                 595                 600 aag tgc cag aac gct ctt cag cag gtg gtt gca cgg cag ggg cgt cca      1997
Lys Cys Gln Asn Ala Leu Gln Gln Val Val Ala Arg Gln Gly Arg Pro
                605                 610                 615 gtc gtg atc tgt gat aag gag gat act gag acc att aag aat aca aaa      2045
Val Val Ile Cys Asp Lys Glu Asp Thr Glu Thr Ile Lys Asn Thr Lys
            620                 625                 630 agg aca atc aag gtg ccc cac tca gtg gac tgc ttg cag ggc att ctc      2093
Arg Thr Ile Lys Val Pro His Ser Val Asp Cys Leu Gln Gly Ile Leu
        635                 640                 645 agt gtg att ccc ctg cag ctg ctg gct ttc cac ctg gct gtg ctg aga      2141
Ser Val Ile Pro Leu Gln Leu Leu Ala Phe His Leu Ala Val Leu Arg
    650                 655                 660 ggc tac gat gtt gat ttt cca cgg aat ctt gcc aaa tct gta aca gta      2189
Gly Tyr Asp Val Asp Phe Pro Arg Asn Leu Ala Lys Ser Val Thr Val
665                 670                 675                 680 gag taacagacac ctgaaactta agacagttaa gcaacacgag ataccttttg            2242
Glu tatttaaatt tttgatttaa actatcaaaa aaaaaaaaaa aaaaaaaaaa aaaaaa         2298

<210> SEQ ID NO 5
<211> LENGTH: 681
<212> TYPE: PRT
<213> ORGANISM: Mus musculus

<400> SEQUENCE: 5

Met Cys Gly Ile Phe Ala Tyr Leu Asn Tyr His Val Pro Arg Thr Arg
1               5                   10                  15

Arg Glu Ile Leu Glu Thr Leu Ile Lys Gly Leu Gln Arg Leu Glu Tyr
            20                  25                  30

Arg Gly Tyr Asp Ser Ala Gly Val Gly Leu Asp Gly Gly Asn Asp Lys
        35                  40                  45

Asp Trp Glu Ala Asn Ala Cys Lys Ile Gln Leu Ile Lys Lys Lys Gly
    50                  55                  60

Lys Val Lys Ala Leu Asp Glu Glu Val His Lys Gln Gln Asp Met Asp
65                  70                  75                  80

Leu Asp Ile Glu Phe Asp Val His Leu Gly Ile Ala His Thr Arg Trp
                85                  90                  95

Ala Thr His Gly Glu Pro Asn Pro Val Asn Ser His Pro Gln Arg Ser
            100                 105                 110
```

-continued

Asp Lys Asn Asn Glu Phe Ile Val Ile His Asn Gly Ile Ile Thr Asn
            115                 120                 125

Tyr Lys Asp Leu Lys Lys Phe Leu Glu Ser Lys Gly Tyr Asp Phe Glu
    130                 135                 140

Ser Glu Thr Asp Thr Glu Thr Ile Ala Lys Leu Val Lys Tyr Met Tyr
145                 150                 155                 160

Asp Asn Trp Glu Ser Gln Asp Val Ser Phe Thr Thr Leu Val Glu Arg
                165                 170                 175

Val Ile Gln Gln Leu Glu Gly Ala Phe Ala Leu Val Phe Lys Ser Val
            180                 185                 190

His Phe Pro Gly Gln Ala Val Gly Thr Arg Arg Gly Ser Pro Leu Leu
    195                 200                 205

Ile Gly Val Arg Ser Glu His Lys Leu Ser Thr Asp His Ile Pro Ile
210                 215                 220

Leu Tyr Arg Thr Gly Lys Asp Lys Lys Gly Ser Cys Gly Leu Ser Arg
225                 230                 235                 240

Val Asp Ser Thr Thr Cys Leu Phe Pro Val Glu Glu Lys Ala Val Glu
                245                 250                 255

Tyr Tyr Phe Ala Ser Asp Ala Ser Ala Val Ile Glu His Thr Asn Arg
            260                 265                 270

Val Ile Phe Leu Glu Asp Asp Val Ala Ala Val Asp Gly Arg
    275                 280                 285

Leu Ser Ile His Arg Ile Lys Arg Thr Ala Gly Asp His Pro Gly Arg
    290                 295                 300

Ala Val Gln Thr Leu Gln Met Glu Leu Gln Gln Ile Met Lys Gly Asn
305                 310                 315                 320

Phe Ser Ser Phe Met Gln Lys Glu Ile Phe Glu Gln Pro Glu Ser Val
                325                 330                 335

Val Asn Thr Met Arg Gly Arg Val Asn Phe Asp Asp Tyr Thr Val Asn
            340                 345                 350

Leu Gly Gly Leu Lys Asp His Ile Lys Glu Ile Gln Arg Cys Arg Arg
    355                 360                 365

Leu Ile Leu Ile Ala Cys Gly Thr Ser Tyr His Ala Gly Val Ala Thr
    370                 375                 380

Arg Gln Val Leu Glu Glu Leu Thr Glu Leu Pro Val Met Val Glu Leu
385                 390                 395                 400

Ala Ser Asp Phe Leu Asp Arg Asn Thr Pro Val Phe Arg Asp Asp Val
                405                 410                 415

Cys Phe Phe Ile Ser Gln Ser Gly Glu Thr Ala Asp Thr Leu Met Gly
            420                 425                 430

Leu Arg Tyr Cys Lys Glu Arg Gly Ala Leu Thr Val Gly Ile Thr Asn
    435                 440                 445

Thr Val Gly Ser Ser Ile Ser Arg Glu Thr Asp Cys Gly Val His Ile
450                 455                 460

Asn Ala Gly Pro Glu Ile Gly Val Ala Ser Thr Lys Ala Tyr Thr Ser
465                 470                 475                 480

Gln Phe Val Ser Leu Val Met Phe Ala Leu Met Met Cys Asp Asp Arg
                485                 490                 495

Ile Ser Met Gln Glu Arg Arg Lys Glu Ile Met Leu Gly Leu Lys Arg
            500                 505                 510

Leu Pro Asp Leu Ile Lys Glu Val Leu Ser Met Asp Asp Glu Ile Gln
    515                 520                 525

Lys Leu Ala Thr Glu Leu Tyr His Gln Lys Ser Val Leu Ile Met Gly

```
                    530                 535                 540
Arg Gly Tyr His Tyr Ala Thr Cys Leu Glu Gly Ala Leu Lys Ile Lys
545                 550                 555                 560

Glu Ile Thr Tyr Met His Ser Glu Gly Ile Leu Ala Gly Glu Leu Lys
                565                 570                 575

His Gly Pro Leu Ala Leu Val Asp Lys Leu Met Pro Val Ile Met Ile
            580                 585                 590

Ile Met Arg Asp His Thr Tyr Ala Lys Cys Gln Asn Ala Leu Gln Gln
        595                 600                 605

Val Val Ala Arg Gln Gly Arg Pro Val Val Ile Cys Asp Lys Glu Asp
    610                 615                 620

Thr Glu Thr Ile Lys Asn Thr Lys Arg Thr Ile Lys Val Pro His Ser
625                 630                 635                 640

Val Asp Cys Leu Gln Gly Ile Leu Ser Val Ile Pro Leu Gln Leu Leu
                645                 650                 655

Ala Phe His Leu Ala Val Leu Arg Gly Tyr Asp Val Asp Phe Pro Arg
            660                 665                 670

Asn Leu Ala Lys Ser Val Thr Val Glu
        675                 680

<210> SEQ ID NO 6
<211> LENGTH: 2049
<212> TYPE: DNA
<213> ORGANISM: Mus musculus
<220> FEATURE:
<221> NAME/KEY: CDS
<222> LOCATION: (1)..(2046)
<300> PUBLICATION INFORMATION:
<308> DATABASE ACCESSION NUMBER: BC031928.1
<309> DATABASE ENTRY DATE: 2003-10-07
<313> RELEVANT RESIDUES IN SEQ ID NO: (51)..(299)

<400> SEQUENCE: 6 atg tgc gga atc ttt gcc tac atg aat tac aga gtt ccc aag aca agg      48
Met Cys Gly Ile Phe Ala Tyr Met Asn Tyr Arg Val Pro Lys Thr Arg
1               5                   10                  15 aaa gag att ttc gaa acc ctt atc agg ggt ctg cag cgg ctg gag tac      96
Lys Glu Ile Phe Glu Thr Leu Ile Arg Gly Leu Gln Arg Leu Glu Tyr
                20                  25                  30 cgg ggc tat gac tct gcg ggg gtt gcc att gat ggg aat aac cac gaa     144
Arg Gly Tyr Asp Ser Ala Gly Val Ala Ile Asp Gly Asn Asn His Glu
            35                  40                  45 gtc aaa gaa aga cac atc cat ctt gtg aag aaa agg ggg aaa gta aag     192
Val Lys Glu Arg His Ile His Leu Val Lys Lys Arg Gly Lys Val Lys
50                  55                  60 gct ctg gat gaa gaa ctt tac aag caa gat agc atg gac ttg aag gtg     240
Ala Leu Asp Glu Glu Leu Tyr Lys Gln Asp Ser Met Asp Leu Lys Val
65                  70                  75                  80 gag ttt gag aca cac ttc ggc att gcc cac aca cgt tgg gcc acc cac     288
Glu Phe Glu Thr His Phe Gly Ile Ala His Thr Arg Trp Ala Thr His
                85                  90                  95 ggg gtt ccc aat gct gtc aac agt cac ccg cag cgt tcg gac aaa gac     336
Gly Val Pro Asn Ala Val Asn Ser His Pro Gln Arg Ser Asp Lys Asp
            100                 105                 110 aat gaa ttt gtt gtc atc cac aac ggg atc atc act aat tac aag gat     384
Asn Glu Phe Val Val Ile His Asn Gly Ile Ile Thr Asn Tyr Lys Asp
        115                 120                 125 cta agg aag ttt ctg gaa agc aaa ggc tac gag ttt gag tca gaa aca     432
Leu Arg Lys Phe Leu Glu Ser Lys Gly Tyr Glu Phe Glu Ser Glu Thr
    130                 135                 140
```

```
gac acg gag acc atc gcc aag ctg att aaa tat gta ttt gac aac aga      480
Asp Thr Glu Thr Ile Ala Lys Leu Ile Lys Tyr Val Phe Asp Asn Arg
145                 150                 155                 160 gag act gag gac ata acg ttt tcc aca ttg gtc gaa aga gtc att cag      528
Glu Thr Glu Asp Ile Thr Phe Ser Thr Leu Val Glu Arg Val Ile Gln
            165                 170                 175 cag ttg gaa ggc gcc ttt gca ctg gtt ttc aag agt att cac tac ccg      576
Gln Leu Glu Gly Ala Phe Ala Leu Val Phe Lys Ser Ile His Tyr Pro
        180                 185                 190 gga gaa gct gtc gcc acg agg aga ggc agc ccc ttg ctc atc ggg gta      624
Gly Glu Ala Val Ala Thr Arg Arg Gly Ser Pro Leu Leu Ile Gly Val
    195                 200                 205 cga agc aaa tac aaa ctc tcc aca gag cag atc ccc gtc tta tat ccg      672
Arg Ser Lys Tyr Lys Leu Ser Thr Glu Gln Ile Pro Val Leu Tyr Pro
210                 215                 220 aca tgc aat atc gag aat gtg aag aat atc tgc aag act agg atg aag      720
Thr Cys Asn Ile Glu Asn Val Lys Asn Ile Cys Lys Thr Arg Met Lys
225                 230                 235                 240 aga ctg gac agc tcc acc tgc ctg cac gct gtg ggc gat aaa gct gtg      768
Arg Leu Asp Ser Ser Thr Cys Leu His Ala Val Gly Asp Lys Ala Val
            245                 250                 255 gaa ttc ttc ttt gct tct gat gca agt gcc atc ata gaa cac acc aac      816
Glu Phe Phe Phe Ala Ser Asp Ala Ser Ala Ile Ile Glu His Thr Asn
        260                 265                 270 cgg gtc atc ttc tta gaa gat gat gat atc gct gca gtg gct gat ggg      864
Arg Val Ile Phe Leu Glu Asp Asp Asp Ile Ala Ala Val Ala Asp Gly
    275                 280                 285 aaa ctc tcc att cac cga gtc aag cgc tca gct act gat gac ccc tcc      912
Lys Leu Ser Ile His Arg Val Lys Arg Ser Ala Thr Asp Asp Pro Ser
290                 295                 300 cga gcc atc cag acc ttg cag atg gaa ctg cag caa ata atg aaa ggt      960
Arg Ala Ile Gln Thr Leu Gln Met Glu Leu Gln Gln Ile Met Lys Gly
305                 310                 315                 320 aac ttc agc gca ttt atg cag aag gag atc ttc gag cag cca gaa tca     1008
Asn Phe Ser Ala Phe Met Gln Lys Glu Ile Phe Glu Gln Pro Glu Ser
            325                 330                 335 gtt ttt aat acc atg aga ggt cgg gtg aat ttt gag acc aac aca gtg     1056
Val Phe Asn Thr Met Arg Gly Arg Val Asn Phe Glu Thr Asn Thr Val
        340                 345                 350 ctc ctg ggt ggc ttg aag gac cat ttg aaa gag atc cga cga tgc cga     1104
Leu Leu Gly Gly Leu Lys Asp His Leu Lys Glu Ile Arg Arg Cys Arg
    355                 360                 365 agg ctc att gtg att ggc tgt gga acc agc tac cat gcc gct gtg gct     1152
Arg Leu Ile Val Ile Gly Cys Gly Thr Ser Tyr His Ala Ala Val Ala
370                 375                 380 aca cgg caa gtc tta gag gaa ctg acc gag ctg cct gtg atg gtt gaa     1200
Thr Arg Gln Val Leu Glu Glu Leu Thr Glu Leu Pro Val Met Val Glu
385                 390                 395                 400 ctt gcc agt gac ttt ctg gac agg aac aca cct gtg ttc agg gat gac     1248
Leu Ala Ser Asp Phe Leu Asp Arg Asn Thr Pro Val Phe Arg Asp Asp
            405                 410                 415 gtt tgc ttt ttc ata agc caa tca ggt gag act gca gac acg ctc ctg     1296
Val Cys Phe Phe Ile Ser Gln Ser Gly Glu Thr Ala Asp Thr Leu Leu
        420                 425                 430 gcg ctg cga tac tgt aag gat cga ggt gcg ctg acc gtg ggc atc acc     1344
Ala Leu Arg Tyr Cys Lys Asp Arg Gly Ala Leu Thr Val Gly Ile Thr
    435                 440                 445 aac acc gtg ggt agc tcc atc tcc cgg gag act gac tgt ggc gtc cac     1392
Asn Thr Val Gly Ser Ser Ile Ser Arg Glu Thr Asp Cys Gly Val His
```

```
                  450             455                 460
atc aac gca ggg ccc gag att ggg gtg gcc agc acc aag gcg tac acc      1440
Ile Asn Ala Gly Pro Glu Ile Gly Val Ala Ser Thr Lys Ala Tyr Thr
465             470                 475                 480 agc cag ttc atc tct ctg gtg atg ttt ggt ttg atg atg tct gaa gat      1488
Ser Gln Phe Ile Ser Leu Val Met Phe Gly Leu Met Met Ser Glu Asp
                485                 490                 495 cga att tct cta cag aac agg aga caa gag atc atc cgt ggc ctc aga      1536
Arg Ile Ser Leu Gln Asn Arg Arg Gln Glu Ile Ile Arg Gly Leu Arg
            500                 505                 510 tct tta ccg gag ctg atc aaa gaa gtg ctg tcc ctg gat gag aag atc      1584
Ser Leu Pro Glu Leu Ile Lys Glu Val Leu Ser Leu Asp Glu Lys Ile
        515                 520                 525 cat gac ttg gcc ctg gag ctc tac aca caa agg tct ctc ctc gtg atg      1632
His Asp Leu Ala Leu Glu Leu Tyr Thr Gln Arg Ser Leu Leu Val Met
    530                 535                 540 gga cgg gga tat aac tat gcc aca tgt ctg gaa ggt gcc ttg aaa att      1680
Gly Arg Gly Tyr Asn Tyr Ala Thr Cys Leu Glu Gly Ala Leu Lys Ile
545                 550                 555                 560 aag gag ata acc tac atg cat tca gaa ggt atc cta gcc gga gag ctg      1728
Lys Glu Ile Thr Tyr Met His Ser Glu Gly Ile Leu Ala Gly Glu Leu
                565                 570                 575 aag cac ggg ccc ctt gct ctc gtc gac aag cag atg cca gtc atc atg      1776
Lys His Gly Pro Leu Ala Leu Val Asp Lys Gln Met Pro Val Ile Met
            580                 585                 590 gtc atc atg aag gat cct tgc ttt gcc aag tgc cag aat gcc ctg cag      1824
Val Ile Met Lys Asp Pro Cys Phe Ala Lys Cys Gln Asn Ala Leu Gln
        595                 600                 605 cag gtc act gcc cgc cag ggt cgc cca atc ata ctg tgt tcc aag gat      1872
Gln Val Thr Ala Arg Gln Gly Arg Pro Ile Ile Leu Cys Ser Lys Asp
    610                 615                 620 gac acc gag agc tcc aag ttt gca tat aaa acc att gaa ctt ccc cac      1920
Asp Thr Glu Ser Ser Lys Phe Ala Tyr Lys Thr Ile Glu Leu Pro His
625                 630                 635                 640 aca gtg gac tgt ctc cag ggt atc ctg agc gtg att cca ctc cag ctt      1968
Thr Val Asp Cys Leu Gln Gly Ile Leu Ser Val Ile Pro Leu Gln Leu
                645                 650                 655 ctg tcc ttc cac ctg gct gtc ctc cga ggt tat gat gtt gac ttc ccc      2016
Leu Ser Phe His Leu Ala Val Leu Arg Gly Tyr Asp Val Asp Phe Pro
            660                 665                 670 aga aac cta gcc aag tct gtc act gtg gaa tga                          2049
Arg Asn Leu Ala Lys Ser Val Thr Val Glu
        675                 680

<210> SEQ ID NO 7
<211> LENGTH: 682
<212> TYPE: PRT
<213> ORGANISM: Mus musculus

<400> SEQUENCE: 7

Met Cys Gly Ile Phe Ala Tyr Met Asn Tyr Arg Val Pro Lys Thr Arg
1               5                   10                  15

Lys Glu Ile Phe Glu Thr Leu Ile Arg Gly Leu Gln Arg Leu Glu Tyr
            20                  25                  30

Arg Gly Tyr Asp Ser Ala Gly Val Ala Ile Asp Gly Asn Asn His Glu
        35                  40                  45

Val Lys Glu Arg His Ile His Leu Val Lys Lys Arg Gly Lys Val Lys
    50                  55                  60

Ala Leu Asp Glu Glu Leu Tyr Lys Gln Asp Ser Met Asp Leu Lys Val
```

```
            65                  70                  75                  80
Glu Phe Glu Thr His Phe Gly Ile Ala His Thr Arg Trp Ala Thr His
                    85                  90                  95
Gly Val Pro Asn Ala Val Asn Ser His Pro Gln Arg Ser Asp Lys Asp
                100                 105                 110
Asn Glu Phe Val Val Ile His Asn Gly Ile Ile Thr Asn Tyr Lys Asp
                115                 120                 125
Leu Arg Lys Phe Leu Glu Ser Lys Gly Tyr Glu Phe Glu Ser Glu Thr
130                 135                 140
Asp Thr Glu Thr Ile Ala Lys Leu Ile Lys Tyr Val Phe Asp Asn Arg
145                 150                 155                 160
Glu Thr Glu Asp Ile Thr Phe Ser Thr Leu Val Glu Arg Val Ile Gln
                165                 170                 175
Gln Leu Glu Gly Ala Phe Ala Leu Val Phe Lys Ser Ile His Tyr Pro
                180                 185                 190
Gly Glu Ala Val Ala Thr Arg Arg Gly Ser Pro Leu Leu Ile Gly Val
                195                 200                 205
Arg Ser Lys Tyr Lys Leu Ser Thr Glu Gln Ile Pro Val Leu Tyr Pro
210                 215                 220
Thr Cys Asn Ile Glu Asn Val Lys Asn Ile Cys Lys Thr Arg Met Lys
225                 230                 235                 240
Arg Leu Asp Ser Ser Thr Cys Leu His Ala Val Gly Asp Lys Ala Val
                245                 250                 255
Glu Phe Phe Phe Ala Ser Asp Ala Ser Ala Ile Ile Glu His Thr Asn
                260                 265                 270
Arg Val Ile Phe Leu Glu Asp Asp Ile Ala Ala Val Ala Asp Gly
                275                 280                 285
Lys Leu Ser Ile His Arg Val Lys Arg Ser Ala Thr Asp Pro Ser
                290                 295                 300
Arg Ala Ile Gln Thr Leu Gln Met Glu Leu Gln Gln Ile Met Lys Gly
305                 310                 315                 320
Asn Phe Ser Ala Phe Met Gln Lys Glu Ile Phe Glu Gln Pro Glu Ser
                325                 330                 335
Val Phe Asn Thr Met Arg Gly Arg Val Asn Phe Glu Thr Asn Thr Val
                340                 345                 350
Leu Leu Gly Gly Leu Lys Asp His Leu Lys Glu Ile Arg Arg Cys Arg
                355                 360                 365
Arg Leu Ile Val Ile Gly Cys Gly Thr Ser Tyr His Ala Ala Val Ala
370                 375                 380
Thr Arg Gln Val Leu Glu Glu Leu Thr Glu Leu Pro Val Met Val Glu
385                 390                 395                 400
Leu Ala Ser Asp Phe Leu Asp Arg Asn Thr Pro Val Phe Arg Asp Asp
                405                 410                 415
Val Cys Phe Phe Ile Ser Gln Ser Gly Glu Thr Ala Asp Thr Leu Leu
                420                 425                 430
Ala Leu Arg Tyr Cys Lys Asp Arg Gly Ala Leu Thr Val Gly Ile Thr
                435                 440                 445
Asn Thr Val Gly Ser Ser Ile Ser Arg Glu Thr Asp Cys Gly Val His
                450                 455                 460
Ile Asn Ala Gly Pro Glu Ile Gly Val Ala Ser Thr Lys Ala Tyr Thr
465                 470                 475                 480
Ser Gln Phe Ile Ser Leu Val Met Phe Gly Leu Met Met Ser Glu Asp
                485                 490                 495
```

```
Arg Ile Ser Leu Gln Asn Arg Arg Gln Glu Ile Ile Arg Gly Leu Arg
                500                 505                 510
Ser Leu Pro Glu Leu Ile Lys Glu Val Leu Ser Leu Asp Glu Lys Ile
        515                 520                 525
His Asp Leu Ala Leu Glu Leu Tyr Thr Gln Arg Ser Leu Leu Val Met
530                 535                 540
Gly Arg Gly Tyr Asn Tyr Ala Thr Cys Leu Glu Gly Ala Leu Lys Ile
545                 550                 555                 560
Lys Glu Ile Thr Tyr Met His Ser Glu Gly Ile Leu Ala Gly Glu Leu
                565                 570                 575
Lys His Gly Pro Leu Ala Leu Val Asp Lys Gln Met Pro Val Ile Met
        580                 585                 590
Val Ile Met Lys Asp Pro Cys Phe Ala Lys Cys Gln Asn Ala Leu Gln
                595                 600                 605
Gln Val Thr Ala Arg Gln Gly Arg Pro Ile Ile Leu Cys Ser Lys Asp
        610                 615                 620
Asp Thr Glu Ser Ser Lys Phe Ala Tyr Lys Thr Ile Glu Leu Pro His
625                 630                 635                 640
Thr Val Asp Cys Leu Gln Gly Ile Leu Ser Val Ile Pro Leu Gln Leu
                645                 650                 655
Leu Ser Phe His Leu Ala Val Leu Arg Gly Tyr Asp Val Asp Phe Pro
        660                 665                 670
Arg Asn Leu Ala Lys Ser Val Thr Val Glu
                675                 680

<210> SEQ ID NO 8
<211> LENGTH: 1830
<212> TYPE: DNA
<213> ORGANISM: Escherichia coli
<220> FEATURE:
<221> NAME/KEY: CDS
<222> LOCATION: (1)..(1827)
<300> PUBLICATION INFORMATION:
<308> DATABASE ACCESSION NUMBER: U00096.2
<309> DATABASE ENTRY DATE: 2005-09-08
<313> RELEVANT RESIDUES IN SEQ ID NO: (3909862)..(3911691)

<400> SEQUENCE: 8 atg tgt gga att gtt ggc gcg atc gcg caa cgt gat gta gca gaa atc       48
Met Cys Gly Ile Val Gly Ala Ile Ala Gln Arg Asp Val Ala Glu Ile
1               5                   10                  15 ctt ctt gaa ggt tta cgt cgt ctg gaa tac cgc gga tat gac tct gcc       96
Leu Leu Glu Gly Leu Arg Arg Leu Glu Tyr Arg Gly Tyr Asp Ser Ala
            20                  25                  30 ggt ctg gcc gtt gtt gat gca gaa ggt cat atg acc cgc ctg cgt cgc      144
Gly Leu Ala Val Val Asp Ala Glu Gly His Met Thr Arg Leu Arg Arg
        35                  40                  45 ctc ggt aaa gtc cag atg ctg gca cag gca gcg gaa gaa cat cct ctg      192
Leu Gly Lys Val Gln Met Leu Ala Gln Ala Ala Glu Glu His Pro Leu
    50                  55                  60 cat ggc ggc act ggt att gct cac act cgc tgg gcg acc cac ggt gaa      240
His Gly Gly Thr Gly Ile Ala His Thr Arg Trp Ala Thr His Gly Glu
65                  70                  75                  80 cct tca gaa gtg aat gcg cat ccg cat gtt tct gaa cac att gtg gtg      288
Pro Ser Glu Val Asn Ala His Pro His Val Ser Glu His Ile Val Val
                85                  90                  95 gtg cat aac ggc atc atc gaa aac cat gaa ccg ctg cgt gaa gag cta      336
Val His Asn Gly Ile Ile Glu Asn His Glu Pro Leu Arg Glu Glu Leu
            100                 105                 110
```

-continued

| | |
|---|---|
| aaa gcg cgt ggc tat acc ttc gtt tct gaa acc gac acc gaa gtg att<br>Lys Ala Arg Gly Tyr Thr Phe Val Ser Glu Thr Asp Thr Glu Val Ile<br>115                       120                     125 | 384 |
| gcc cat ctg gtg aac tgg gag ctg aaa caa ggc ggg act ctg cgt gag<br>Ala His Leu Val Asn Trp Glu Leu Lys Gln Gly Gly Thr Leu Arg Glu<br>     130                     135                     140 | 432 |
| gcc gtt ctg cgt gct atc ccg cag ctg cgt ggt gcg tac ggt aca gtg<br>Ala Val Leu Arg Ala Ile Pro Gln Leu Arg Gly Ala Tyr Gly Thr Val<br>145                   150                     155                     160 | 480 |
| atc atg gac tcc cgt cac ccg gat acc ctg ctg gcg gca cgt tct ggt<br>Ile Met Asp Ser Arg His Pro Asp Thr Leu Leu Ala Ala Arg Ser Gly<br>                     165                     170                     175 | 528 |
| agt ccg ctg gtg att ggc ctg ggg atg ggc gaa aac ttt atc gct tct<br>Ser Pro Leu Val Ile Gly Leu Gly Met Gly Glu Asn Phe Ile Ala Ser<br>           180                     185                     190 | 576 |
| gac cag ctg gcg ctg ttg ccg gtg acc cgt cgc ttt atc ttc ctt gaa<br>Asp Gln Leu Ala Leu Leu Pro Val Thr Arg Arg Phe Ile Phe Leu Glu<br>                 195                     200                     205 | 624 |
| gag ggc gat att gcg gaa atc act cgc cgt tcg gta aac atc ttc gat<br>Glu Gly Asp Ile Ala Glu Ile Thr Arg Arg Ser Val Asn Ile Phe Asp<br>210                   215                     220 | 672 |
| aaa act ggc gcg gaa gta aaa cgt cag gat atc gaa tcc aat ctg caa<br>Lys Thr Gly Ala Glu Val Lys Arg Gln Asp Ile Glu Ser Asn Leu Gln<br>225                   230                     235                     240 | 720 |
| tat gac gcg ggc gat aaa ggc att tac cgt cac tac atg cag aaa gag<br>Tyr Asp Ala Gly Asp Lys Gly Ile Tyr Arg His Tyr Met Gln Lys Glu<br>                     245                     250                     255 | 768 |
| atc tac gaa cag ccg aac gcg atc aaa aac acc ctt acc gga cgc atc<br>Ile Tyr Glu Gln Pro Asn Ala Ile Lys Asn Thr Leu Thr Gly Arg Ile<br>                 260                     265                     270 | 816 |
| agc cac ggt cag gtt gat tta agc gag ctg gga ccg aac gcc gac gaa<br>Ser His Gly Gln Val Asp Leu Ser Glu Leu Gly Pro Asn Ala Asp Glu<br>     275                     280                     285 | 864 |
| ctg ctg tcg aag gtt gag cat att cag atc ctc gcc tgt ggt act tct<br>Leu Leu Ser Lys Val Glu His Ile Gln Ile Leu Ala Cys Gly Thr Ser<br>          290                     295                     300 | 912 |
| tat aac tcc ggt atg gtt tcc cgc tac tgg ttt gaa tcg cta gca ggt<br>Tyr Asn Ser Gly Met Val Ser Arg Tyr Trp Phe Glu Ser Leu Ala Gly<br>305                   310                     315                     320 | 960 |
| att ccg tgc gac gtc gaa atc gcc tct gaa ttc cgc tat cgc aaa tct<br>Ile Pro Cys Asp Val Glu Ile Ala Ser Glu Phe Arg Tyr Arg Lys Ser<br>                     325                     330                     335 | 1008 |
| gcc gtg cgt cgt aac agc ctg atg atc acc ttg tca cag tct ggc gaa<br>Ala Val Arg Arg Asn Ser Leu Met Ile Thr Leu Ser Gln Ser Gly Glu<br>               340                     345                     350 | 1056 |
| acc gcg gat acc ctg gct ggc ctg cgt ctg tcg aaa gag ctg ggt tac<br>Thr Ala Asp Thr Leu Ala Gly Leu Arg Leu Ser Lys Glu Leu Gly Tyr<br>     355                     360                     365 | 1104 |
| ctt ggt tca ctg gca atc tgt aac gtt ccg ggt tct tct ctg gtg cgc<br>Leu Gly Ser Leu Ala Ile Cys Asn Val Pro Gly Ser Ser Leu Val Arg<br>         370                     375                     380 | 1152 |
| gaa tcc gat ctg gcg cta atg acc aac gcg ggt aca gaa atc ggc gtg<br>Glu Ser Asp Leu Ala Leu Met Thr Asn Ala Gly Thr Glu Ile Gly Val<br>385                   390                     395                     400 | 1200 |
| gca tcc act aaa gca ttc acc act cag tta act gtg ctg ttg atg ctg<br>Ala Ser Thr Lys Ala Phe Thr Thr Gln Leu Thr Val Leu Leu Met Leu<br>                     405                     410                     415 | 1248 |
| gtg gcg aag ctg tct cgc ctg aaa ggt ctg gat gcc tcc att gaa cat<br>Val Ala Lys Leu Ser Arg Leu Lys Gly Leu Asp Ala Ser Ile Glu His | 1296 |

```
                   420              425              430
gac atc gtg cat ggt ctg cag gcg ctg ccg agc cgt att gag cag atg    1344
Asp Ile Val His Gly Leu Gln Ala Leu Pro Ser Arg Ile Glu Gln Met
            435              440              445 ctg tct cag gac aaa cgc att gaa gcg ctg gca gaa gat ttc tct gac    1392
Leu Ser Gln Asp Lys Arg Ile Glu Ala Leu Ala Glu Asp Phe Ser Asp
450              455              460 aaa cat cac gcg ctg ttc ctg ggc cgt ggc gat cag tac cca atc gcg    1440
Lys His His Ala Leu Phe Leu Gly Arg Gly Asp Gln Tyr Pro Ile Ala
465              470              475              480 ctg gaa ggc gca ttg aag ttg aaa gag atc tct tac att cac gct gaa    1488
Leu Glu Gly Ala Leu Lys Leu Lys Glu Ile Ser Tyr Ile His Ala Glu
            485              490              495 gcc tac gct gct ggc gaa ctg aaa cac ggt ccg ctg gcg cta att gat    1536
Ala Tyr Ala Ala Gly Glu Leu Lys His Gly Pro Leu Ala Leu Ile Asp
            500              505              510 gcc gat atg ccg gtt att gtt gtt gca ccg aac aac gaa ttg ctg gaa    1584
Ala Asp Met Pro Val Ile Val Val Ala Pro Asn Asn Glu Leu Leu Glu
            515              520              525 aaa ctg aaa tcc aac att gaa gaa gtt cgc gcg cgt ggc ggt cag ttg    1632
Lys Leu Lys Ser Asn Ile Glu Glu Val Arg Ala Arg Gly Gly Gln Leu
530              535              540 tat gtc ttc gcc gat cag gat gcg ggt ttt gta agt agc gat aac atg    1680
Tyr Val Phe Ala Asp Gln Asp Ala Gly Phe Val Ser Ser Asp Asn Met
545              550              555              560 cac atc atc gag atg ccg cat gtg gaa gag gtg att gca ccg atc ttc    1728
His Ile Ile Glu Met Pro His Val Glu Glu Val Ile Ala Pro Ile Phe
            565              570              575 tac acc gtt ccg ctg cag ctg ctg gct tac cat gtc gcg ctg atc aaa    1776
Tyr Thr Val Pro Leu Gln Leu Leu Ala Tyr His Val Ala Leu Ile Lys
            580              585              590 ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
            595              600              605 gag taa                                                            1830
Glu

<210> SEQ ID NO 9
<211> LENGTH: 609
<212> TYPE: PRT
<213> ORGANISM: Escherichia coli

<400> SEQUENCE: 9

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
```

-continued

```
            115                 120                 125
Ala His Leu Val Asn Trp Glu Leu Lys Gln Gly Gly Thr Leu Arg Glu
        130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                    165                 170                 175

Ser Pro Leu Val Ile Gly Leu Gly Met Gly Glu Asn Phe Ile Ala Ser
                180                 185                 190

Asp Gln Leu Ala Leu Leu Pro Val Thr Arg Arg Phe Ile Phe Leu Glu
            195                 200                 205

Glu Gly Asp Ile Ala Glu Ile Thr Arg Arg Ser Val Asn Ile Phe Asp
        210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                    245                 250                 255

Ile Tyr Glu Gln Pro Asn Ala Ile Lys Asn Thr Leu Thr Gly Arg Ile
                260                 265                 270

Ser His Gly Gln Val Asp Leu Ser Glu Leu Gly Pro Asn Ala Asp Glu
            275                 280                 285

Leu Leu Ser Lys Val Glu His Ile Gln Ile Leu Ala Cys Gly Thr Ser
        290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                    325                 330                 335

Ala Val Arg Arg Asn Ser Leu Met Ile Thr Leu Ser Gln Ser Gly Glu
                340                 345                 350

Thr Ala Asp Thr Leu Ala Gly Leu Arg Leu Ser Lys Glu Leu Gly Tyr
            355                 360                 365

Leu Gly Ser Leu Ala Ile Cys Asn Val Pro Gly Ser Ser Leu Val Arg
        370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                    405                 410                 415

Val Ala Lys Leu Ser Arg Leu Lys Gly Leu Asp Ala Ser Ile Glu His
                420                 425                 430

Asp Ile Val His Gly Leu Gln Ala Leu Pro Ser Arg Ile Glu Gln Met
            435                 440                 445

Leu Ser Gln Asp Lys Arg Ile Glu Ala Leu Ala Glu Asp Phe Ser Asp
        450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                    485                 490                 495

Ala Tyr Ala Ala Gly Glu Leu Lys His Gly Pro Leu Ala Leu Ile Asp
                500                 505                 510

Ala Asp Met Pro Val Ile Val Ala Pro Asn Asn Glu Leu Leu Glu
            515                 520                 525

Lys Leu Lys Ser Asn Ile Glu Glu Val Arg Ala Arg Gly Gly Gln Leu
        530                 535                 540
```

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
            565                 570                 575

Tyr Thr Val Pro Leu Gln Leu Leu Ala Tyr His Val Ala Leu Ile Lys
        580                 585                 590

Gly Thr Asp Val Asp Gln Pro Arg Asn Leu Ala Lys Ser Val Thr Val
            595                 600                 605

Glu

<210> SEQ ID NO 10
<211> LENGTH: 1830
<212> TYPE: DNA
<213> ORGANISM: Artificial Sequence
<220> FEATURE:
<223> OTHER INFORMATION: Synthetic sequence encoding an Escherichia coli
      protein having the activity of a GTFA

<400> SEQUENCE: 10

| | |
|---|---|
| atgtgcggaa ttgttggtgc tatcgcccaa agagacgttg ctgagatttt gttagagggt | 60 |
| ctgcgaaggc tagagtatag aggatatgac tccgctggtc tggctgtcgt tgatgctgag | 120 |
| ggtcatatga caaggctaag aaggttagga aaggttcaga tgcttgctca ggcagctgag | 180 |
| gaacatccat tgcatggagg tactggtatt gcacatacca ggtgggctac tcatgggag | 240 |
| ccatcagaag ttaatgctca tccacatgtg agtgagcata tcgttgtagt tcacaatggg | 300 |
| ataattgaaa ccacgaacc attgagggaa gagttaaagg caagaggata tacttttgtg | 360 |
| agtgagactg acactgaggt tattgcacat ttagtgaact gggaactcaa acagggggc | 420 |
| acattgcgtg aggctgtgtt aagagctatt cctcaactta gaggtgcata cggtactgtt | 480 |
| attatggatt caagacaccc agatactctc cttgcagcta gatcaggtag tcccttggtc | 540 |
| ataggacttg aatgggtga aaattttatc gctagcgacc aattggcctt attgccagtt | 600 |
| acaagacgat ttatttttcct tgaagagggc gatattgctg agattactag aaggtctgtg | 660 |
| aacatctttg ataagactgg cgctgaggtt aaacgtcagg atatcgagtc taaccttcaa | 720 |
| tacgatgctg gtgataaagg aatttacagg cattatatgc aaaaggaaat ttatgaacaa | 780 |
| ccaaatgcta tcaaaaacac acttactggc cgtatttctc atggacaggt cgatttaagc | 840 |
| gagcttggtc ctaatgcaga cgaactgcta tcaaaagttg agcacataca gatactggca | 900 |
| tgcggaacta gttataattc aggaatggtc tctagatact ggttcgaaag cttggcaggt | 960 |
| ataccttgtg atgtagagat cgcttctgag tttaggtata gaaagtctgc tgtgcgtaga | 1020 |
| aattcattaa tgattacatt atctcaatcc ggagaaacag cagatacact ggctggattg | 1080 |
| aggctttcta aggaactcgg atatctgggt tcacttgcta tttgtaatgt accaggttcc | 1140 |
| tcattggttc gtgaatcaga tctagcactt atgacaaatg caggaactga ataggtgtg | 1200 |
| gcaagtacca aggctttcac aacccaactg accgtacttt taatgttggt agcaaaactc | 1260 |
| agtcgattaa aggggctaga tgcatctatc gaacatgata ttgttcacgg gcttcaagct | 1320 |
| ctcccttcaa gaattgaaca aatgctttca caagataaga aatagaggc attggctgaa | 1380 |
| gatttttccg acaaacatca cgcattgttt cttggacgtg gcgatcaata tccaattgca | 1440 |
| ttggaaggag ctttgaagtt gaaagaaata agttacattc acgcagaagc atatgcagct | 1500 |
| ggagaactca agcatggtcc tttggcactc atcgacgctg acatgcccgt gatcgtagtg | 1560 |
| gctcctaata acgaactgct cgaaaagctt aaatcaaata tcgaagaggt tcgagctaga | 1620 |

```
ggaggtcagc tttacgtttt cgctgaacaa gatgctggat tcgtgtcaag cgataatatg    1680
catataattg aaatgcctca cgttgaagaa gtgattgcac ctatatttta tacagtccca    1740
ttgcaacttc tagcttacca tgttgcactt attaaaggaa ctgatgttga tcagcctaga    1800
aacctagcaa aatctgtaac agtcgaataa                                     1830

<210> SEQ ID NO 11
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 11
tcgacaggcc tggatcctta attaaactag tctcgaggag ctcggtac                 48

<210> SEQ ID NO 12
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 12
cgagctcctc gagactagtt taattaagga tccaggcctg                          40

<210> SEQ ID NO 13
<211> LENGTH: 38
<212> TYPE: DNA
<213> ORGANISM: Artificial Sequence
<220> FEATURE:
<223> OTHER INFORMATION: synthetic oligonucleotide used as primer

<400> SEQUENCE: 13
aaaaactagt tctacatcgg cttaggtgta gcaacacg                            38

<210> SEQ ID NO 14
<211> LENGTH: 39
<212> TYPE: DNA
<213> ORGANISM: Artificial Sequence
<220> FEATURE:
<223> OTHER INFORMATION: Synthetic oligonucleotide used as primer

<400> SEQUENCE: 14
aaaagatatc tgttgttgga ttctactact atgcttcaa                           39
```